US007795212B2

(12) United States Patent
Zhou

(10) Patent No.: US 7,795,212 B2
(45) Date of Patent: Sep. 14, 2010

(54) NEUREGULIN BASED METHODS AND COMPOSITIONS FOR TREATING CARDIOVASCULAR DISEASES

(75) Inventor: Mingdong Zhou, Shanghai (CN)

(73) Assignee: Zensun (Shanghai) Science & Technology Limited, Shanghai (CN)

(*) Notice: Subject to any disclaimer, the term of this patent is extended or adjusted under 35 U.S.C. 154(b) by 594 days.

(21) Appl. No.: 10/997,167

(22) Filed: Nov. 24, 2004

(65) Prior Publication Data
US 2006/0019888 A1 Jan. 26, 2006

Related U.S. Application Data

(63) Continuation of application No. PCT/CN03/00355, filed on May 15, 2003, and a continuation-in-part of application No. PCT/CN02/00349, filed on May 24, 2002, and a continuation-in-part of application No. PCT/CN02/00664, filed on Sep. 18, 2002.

(51) Int. Cl.
A61K 38/00 (2006.01)
(52) U.S. Cl. .................................................. 514/12
(58) Field of Classification Search .................... 514/12
See application file for complete search history.

(56) References Cited

U.S. PATENT DOCUMENTS

| 3,773,919 | A | 11/1973 | Boswell et al. |
| 4,179,337 | A | 12/1979 | Davis et al. |
| 4,301,144 | A | 11/1981 | Iwashita et al. |
| 4,485,045 | A | 11/1984 | Regen |
| 4,496,689 | A | 1/1985 | Mitra |
| 4,544,545 | A | 10/1985 | Ryan et al. |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 5,367,060 | A | 11/1994 | Vandlen et al. |
| 5,530,109 | A | 6/1996 | Goodearl et al. |
| 5,586,110 | A | 12/1996 | Nakaki et al. |
| 5,641,869 | A | 6/1997 | Vandlen et al. |
| 5,667,780 | A | 9/1997 | Ho et al. |
| 5,714,385 | A | 2/1998 | Mather et al. |
| 5,716,930 | A | 2/1998 | Goodearl et al. |
| 5,721,139 | A | 2/1998 | Mather et al. |
| 5,834,229 | A | 11/1998 | Vandlen et al. |
| 5,840,525 | A | 11/1998 | Vandlen et al. |
| 5,859,206 | A | 1/1999 | Vandlen et al. |
| 5,968,511 | A | 10/1999 | Akita et al. |
| 6,033,660 | A | 3/2000 | Mather et al. |
| 6,087,323 | A | 7/2000 | Gwynne et al. |
| 6,096,873 | A | 8/2000 | Schaefer et al. |
| 6,121,415 | A | 9/2000 | Godowski et al. |
| 6,136,558 | A | 10/2000 | Ballinger et al. |
| 6,156,728 | A | 12/2000 | Gao et al. |
| 6,162,641 | A | 12/2000 | Goldman et al. |
| 6,169,070 | B1 | 1/2001 | Chen et al. |
| 6,252,051 | B1 | 6/2001 | Godowski et al. |
| 6,387,638 | B1 | 5/2002 | Ballinger et al. |
| 6,399,746 | B1 | 6/2002 | Vandlen et al. |
| 6,444,642 | B1 | 9/2002 | Skylar et al. |
| 6,446,242 | B1 | 9/2002 | Lien et al. |
| 6,593,290 | B1 | 7/2003 | Gao et al. |
| 6,635,249 | B1 | 10/2003 | Marchionni et al. |
| 6,750,196 | B1 * | 6/2004 | Reh et al. ..................... 514/2 |
| 7,226,907 | B1 * | 6/2007 | Zhou ........................... 514/12 |

FOREIGN PATENT DOCUMENTS

| AU | 68278/94 A | 12/1994 |
| DE | 3218121 A1 | 11/1983 |
| EP | 0 036 676 A1 | 9/1981 |
| EP | 0 052 322 A2 | 5/1982 |
| EP | 0 058 481 A1 | 8/1982 |
| EP | 0 088 046 A2 | 9/1983 |
| EP | 0 102 324 A2 | 3/1984 |
| EP | 0 143 949 A1 | 6/1985 |
| EP | 0 133 988 A2 | 3/1995 |
| EP | 0 647 449 A1 | 4/1995 |
| EP | 0 142 641 A2 | 5/1995 |
| JP | 60007934 A | 1/1985 |
| WO | WO 89/01489 | 2/1989 |
| WO | WO 92/18627 | 10/1992 |
| WO | WO 94/00140 | 1/1994 |
| WO | WO 94/26298 | 11/1994 |
| WO | WO 95/32724 | 12/1995 |
| WO | WO 96/15812 | 5/1996 |
| WO | WO 97/09425 | 3/1997 |
| WO | WO 99/18976 | 4/1999 |
| WO | 0037095 | * 6/2000 |
| WO | 0064400 | * 11/2000 |
| WO | WO 01/64877 | 9/2001 |

OTHER PUBLICATIONS

Balligand, et al., "Cardiac endothelium and tissue growth," Prog Cardiovasc Dis. Jan-Feb. 1997; 39(4):351-360.
Chien, et al., "Regulation of cardiac gene expression during myocardial growth and hypertrophy: molecular studies of an adaptive physiologic response," FASEB J. Dec. 1991; 5(15):3037-3046.
Colucci, et al., "Pathphysiology of heart failure," Chapter 13 in *Heart Diseases: A textbook of cardiovascular medicine*, Braunwald, ed., Saunders, Philadelphia. 1996; 5:394-420.
Dias, et al., "The molecular basis of skeletal muscle differentiation," Semin Diagn Pathol. Feb. 1994; 11(1):3-14.
Eppstein, et al., "Biological activity of liposome-encapsulated murine interferon gamma is mediated by a cell membrane receptor," Proc Natl Acad Sci U S A. Jun. 1985; 82(11):3688-3692.
Florini-Jr., et al., "Stimulation of myogenic differentiation by a neuregulin, glial growth factor 2," J Biol Chem. May 31, 1996; 271(22):12699-12702.

(Continued)

Primary Examiner—Maryam Monshipouri
(74) Attorney, Agent, or Firm—Jones Day

(57) ABSTRACT

The present invention relates to compositions and methods for preventing, treating or delaying various cardiovascular diseases or disorders in mammals, particularly in humans. More particularly, the present invention provides for compositions and methods for preventing, treating or delaying various cardiovascular diseases or disorders using, inter alia, a neuregulin protein, or a functional fragment thereof, or a nucleic acid encoding a neuregulin protein, or a functional fragment thereof, or an agent that enhances production and/or function of said neuregulin.

26 Claims, 13 Drawing Sheets

OTHER PUBLICATIONS

Holmes, et al., "Identification of heregulin, a specific activator of p185erbB2," Science. May 22, 1992; 256(5060):1205-1210.

Hwang, et al., "Hepatic uptake and degradation of unilamellar sphingomyelin/cholesterol liposomes: a kinetic study," Proc Natl Acad Sci USA. Jul. 1980; 77(7):4030-4034.

Langer, et al., "Biocompatibility of polymeric delivery systems for macromolecules," J Biomed Mater Res. Mar. 1981; 15(2):267-277.

Parker, et al., "p53-independent expression of p21Cipl in muscle and other terminally differentiating cells," Science. Feb. 17, 1995; 267(5200):1024-1027.

*Physicians' Desk Reference*. Medical Economics Data Production Co., Montvale, NJ. 1994; pp. 2314-2320.

Rumyantsev, "Interrelations of the proliferation and differentiation processes during cardiac myogenesis and regeneration," Int Rev Cytol. 1977; 51:186-273.

Sidman, et al., "Controlled release of macromolecules and pharmaceuticals from synthetic polypeptides based on glutamic acid," Biopolymers. Jan. 1983; 22(1):547-556.

Simpson, et al., "Myocyte hypertrophy in neonatal rat heart cultures and its regulation by serum and by catecholamines," Circ Res. Dec. 1982; 51(6):787-801.

Zhao, et al., "Neuregulins promote survival and growth of cardiac myocytes. Persistence of ErbB2 and ErbB4 expression in neonatal and adult ventricular myocytes," J Biol Chem. Apr. 24, 1998; 273(17):10261-10269.

Zhao, et al., "Selective disruption of neuregulin-1 function in vertebrate embryos using ribozyme-tRNA transgenes," Development. May 1998; 125(10):1899-1907.

Zhou, et al., "Retinoid-dependent pathways suppress myocardial cell hypertrophy," Proc Nati Acad Sci U S A. Aug. 1, 1995; 92(16):7391-7395.

International Search Report from International Application No. PCT/CNO3/00355, dated Jul. 3, 2003.

Gray H., Gray'Anatomy: The Anatomical Basis of Medicine and Surgery, 1995, Ed. Williams et al., Churchill Livingstone, Edinburgh, pp. 264-265, 298-310 and 739-771.

\* cited by examiner 1k
500bp

300bp
150bp
50bp 1  2  3

1 2 3 4 5 6 7 8 9

SEQUENCE LISTING

<160> NUMBER OF SEQ ID NOS: 4

<210> SEQ ID NO 1
<211> LENGTH: 33
<212> TYPE: DNA
<213> ORGANISM: Artificial Sequence
<220> FEATURE:
<223> OTHER INFORMATION: Primer

<400> SEQUENCE: 1
tcgaacatat gagccatctt gtaaaatgtg cgg                              33

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
tcgaagggcc ctcactggta cagctcctcc                                  30

<210> SEQ ID NO 3
<211> LENGTH: 183
<212> TYPE: DNA
<213> ORGANISM: Homo sapiens

<400> SEQUENCE: 3
agccatcttg taaaatgtgc ggagaaggag aaaactttct gtgtgaatgg aggggagtgc    60
ttcatggtga aagaccttc aaacccctcg agatacttgt gcaagtgccc aaatgagttt   120
actggtgatc gctgccaaaa ctacgtaatg gccagcttct acaaggcgga ggagctgtac   180
cag                                                               183

<210> SEQ ID NO 4
<211> LENGTH: 61
<212> TYPE: PRT
<213> ORGANISM: Homo sapiens

<400> SEQUENCE: 4

Ser His Leu Val Lys Cys Ala Glu Lys Glu Lys Thr Phe Cys Val Asn
1               5                   10                  15

```
                                  -continued

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60
```

NEUREGULIN BASED METHODS AND COMPOSITIONS FOR TREATING CARDIOVASCULAR DISEASES

The present application is a continuation of PCT/CN03/00355, filed May 15, 2003, now pending, a continuation-in-part of PCT/CN02/00349, filed May 24, 2002, now pending, a continuation-in-part of PCT/CN02/00664, filed Sep. 18, 2002, now pending. The present application is also related to Chinese Patent Application No. 02145145.1, filed Nov. 8, 2002 and Chinese Patent Application No. 03109976.9, filed Apr. 9, 2003. The disclosures of the above applications are incorporated by reference in their entireties.

TECHNICAL FIELD

The present invention relates to compositions and methods for preventing, treating or delaying various cardiovascular diseases or disorders in mammals, particularly in humans. More particularly, the present invention provides for compositions and methods for preventing, treating or delaying various cardiovascular diseases or disorders using, inter alia, a neuregulin protein, or a functional fragment thereof, or a nucleic acid encoding a neuregulin protein, or a functional fragment thereof, or an agent that enhances production and/or function of said neuregulin.

BACKGROUND ART

Viral myocarditis is inflammation of heart muscle caused by or associated with various viruses, which induce focal or diffuse inflammatory exudation in interstitial myocardium and degeneration, necrosis or lysis of cardiac muscle fiber. Viral myocarditis may be complicated by pericarditis or endocarditis. The outcome of viral myocarditis includes myocardial damage, heart dysfunction, arrhythmia and systemic symptoms. Viral myocarditis occurs at any age. In recent years, the incidence of viral myocarditis is increasing. The sequela of acute viral myocarditis include arrhythmia, heart failure, cardiac shock, and even sudden death. The disease may be prolonged with cardiac hypertrophy and permanent cardiac muscle injury. Cardiomyopathy finally results from immune reaction. The treatment of viral myocarditis includes antibiotics, heart protective agents, antioxidant such as high dose vitamin C, vitamin E, coenzyme Q10, nutrients for myocardium such as energy combination to provide enough nutrition for myocardium. These measures are applied to improve heart function, repair cardiac damage, and prevent heart failure, but the efficacy is not so ideal, especially for the structural and functional changes in myocarditis. No reliable therapy is available for these pathological changes.

Dilated (congestive) cardiomyopathy (DCM) is the eventual outcome of various myocardial diseases of unidentified origin. Its pathological changes are non-rheumatic, non-hypertensive and not due to coronary heart disease. The main clinical features of dilated cardiomyopathy is ventricular hypertrophy, myocardial pump function failure, or congestive heart failure. Hypertrophy of nucleus and organelles is generally seen in mild myocardium damage of dilated cardiomyopathy. Structural change, cell death and the resultant fibrosis is usually seen in severe damage. The etiology and pathogenesis of DCM remains to be clarified. The prognosis of DCM is very poor because no effective therapy is available. Most of such patients die of increasingly worsen heart failure. Sudden death may result from arrhythmia. At present, no specific effective therapy is available for DCM. The routine treatment for DCM includes administration of cardiac tonics, diuretics, ACEI and other drugs. In addition, third generation calcium antagonist amlodipine and third generation β-receptor antagonist such as carvedilol are also used to treat DCM. It is controversial about the effect of thyroxin and growth hormone because no randomized double-blind clinical trial evidence is available. Volume reduction surgery of left ventricle can decrease the inside diameter of left ventricle and improve cardiac function temporarily. However, the higher mortality associated with post-operational heart failure and arrhythmia hampers the application of this method. Dynamic cardiomyoplasty is useful in improving cardiac function, but patient can not tolerate the relatively extensive trauma. Therefore, this operation is only used as alternative to heart transplant. In surgery, heart transplant is radical treatment for DCM. However, lack of donor heart, expensive cost, post-operation infection and transplant rejection are the main obstacles. Therefore, new therapy for DCM is urgently needed in clinical practice.

Doxorubicin or adriamycin (ADM) belongs to anthracycline anticancer agents with a broad spectrum and potent anti-tumor activity. It has been widely used in clinical practice to treat various malignant tumors such as lung cancer, breast cancer, bladder carcinoma, testis carcinoma, thyroid cancer, soft tissue carcinoma, osteosarcoma, neuroblastoma, acute leukemia, malignant lymphoma, gastric carcinoma, liver cancer, esophageal carcinoma, and cervical carcinoma. ADM acts through incorporation with DNA to inhibit DNA synthesis. The inhibition effect is observed in S, M, G1 and G2 phases, but the activity is most active in S phase. It has been discovered that a higher dose of chemotherapy agents produces better clinical efficacy and longer survival in unit time for breast cancer patients, whether metastatic or post-operative chemotherapy. Other studies have confirmed the importance of higher dose and dose potency, as well as the relation between dose, dose potency and efficacy.

However, the application of ADM is restricted by its toxic side effects. The toxicity of ADM includes bone marrow depression. In about 60-80% patients, leukocyte and platelet counts decrease to the lowest level 10-15 days after administration, and recover to normal levels 21 days later. Major digestive tract reaction are nausea, vomiting, anorexia, gastritis and even ulcer and stomatitis. Alopecia also occurs in nearly all patients treated with ADM, although this effect can be reversed after withdrawal.

More importantly, the major factor preventing clinical application of higher dose ADM and other anthracycline agents is cardiac toxicity. Cardiac toxicity of ADM may result from the production of oxygen-derived free radicals. The semiquinone group in ADM can induce an oxidoreduction reaction, which leads to enhanced lipid peroxidation, contributing to cellular damage. The free radicals damage cell membrane and organelle membrane, and modify the function of membrane proteins and enzyme activity. These changes can lead to intracellular calcium overload, inhibition of DNA and protein synthesis, and energy metabolism disorder, which inevitably harm the cardiac contraction and relaxation process.

Cardiac toxicity occurs when ADM accumulates in the body because ADM has a higher affinity for cardiac tissue than for other tissues. Thus, the heart is more vulnerable to the toxic effect of ADM. Cardiac toxicity may be acute or chronic. Clinical features of acute cardiac toxicity include cardiac functional changes, such as sinus tachycardia, arrhythmia, conduction block, ST-T segment alteration, etc. Various arrhythmia may be present at early stages of ADM therapy. Acute cardiac toxicity can also include decrease of the left ventricular ejection fraction (LVEF), as well as decreases in stroke volume (SV), cardiac output (CO) and cardiac index (CI). ADM has also been suggested to inhibit the contraction and pumping ability of the left ventricle. Chronic cardiac toxicity include irreversible congestive heart failure. Once a person suffers from congestive heart failure, the mortality decreases to about 30% to 50%. Because of the cardiac toxicity associated with ADM, some patients have to terminate ADM therapy, or reduce the dosage or length of ADM use, affecting the efficacy of ADM therapy.

Studies have been conducted to find ways to reduce the toxicity of ADM, while maintaining the therapeutic effect. Certain measures, such as decreasing the total dose of ADM or administering myocardial nutrients such as a high dose of vitamin C, may be helpful in protecting myocardium. Regular blood transfusion and administering an iron chelating agent ICRF-187 also have some effect in protecting myocardium. However, although these supportive agents are beneficial to the cardiac muscle, they have little effect on the cardiac toxicity induced by ADM. Thus, there exists a need in the art for preventing, treating or delaying the cardiac toxicity of ADM without affecting its efficacy.

Heart failure is caused by many etiology such as coronary arteriosclerosis, hypertension and inflammation induced myocardial injury, finally leading to refractory heart disease. These factors cause changes in myocardial cell structure and function, eventually resulting in lower ventricular pumping function and heart failure. The incidence and mortality of heart failure is very high worldwide, being one of the most severe lethal diseases. In the United States, 30%-40% of the congestive heart failure (CHF) lead to hospitalization annually. Mortality 5 years after establishment of the diagnosis of CHF is 60% (male) and 45% (female). Mean survival time is 3.2 years (male) and 5.4 years (female), while the survival rate of patients with final stage CHF is only about 20%.

Neuregulin-1 (NRG-1), also named as Neu Differentiation Factor(NDF) or Glial Growth Factor (GGF), is a ligand of ErbB3 and ErbB4. The study in neuregulin gene defective mouse fetus demonstrates that neuregulin is essential for the development of heart and nervous system. However, the data are limited about the way neuregulin controls cell differentiation and downstream signal transduction. At early stage of heart development, neuregulin and ErbB receptor are expressed in the lining of endocardium and cardiac myocytes respectively. As these 2 layers are separated widely, neuregulin has to pass through the space between these 2 layers before it can activate ErbB receptor. The activation of ErbB receptors in cardiocyte is helpful for cardiocyte and its migration into endocardium. WO 00/37095 shows that neuregulin can enhance the differentiation of cardiac myocytes, strengthen the combination of sarcomere and cytoskeleton, as well as intercellular cohesion. WO 00/37095 also shows that neuregulin can be used to detect, diagnose and treat heart diseases. WO 00/37095 further shows that neuregulin and its analogues can promote cardiocyte differentiation in vitro, induce reconstruction of sarcomere and cytoskeleton in cardiocyte and intercellular cohesion, identify the polypeptide or compound that can inhibit neuregulin. The identified polypeptide or compound can be used to treat heart diseases and heart failure.

There exists a need in the art for more efficient and/or cost effective neuregulin related treatments for viral myocarditis, dilated cardiomyopathy, the cardiac toxicity of a prophylactic or therapeutic agent, e.g., ADM, without affecting its efficacy and myocardial infarction. The present invention addresses these and other related needs in the art.

DISCLOSURE OF THE INVENTION

Treating Viral Myocarditis or Dilated (congestive) Cardiomyopathy (DCM)

In one aspect, the present invention is directed to a method for preventing, treating or delaying viral myocarditis or dilated (congestive) cardiomyopathy (DCM) in a mammal, which method comprises administering to a mammal, to which such prevention, treatment or delay is needed or desirable, an effective amount of a neuregulin protein, or a functional fragment thereof, or a nucleic acid encoding a neuregulin protein, or a functional fragment thereof, or an agent that enhances production and/or function of said neuregulin, whereby said viral myocarditis or DCM is prevented, treated or delayed. Preferably, the neuregulin protein, or a functional fragment thereof, or a nucleic acid encoding a neuregulin protein, or a functional fragment thereof, or an agent that enhances production and/or function of said neuregulin is administered in vivo.

In another aspect, the present invention is directed to a combination, which combination comprises an effective amount of a neuregulin protein, or a functional fragment thereof, or a nucleic acid encoding a neuregulin protein, or a functional fragment thereof, or an agent that enhances production and/or function of said neuregulin, and an effective amount of a prophylactic or therapeutic agent for viral myocarditis or dilated (congestive) cardiomyopathy (DCM).

In still another aspect, the present invention is directed to a pharmaceutical composition for preventing, treating or delaying viral myocarditis or dilated (congestive) cardiomyopathy (DCM) in a mammal, which pharmaceutical composition comprises an effective amount of a neuregulin protein, or a functional fragment thereof, or a nucleic acid encoding a neuregulin protein, or a functional fragment thereof, or an agent that enhances production and/or function of said neuregulin.

Treating Cardiac Toxicity Associated with Prophylactic or Therapeutic Agents

It is an object of the present invention to provide methods for preventing, treating or delaying cardiac toxicity associated with prophylactic or therapeutic agents. In particular, it is an object of the present invention to provide methods for preventing, treating or decreasing cardiac toxicity of drug-induced cardiomyopathy.

The present invention provides methods for preventing, treating or delaying cardiac toxicity in a mammal to which such prevention, treatment or delay is needed or desirable, comprising administering to a mammal in vivo an effective amount of a prophylactic or a therapeutic agent and an effective amount of: (i) a neuregulin protein or a functional fragment thereof, (ii) a nucleic acid encoding a neuregulin protein or a functional fragment thereof; or (iii) an agent that enhances production or function of said neuregulin, whereby the cardiac toxicity associated with administration of said prophylactic or therapeutic agent is prevented, treated or delayed.

The present invention can be used to prevent, treat or delay any clinical manifestations of cardiac toxicity known to one of ordinary skill in the art, including but not limited to acute or chronic cardiac toxicity. For example, the present invention can be used to prevent, treat or delay tachycardia, arrhythmia and congestive heart failure. In a particular embodiment, the present invention can be used to prevent, treat or delay clinical manifestations of acute cardiac toxicity such as sinus tachycardia, arrhythmia, conduction block and ST-T segment alteration, as well as decreases in the left ventricular ejection fraction (LVEF), stroke volume (SV), cardiac output (CO) or cardiac index (CI). The present invention can also be used to prevent, treat or delay cardiac toxicity comprising the inhibition of the contracting and pumping ability of the left ventricle.

The present methods can be used to prevent, treat or delay cardiac toxicity associated with any prophylactic or therapeutic agent. In one embodiment, the prophylactic or therapeutic agent produces oxygen-derived free radicals, which cause cardiac toxicity. In another embodiment, the prophylactic or therapeutic agent enhances lipid peroxidation, which causes cardiac toxicity.

The present methods can be used to prevent, reduce or delay cardiac toxicity associated with anti-neoplasm agents. The anti-neoplasm agent is preferably an anthracycline. In a specific embodiment, the anti-neoplasm agent has the following formula I:

$$\text{[Structure of Formula I]}$$

wherein R1 is methoxy or hydrogen; and R2, R3 and R4 are hydroxy or hydrogen. Non-limiting examples of anthracycline for use in the present methods include adriamycin (or doxorubicin), daunorubicin, epirubicin, idarubicin, mitoxantrone, mitomycin, bleomycin, cyclophosphamide, fluorouracil, actinomycin D and vincristine. In one aspect, the present invention is directed to the use of neuregulin as an anti-cardiotoxic agent for preventing, treating or delaying cardiac toxicity induced by chemotherapeutic agents such as adriamycin (ADM), alone or in combination with another reagent.

The present methods can be used to prevent, reduce or delay cardiac toxicity associated with antipsychotic agents. The antipsychotic agent can be chlorpromazine, perphenazine or trifluperazine.

The present methods can be used to prevent, reduce or delay cardiac toxicity associated with tricyclic antidepressants. The tricyclic antidepressant can be chlorimipramine, amitriptyline or doxepin.

The present methods can be used to prevent, reduce or delay cardiac toxicity associated with interferon, e.g., interferon-α, or interleukin, e.g., interleukin-2.

The present methods can be used to prevent, reduce or delay cardiac toxicity associated with anti-infectious agents, e.g., emetine.

The neuregulin agent for use in the present methods can be neuregulin 1, neuregulin 2, neuregulin 3, or neuregulin 4. In a particular embodiment, the neuregulin for use in the present methods is neuregulin α2 or neuregulin β2. In another embodiment, the neuregulin fragment is a neuregulin β2 comprising an amino acid sequence set forth in SEQ ID NO:4.

The neuregulin agent can be administered as a protein or a functional fragment thereof. The neuregulin agent can also be administered as a nucleic acid encoding a neuregulin protein or a functional fragment thereof. Any agent that enhances production or function of neuregulin can also be administered. The neuregulin agent can be administered alone or with a pharmaceutically acceptable carrier or excipient. The neuregulin protein or a functional fragment thereof, or a nucleic acid encoding a neuregulin protein or a functional fragment thereof, or an agent that enhances production or function of said neuregulin, can be administered prior to, concurrently with, or subsequent to the administration of the prophylactic or therapeutic agent.

In one embodiment, the prophylactic or therapeutic agent is administered in an amount that is higher than a maximally allowed amount when the prophylactic or therapeutic agent is administered in the absence of the neuregulin protein or a functional fragment thereof, or a nucleic acid encoding a neuregulin protein or a functional fragment thereof, or an agent that enhances production or function of said neuregulin.

In a particular embodiment, the present invention provides methods for preventing, treating or delaying cardiac toxicity in a human to which such prevention, treatment or delay is needed or desirable. Preferably, the human has a malignant tumor such lung cancer, breast cancer, bladder carcinoma, testis carcinoma, thyroid cancer, soft tissue carcinoma, osteosarcoma, neuroblastoma, acute leukemia, malignant lymphoma, gastric carcinoma, liver cancer, esophageal carcinoma, or cervical carcinoma.

Treating Myocardial Infarction

In one aspect, the present invention is directed to a combination, which combination comprises an effective amount of a neuregulin protein, or a functional fragment thereof, or a nucleic acid encoding a neuregulin protein, or a functional fragment thereof, or an agent that enhances production and/or function of said neuregulin, and an effective amount of a prophylactic or therapeutic agent for myocardial infarction.

In another aspect, the present invention is directed to a kit, which kit comprises an above-described combination in a container and an instruction for using said combination in preventing, treating or delaying myocardial infarction.

In still another aspect, the present invention is directed to a method for preventing, treating or delaying myocardial infarction in a mammal, which method comprises administering to a mammal, to which such prevention, treatment or delay is needed or desirable, an effective amount of a neuregulin protein, or a functional fragment thereof, or a nucleic acid encoding a neuregulin protein, or a functional fragment thereof, or an agent that enhances production and/or function of said neuregulin, whereby said myocardial infarction is prevented, treated or delayed.

Pharmaceutical Compositions

In one aspect, the present invention is directed to a pharmaceutical composition for preventing, treating or delaying a disease in a mammal, which composition comprises a neuregulin protein, or a functional fragment thereof: a) in a safety dosage equals to or less than about 170 U/kg; or b) in a total regimen equals to or less than about 3,600 U/kg.

MODES FOR CARRYING OUT THE INVENTION

Figure 1:
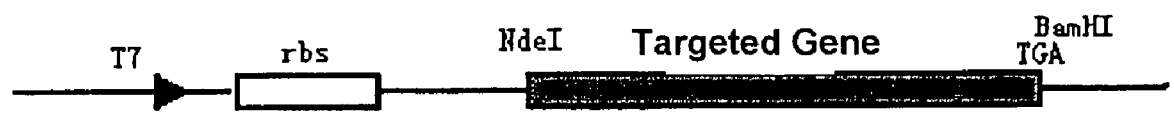
FIG. 1 illustrates construction of an engineered bacterial strain for recombinantly producing a neuregulin protein.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "neuregulin" refers to proteins or peptides that can activate ErbB2/ErbB4 or ErbB2/ErbB3 heterodimers protein kinases, such as all neuregulin isoforms, neuregulin EGF domain alone, neuregulin mutants, and any kind of neuregulin-like gene products that also activate the above receptors. An exemplary neuregulin fragment is a polypeptide fragment of human neuregulin β 2 isomer, which contains receptor-binding domain, i.e., EGF-like domain. This polypeptide can activate ErbB receptor of EGF receptor family and modulate its biological reactions, e.g., stimulate breast cancer cell differentiation and milk protein secretion; induce the differentiation of neural crest cell into Schwann cell; stimulate acetylcholine synthesis in skeletal muscle cell; and improve cardiocyte survival and DNA synthesis. Neuregulin also includes those variants with conservative amino acid substitutions that do not substantially alter their its anti-viral myocarditis, anti-DCM, anti-cardiotoxic, or anti-myocardial infarction activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Bejacmin/Cummings Pub. co., p. 224). Neuregulin protein encompasses a neuregulin protein and peptide. Neuregulin nucleic acid encompasses neuregulin nucleic acid and neuregulin oligonucleotide.

As used herein, "epidermal growth factor-like domain" or "EGF-like domain" refers to a polypeptide motif encoded by the neuregulin gene that binds to and activates ErbB2, ErbB3, ErbB4, or combinations thereof, and bears a structural similarity to the EGF receptor-binding domain as disclosed in WO 00/64400, Holmes et al., Science, 256:1205-1210 (1992); U.S. Pat. Nos. 5,530,109 and 5,716,930; Hijazi et al., Int. J. Oncol., 13:1061-1067 (1998); Chang et al., Nature, 387:509-512 (1997); Carraway et al., Nature, 387:512-516 (1997); Higashiyama et al., J. Biochem., 122:675-680 (1997); and WO 97/09425.

As used herein, a "functional derivative or fragment" of neuregulin refers to a derivative or fragment of the neuregulin protein or its encoding nucleic acid that still substantially retains its anti-viral myocarditis, anti-DCM, anti-cardiotoxic, or anti-myocardial infarction activity. Normally, the derivative or fragment retains at least 50% of its anti-viral myocarditis, anti-DCM, anti-cardiotoxic, or anti-myocardial infarction activity. Preferably, the derivative or fragment retains at least 60%, 70%, 80%, 90%, 95%, 99% and 100% of its anti-viral myocarditis, anti-DCM, anti-cardiotoxic, or anti-myocardial infarction activity.

As used herein, an "agent that enhances production of neuregulin" refers to a substance that increases transcription and/or translation of a neuregulin gene, or a substance that increases post-translational modification and/or cellular trafficking of a neuregulin precursor, or a substance that prolongs half-life of a neuregulin protein.

As used herein, an "agent that enhances function of neuregulin" refers to a substance that increases potency of the neuregulin's anti-viral myocarditis, anti-DCM activity, anti-cardiotoxic activity, or anti-myocardial infarction activity, or a substance that increases sensitivity of a neuregulin's natural ligand in an anti-viral myocarditis, anti-DCM, anti-cardiotoxic activity, or anti-myocardial infarction signaling pathway, or a substance that decreases potency of a neuregulin's antagonist. Such an agent is not a neuregulin protein or its encoding nucleic acid.

As used herein, a "combination" refers to any association between two or among more items.

As used herein, a "composition" refers to any mixture of two or more products or compounds. It may be a solution, a suspension, liquid, powder, a paste, aqueous, non-aqueous or any combination thereof.

As used herein, "erb" refers to two oncogenes, erb A and erb B, associated with erythroblastosis virus (an acute transforming retrovirus).

As used herein, "an effective amount of a compound for treating a particular disease" is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, "heart failure" is meant an abnormality of cardiac function where the heart does not pump blood at the rate needed for the requirements of metabolizing tissues. Heart failure includes a wide range of disease states such as congestive heart failure, myocardial infarction, tachyarrythmia, familial hypertrophic cardiomyopathy, ischaemic heart disease, idiopathic dilated cardiomyopathy, and myocarditis. The heart failure can be caused by any number of factors, including ischaemic, congenital, rheumatic, or idiopathic forms. Chronic cardiac hypertrophy is a significantly diseased state which is a precursor to congestive heart failure and cardiac arrest.

As used herein, "production by recombinant means" refers to production methods that use recombinant nucleic acid methods that rely on well known methods of molecular biology for expressing proteins encoded by cloned nucleic acids.

As used herein, "complementary" when referring to two nucleic acid molecules, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: "stringency of hybridization" in determining percentage mismatch is as follows:
 1) high stringency: 0.1×SSPE, 0.1% SDS, 65° C.;
 2) medium stringency: 0.2×SSPE, 0.1% SDS, 50° C. (also referred to as moderate stringency); and
 3) low stringency: 1.0×SSPE, 0.1% SDS, 50° C.

It is understood that equivalent stringencies may be achieved using alternative buffers, salts and temperatures.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eucaryotic cells and/or prokaryotic cells and those that remain episomal or those which integrate into the host cell genome.

As used herein, "a promoter region or promoter element" refers to a segment of DNA or-RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, J. Biol. Chem., 266: 19867-19870 (1991)) can be inserted immediately 5' of the start codon and may enhance expression. The desirability of (or need for) such modification may be empirically determined.

As used herein, "amelioration" of the symptoms of a particular disorder by administration of a particular pharmaceutical composition refers to any lessening, whether permanent or temporary, lasting or transient that can be attributed to or associated with administration of the composition.

As used herein, "a therapeutic agent" refers to any conventional drug or drug therapies which are known to those skilled in the art, including, but not limited to prophylactic or chemotherapeutic agents.

As used herein, "therapeutically effective amount" refers to that amount that is sufficient to ameliorate, or in some manner reduce the symptoms associated with a disease. Such amount may be administered as a single dosage or according to a regimen. Repeated administration may be required to achieve the desired amelioration of symptoms.

As used herein, "administration" or "administering" a compound refers to any suitable method of providing a compound to a subject.

As used herein, "treatment" or "treating" refer to any manner in which the symptoms of a condition, disorder or disease are ameliorated or otherwise beneficially altered. Treatment also encompasses any pharmaceutical use of the compositions herein. Amelioration of symptoms of a particular disorder refers to any lessening of symptoms, whether permanent or temporary, that can be attributed to or associated with administration of the composition.

As used herein, "neoplasm (neoplasia)" refers to abnormal new growth or tumor growth, which may be benign or malignant. Unlike hyperplasia, neoplastic proliferation persists even in the absence of the original stimulus.

As used herein, "an anti-neoplasm agent" refers to any agents used to prevent the occurrence or lessen the severity of neoplasm, tumor or cancer. These include, but are not limited to, anti-angiogenic agents, alkylating agents, antimetabolites, natural products, platinum coordination complexes, anthracenedione, substituted urea, methylhydrazine derivatives, adrenocortical suppressants, hormones, antagonists, oncogene inhibitors, tumor suppressor genes or proteins, anti-oncogene antibodies, or anti-oncogene antisense oligonucleotides.

As used herein, "anti-psychotic agent" refers to any agents used in the treatment of psychiatric disorders. These include, but are not limited to, tricyclic phenothiazines, thioxanthenes, and dibenzepines, as well as butyrophenones and congeners, other heterocyclics, and experimental benzamides.

As used herein, "tricyclic antidepressants" refers to any agents used in the treatment of depression. These include, but are not limited to, agents that inhibit norepinephrine and serotonin uptake into nerve endings, and thus leading to sustained facilitation of noradrenergic function in the brain.

As used herein, "anti-infectious agent" refers to any agents used in the treatment of infectious diseases. These include, but are not limited to, agents for use against parasitic infections, bacterial and microbial infections.

As used herein, "safety dosage" refers to a dosage sufficient to prevent, treat or delay a disease in mammal without inducing intolerable toxic or other side effects in said mammal.

As used herein, "myocardial infarction" refers to blockade of coronary artery, blood flow interruption, leading to focal necrosis of part of the myocardium caused by severe and persistent ischemia.

B. Methods for Preventing, Treating or Delaying Viral Myocarditis or DCM

In one aspect, the present invention is directed to a method for preventing, treating or delaying viral myocarditis or dilated (congestive) cardiomyopathy (DCM) in a mammal, which method comprises administering to a mammal, to which such prevention, treatment or delay is needed or desirable, an effective amount of a neuregulin protein, or a functional fragment thereof, or a nucleic acid encoding a neuregulin protein, or a functional fragment thereof, or an agent that enhances production and/or function of said neuregulin, whereby said viral myocarditis or DCM is prevented, treated or delayed.

The present method can be used for preventing, treating or delaying viral myocarditis or DCM in any mammals, such as mice, rats, rabbits, cats, dogs, pigs, cows, ox, sheep, goats, horses, monkeys and other non-human primates. Preferably, the present method is used for preventing, treating or delaying viral myocarditis or DCM in humans.

Any suitable neuregulin protein, or a functional fragment thereof, or a nucleic acid encoding a neuregulin protein, or a functional fragment thereof, can be used in the present methods. In one specific embodiment, the neuregulin used in the present methods carries out its anti-viral myocarditis or anti-DCM activity via binding with ErbB2-ErbB4 receptors. In another specific embodiment, neuregulin 1, neuregulin 2, neuregulin 3 or neuregulin 4 is used in the present methods. Synonyms of neuregulin 1 include heregulin, GGF2 and p185erbB2 ligand. See e.g., WO 00/64400 and U.S. Pat. Nos. 5,530,109 and 5,716,930. Both neuregulin α2 and neuregulin β2 can be used in the present methods. Preferably, a neuregulin β2 fragment comprising an amino acid sequence set forth in SEQ ID NO:4 is used in the present methods.

In still another specific embodiments, neuregulins or functional fragments thereof disclosed in the following patents, patent applications and GenBank databases can be used in the present methods: U.S. Pat. Nos. 6,252,051 and 6,121,415 (NRG3); U.S. Pat. No. 6,087,323 (neuregulin with $p185^{erbB2}$, $p185^{erbB3}$ or $p185^{erbB4}$ binding activity); U.S. Pat. No. 6,033,906 (neuregulin as a ligand for a receptor selected from the group consisting of $p185^{erbB2}$ and $p180^{erbB}4$); US2002002276 (The chimeric ErbB heteromultimer adhesins as competitive antagonists or agonists of a neuregulin); WO01/81540 (NRG-4); WO01/64877 (NRG1); WO01/64876 (NRG1AG1); WO01/58948 (neuregulin-beta); WO01/26607 (SMDF and GGF neuregulin splice variant isoforms); WO00/70322 (CRD-neuregulin); WO00/64400; WO99/18976; WO98/02540 (chimeric ErbB heteromultimer adhesins as competitive antagonists or agonists of a neuregulin); WO96/30403; WO96/15812; BC017568 (*Homo sapiens*, Similar to neuregulin 4); BC007675 (*Homo sapiens*, neuregulin 1); AF142632 (*Xenopus laevis* cysteine-rich domain neuregulin-1); AF194439 (*Rattus norvegicus* SMDF neuregulin alpha 2a (Nrg1)); AF194438 (*Rattus norvegicus* SMDF neuregulin beta 1a (Nrg1)); HS2NRG12 (*Homo sapiens* alternatively spliced neuregulin 2 (NRG2)); HS2NRG08 (*Homo sapiens* alternatively spliced neuregulin 2 (NRG2)); HS2NRG07 (*Homo sapiens* alternatively spliced neuregulin 2 (NRG2)); AF083067 (*Mus musculus* neuregulin-4 short isoform (Nrg4)); AF076618 (*Xenopus laevis* neuregulin alpha-1); AF045656 (*Gallus gallus* neuregulin beta-2b); AF045655 (*Gallus gallus* neuregulin beta-2a); AF045654 (Gallus gallus neuregulin beta-1a); MAU96612 (*Mesocricetus auratus* neuregulin); AF010130 (*Mus musculus* neuregulin-3 (NRG3)). Preferably, neuregulin(s) disclosed in the GenBank Accession No. NT_007995 (gi: 18570363) is used in the present methods.

Any viral myocarditis can be prevented, treated or delayed using the present methods. For example, the viral myocarditis caused by or associated with infection of a Coxsackie Group A virus, Coxsackie Group B virus, ECHO virus or polio virus can be prevented, treated or delayed using the present methods. Preferably, the viral myocarditis caused by or associated with infection of a Coxsackie Group B virus is prevented, treated or delayed using the present methods.

Viral myocarditis with various clinical features can be prevented, treated or delayed using the present methods. For example, the viral myocarditis that is complicated by pericarditis or endocarditis can be prevented, treated or delayed using the present methods. In another example, the viral myocarditis with a clinical feature of myocardial damage, heart dysfunction, arrhythmia, systemic symptom or cardiomyopathy can be prevented, treated or delayed using the present methods. Both the acute and the chronic viral myocarditis can be prevented, treated or delayed using the present methods. Preferably, the acute viral myocarditis having arrhythmia, heart failure or cardiac shock can be prevented, treated or delayed using the present methods. The viral myocarditis that is prolonged with cardiac hypertrophy and/or permanent cardiac muscle injury may also be prevented, treated or delayed using the present methods.

DCM with various clinical features can be prevented, treated or delayed using the present methods. For example, the DCM having ventricular hypertrophy, myocardial pump function failure or congestive heart failure can be prevented, treated or delayed using the present methods.

The neuregulin protein, or a functional fragment thereof, or a nucleic acid encoding a neuregulin protein, or a functional fragment thereof, can be administered alone. Alternatively, the neuregulin protein, or a functional fragment thereof, or a nucleic acid encoding a neuregulin protein, or a functional fragment thereof, can be administered with a pharmaceutically acceptable carrier or excipient.

The neuregulin protein, or a functional fragment thereof, or a nucleic acid encoding a neuregulin protein, or a functional fragment thereof, can be administered in vivo, i.e., administered directly into a mammal. Alternatively, the neuregulin protein, or a functional fragment thereof, or a nucleic acid encoding a neuregulin protein, or a functional fragment thereof, can be administered ex vivo, i.e., administered into cell(s), tissue(s) or organ(s) and such cell(s), tissue(s) or organ(s) carrying the neuregulin protein, or a functional fragment thereof, or a nucleic acid encoding a neuregulin protein, or a functional fragment thereof, can be transferred into a mammal.

In one specific embodiment, a neuregulin protein, or a functional fragment thereof, is administered. In another specific embodiment, a nucleic acid encoding a neuregulin protein, or a functional fragment thereof, is administered.

The neuregulin protein, or a functional fragment thereof, or a nucleic acid encoding a neuregulin protein, or a functional fragment thereof, can be used alone. Alternatively, the neuregulin protein, or a functional fragment thereof, or a nucleic acid encoding a neuregulin protein, or a functional fragment thereof, can be used in combination with a prophylactic or therapeutic agent for viral myocarditis or DCM. The neuregulin protein, or a functional fragment thereof, or a nucleic acid encoding a neuregulin protein, or a functional fragment thereof, can be administered prior to, concurrently with, or subsequent to the administration of the prophylactic or therapeutic agent for viral myocarditis or DCM.

Any suitable prophylactic or therapeutic agent for viral myocarditis can be used in the present methods. For example, the prophylactic or therapeutic agent for viral myocarditis can be an antibiotic, e.g., penicillin, a heart protective agent, e.g., taurine, an antioxidant, e.g., vitamin C, vitamin E and coenzyme Q10, and a nutrient for myocardium, e.g., an energy combination.

Any suitable prophylactic or therapeutic agent for DCM can be used in the present methods. For example, the prophylactic or therapeutic agent for DCM can be a cardiac tonic, e.g., digoxin and cedilanid, a diuretic (Goodman and Gilman's The Pharmacological Basis of Therapeutics (9th Ed.), McGraw-Hill (1996) pp 683-713), e.g., an inhibitor of carbonic anhydrase, an osmotic diuretic, an inhibitor of $Na^+$—$K^+$-$2Cl^-$ symport, an inhibitor of $Na^+$—$Cl^-$ symport, an inhibitor of renal epithelial $Na^+$ channels and an antagonist of mineralocorticoid receptors, angiotensin I-converting enzyme inhibitor (ACEI), a calcium antagonist, e.g., amlodipine, and a β-receptor antagonist, e.g., carvedilol.

C. Pharmaceutical Compositions, Kits and Combinations for Preventing, Treating or Delaying Viral Myocarditis or DCM In another aspect, the present invention is directed to a pharmaceutical composition for preventing, treating or delaying viral myocarditis or dilated (congestive) cardiomyopathy (DCM) in a mammal, which pharmaceutical composition comprises an effective amount of a neuregulin protein, or a functional fragment thereof, or a nucleic acid encoding a neuregulin protein, or a functional fragment thereof, or an agent that enhances production and/or function of said neuregulin.

Any suitable neuregulin protein, or a functional fragment thereof, or a nucleic acid encoding a neuregulin protein, or a functional fragment thereof, including the ones described in the above Section B, can be used in the present pharmaceutical compositions. In one specific embodiment, the neuregulin used in the present pharmaceutical compositions carries out its anti-viral myocarditis or anti-DCM activity via binding with ErbB2-ErbB4 receptors. In another specific embodiment, neuregulin 1, neuregulin 2, neuregulin 3 or neuregulin 4 is used in the present pharmaceutical compositions. Synonyms of neuregulin 1 include heregulin, GGF2 and p185erbB2 ligand. See e.g., WO 00/64400 and U.S. Pat. Nos. 5,530,109 and 5,716,930. Both neuregulin α2 and neuregulin β2 can be used in the present pharmaceutical compositions. Preferably, a neuregulin β2 fragment comprising an amino acid sequence set forth in SEQ ID NO:4 is used in the present pharmaceutical compositions.

The neuregulin protein, or a functional fragment thereof, or a nucleic acid encoding a neuregulin protein, or a functional fragment thereof, can be used in any suitable dosage ranges. For example, the neuregulin protein, or a functional fragment thereof, or a nucleic acid encoding a neuregulin protein, or a functional fragment thereof, can have a dosage range from about 25 µg to about 2,500 µg.

In still another aspect, the present invention is directed to a kit, which kit comprises the above pharmaceutical composition in a container and an instruction for using said pharmaceutical composition in preventing, treating or delaying viral myocarditis or DCM.

In yet another aspect, the present invention is directed to a combination, which combination comprises an effective amount of a neuregulin protein, or a functional fragment thereof, or a nucleic acid encoding a neuregulin protein, or a functional fragment thereof, or an agent that enhances production and/or function of said neuregulin, and an effective amount of a prophylactic or therapeutic agent for viral myocarditis or dilated (congestive) cardiomyopathy (DCM).

Any suitable neuregulin protein, or a functional fragment thereof, or a nucleic acid encoding a neuregulin protein, or a functional fragment thereof, including the ones described in the above Section B, can be used in the present combinations. In one specific embodiment, the neuregulin used in the present combinations carries out its anti-viral myocarditis or anti-DCM activity via binding with ErbB2-ErbB4 receptors. In another specific embodiment, neuregulin 1, neuregulin 2, neuregulin 3 or neuregulin 4 is used in the present combinations. Synonyms of neuregulin 1 include heregulin, GGF2 and p185erbB2 ligand. See e.g., WO 00/64400 and U.S. Pat. Nos.5,530,109 and 5,716,930. Both neuregulin α2 and neuregulin β2 can be used in the present combinations. Preferably, a neuregulin β2 fragment comprising an amino acid sequence set forth in SEQ ID:1 is used in the present combinations.

Any suitable prophylactic or therapeutic agent for viral myocarditis, including the ones described in the above Section B, can be used in the present combinations. For example, the prophylactic or therapeutic agent for viral myocarditis can be an antibiotic, e.g., penicillin, a heart protective agent, e.g., taurine, an antioxidant, e.g., vitamin C, vitamin E and coenzyme Q10, and a nutrient for myocardium, e.g., an energy combination.

Any suitable prophylactic or therapeutic agent for DCM, including the ones described in the above Section B, can be used in the present combinations. For example, the prophylactic or therapeutic agent for DCM can be a cardiac tonic, e.g., digoxin and cedilanid, a diuretic, e.g., an inhibitor of carbonic anhydrase, an osmotic diuretic, an inhibitor of $Na^+$—$K^+$-$2Cl^-$ symport, an inhibitor of Na+—$Cl^-$ symport, an inhibitor of renal epithelial $Na^+$ channels and an antagonist of mineralocorticoid receptors, angiotensin I-converting enzyme inhibitor (ACEI), a calcium antagonist, e.g., amlodipine, and a β-receptor antagonist, e.g., carvedilol.

In yet another aspect, the present invention is directed to a kit, which kit comprises the above combination in a container and an instruction for using said combination in preventing, treating or delaying viral myocarditis or DCM.

D. Methods for Preventing, Treating or Delaying Cardiac Toxicity

Neuregulin has been found to enhance the differentiation of cardiac myocytes, and strengthen the combination of sarcomere and cytoskeleton, as well as intercellular cohesion (WO 00/37095). Neuregulin can also be used to detect, diagnose and treat heart diseases. In the methods of the present invention, neuregulin is used as a cardiocyte protective agent for preventing, treating or delaying cardiac toxicity due to other prophylactic or therapeutic agents.

In one aspect, the present invention is directed to a method for preventing, treating or delaying cardiac toxicity in a mammal to which such prevention, treatment or delay is needed or desirable, comprising administering to a mammal in vivo an effective amount of a prophylactic or a therapeutic agent and an effective amount of: (i) a neuregulin protein or a functional fragment thereof; (ii) a nucleic acid encoding a neuregulin protein or a functional fragment thereof; or (iii) an agent that enhances production or function of said neuregulin, whereby the cardiac toxicity associated with administration of said prophylactic or therapeutic agent is prevented, treated or delayed. The present method can be used for preventing, treating or delaying cardiac toxicity in any mammals, such as mice, rats, rabbits, cats, dogs, pigs, cows, ox, sheep, goats, horses, monkeys and other non-human primates. Preferably, the present method is used for preventing, treating or delaying cardiac toxicity in humans.

1. Neuregulin Agents

Any suitable neuregulin protein or a functional fragment thereof, or a nucleic acid encoding a neuregulin protein or a functional fragment thereof, can be used in the present methods. In one embodiment, the methods of the present invention uses a polypeptide fragment of a human neuregulin β 2 isomer, which contains the receptor-binding domain (i.e., an EGF-class region). This polypeptide can activate the erbB receptor of the EGF receptor family and modulate its biological reactions (e.g., stimulate breast cancer cell differentiation and milk protein secretion; induce the differentiation of neural crest cell into Schwann cell; stimulate acetylcholine synthesis in skeletal muscle cell; and/or improve cardiocyte survival and DNA synthesis). Neuregulin nucleic acids and proteins can be produced by any suitable methods known in the art, including but not limited to recombinant production, chemical synthesis or a combination of both. Preferably, neuregulin nucleic acids and proteins are produced by recombinant production. (See, Ausubel et al., Current Protocols in Molecular Biology, John Wiley & Sons, Inc. 2002).

Neuregulin variants with conservative amino acid substitutions that do not substantially alter their anti-cardiotoxic activity can also be used in the present methods. Suitable conservative substitutions of amino acids are known to those of skill in this art, and may be made generally without altering the biological activity of the resulting molecule. Those of skill in this art recognize that, in general, single amino acid substitutions in non-essential regions of a polypeptide do not substantially alter biological activity (see e.g., Watson et al. *Molecular Biology of the Gene*, 4th Edition, page 224, The Benjamin/Cummings Pub. Co., 1987).

The nucleic acid encoding a neuregulin protein or a functional fragment thereof, can be used in the form of naked DNA, complexed DNA, cDNA, plasmid DNA, RNA or other mixtures thereof as components of the gene delivery system. In another embodiment, the nucleic acid encoding a neuregulin protein or a functional fragment thereof, is included in a viral vector. Any viral vectors that are suitable for gene therapy can be used. Non-limiting examples include adenovirus vectors (U.S. Pat. No. 5,869,305), simian virus vectors (U.S. Pat. No.5,962,274), conditionally replicating human immunodeficiency viral vectors (U.S. Pat. No. 5,888,767), retroviruses, SV40, herpes simplex viral amplicon vectors, and vaccinia virus vectors. In addition, the genes can be delivered in a non-viral vector system such as a liposome wherein the lipid protects the DNA or other biomaterials from oxidation during the coagulation.

In a specific embodiment, the neuregulin used in the present methods carries out its anti-cardiotoxic activity via binding with any of the erbB2-erbB4 receptors. In another specific embodiment, neuregulin 1, neuregulin 2, neuregulin 3 or neuregulin 4 is used in the present methods. Synonyms of neuregulin 1 include heregulin, GGF2 and p185erbB2 ligand. (See e.g., WO 00/64400 and U.S. Pat. Nos. 5,530,109 and 5,716,930). Both neuregulin α2 and neuregulin β2 can be used in the present methods. Preferably, a neuregulin β2 fragment comprising an amino acid sequence set forth in SEQ ID NO:4 is used in the present methods.

In still another specific embodiments, neuregulins or functional fragments thereof disclosed in the following patents, patent applications and GenBank databases can be used in the present methods: U.S. Pat. Nos. 6,252,051 and 6,121,415 (NRG3); U.S. Pat. No. 6,087,323 (neuregulin with p185$^{erbB2}$, p185$^{erbB3}$ or p185$^{erbB4}$ binding activity); U.S. Pat. No. 6,033,906 (neuregulin as a ligand for a receptor selected from the group consisting of p185$^{erbB2}$ and p180$^{erbB4}$); US2002002276 (chimeric ErbB heteromultimer adhesins as competitive antagonists or agonists of a neuregulin); WO01/81540 (NRG-4); WO01/64877 (NRG1); WO01/64876 (NRG1AG1); WO01/58948 (neuregulin-beta); WO01/26607 (SMDF and GGF neuregulin splice variant isoforms); WO00/70322 (CRD-neuregulin); WO00/64400; WO99/18976; WO98/02540 (chimeric ErbB heteromultimer adhesins as competitive antagonists or agonists of a neuregulin); WO96/30403; WO96/15812; BC017568 (*Homo sapiens*, Similar to neuregulin 4); BC007675 (*Homo sapiens*, neuregulin 1); AF142632 (*Xenopus laevis* cysteine-rich domain neuregulin-1); AF194439 (*Rattus norvegicus* SMDF neuregulin alpha 2a (Nrg1)); AF194438 (*Rattus norvegicus* SMDF neuregulin beta 1a (Nrg1)); HS2NRG12 (*Homo sapiens* alternatively spliced neuregulin 2 (NRG2)); HS2NRG08 (*Homo sapiens* alternatively spliced neuregulin 2 (NRG2)); HS2NRG07 (*Homo sapiens* alternatively spliced neuregulin 2 (NRG2)); AF083067 (*Mus musculus* neuregulin-4 short isoform (Nrg4)); AF076618 (*Xenopus laevis* neuregulin alpha-1); AF045656 (*Gallus gallus* neuregulin beta-2b); AF045655 (*Gallus gallus* neuregulin beta-2a); AF045654 (*Gallus gallus* neuregulin beta-1a); MAU96612 (*Mesocricetus auratus* neuregulin); AF010130 (*Mus musculus* neuregulin-3 (NRG3)). Preferably, neuregulin(s) disclosed in the GenBank Accession No. NT_007995 (gi: 18570363) is used in the present methods.

2. Prophylactic or Therapeutic Agents

The present invention provides methods for preventing, treating or delaying cardiac toxicity associated with the administration of a prophylactic or therapeutic agent. The neuregulin agent can be administered prior to, concurrently with, or subsequent to the administration of the prophylactic or therapeutic agent. The present methods are not limited to preventing, treating or delaying cardiac toxicity associated with specific prophylactic or therapeutic agents. Non-limiting examples of prophylactic or therapeutic agents for use in the present methods include anti-neoplasm agents, antipsychotic agents, tricyclic depressants, interferons, interleukins, and anti-infectious agents. Any anti-neoplasm agent can be used in the present methods. Preferably, the anti-neoplasm agent is an anthracyline anti-neoplasm agent having the formula:

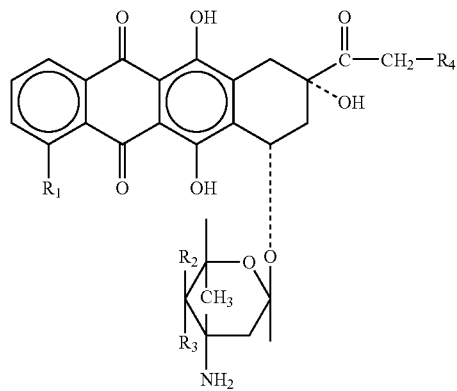

wherein R1 is methoxy or hydrogen; and R2, R3 and R4 are hydroxy or hydrogen.

Non-limiting examples of anthracycline anti-neoplasm agent include adriamycin (or doxorubicin), daunorubicin, epirubicin, idarubicin, mitoxantrone, mitomycin, bleomycin, cyclophosphamide, fluorouracil, actinomycin D, vincristine, and derivatives thereof. (See Goodman & Gilman's, The Pharmacological Basis of Therapeutics, Ninth Edition, pp. 1264-1269, McGraw-Hill 1996). Other examples of anti-neoplasm agents that can be used in the present methods are described in U.S. patent application No. 2002/044919. Other anti-neoplasm agents include, but are not limited to, cytidine, arabinosyladenine (araC), daunomycin, methotrexate (MTX), fluorinated pyrimidines such as 5-fluorouracil (5-FU), hydroxyurea, 6-mercaptopurine, plant alkaloids such as vincristine (VCR), VP-16 and vinblastine (VLB), alkylating agent, cisplatin, nitrogen Mustard, trisamine, procarbazine, bleomycin, mitomycin C, actinomycin D, or an enzyme such as L-Asparaginase. (See Goodman & Gilman's, The Pharmacological Basis of Therapeutics, Ninth Edition, pp. 1227-1229).

Any antipsychotic agent can be used in the present methods. Non-limiting examples of antipsychotic agents include chlorpromazine, perphenazine and trifluperazine. Other examples of antipsychotic agents can be found in Goodman & Gilman's, The Pharmacological Basis of Therapeutics, Ninth Edition, pp. 400-420.

Any tricyclic antidepressant can be used in the present methods. Non-limiting examples of tricyclic antidepressants include chlorimipramine, amitriptyline and doxepin. Other examples of antipsychotic agents can be found in Goodman & Gilman's, The Pharmacological Basis of Therapeutics, Ninth Edition, pp. 431-434.

Any interferon can be used in the present methods. Preferably, the interferon is interferon-α. In one embodiment, the interferon is human interferon-α. Methods for producing interferon-α can be found in U.S. Pat. Nos. 6,005,075; 5,834,235; 5,503,828; and 4,820,638.

Any interleukin can be used in the present methods. Preferably, the interleukin is interleukin-2. In one embodiment, the interleukin is human interleukin-2. Methods for producing interleukin-2 can be found in U.S. Pat. Nos. 5,834,441; 5,795,777; 5,419,899; and 5,399,699.

Any anti-infectious agent can be used in the present methods. Preferably, the anti-infectious agent is emetine. Other examples of anti-infectious agent can be found in Goodman & Gilman's, The Pharmacological Basis of Therapeutics, Ninth Edition, pp. 965-1008.

Neuregulin agents can be administered in vivo (i.e., administered directly into a mammal). Alternatively, the neuregulin protein or a functional fragment thereof, or a nucleic acid encoding a neuregulin protein or a functional fragment thereof, can be administered ex vivo (i.e., administered into cells, tissues or organs, wherein such cells, tissues or organs carrying the neuregulin protein, or a functional fragment thereof, or a nucleic acid encoding a neuregulin protein, or a functional fragment thereof, can be transferred into a mammal).

E. Treating Myocardial Infarction

In one aspect, the present invention is directed to a combination, which combination comprises an effective amount of a neuregulin protein, or a functional fragment thereof, or a nucleic acid encoding a neuregulin protein, or a functional fragment thereof, or an agent that enhances production and/or function of said neuregulin, and an effective amount of a prophylactic or therapeutic agent for myocardial infarction.

Preferably, the present combinations further comprise a pharmaceutically acceptable carrier or excipient.

Any suitable neuregulin can be used in the present combinations. For example, the neuregulin used in the present combinations can carry out its anti-myocardial infarction activity via binding with ErbB2-ErbB4 receptors. In another example, the neuregulin used in the present combinations is neuregulin 1, neuregulin 2, neuregulin 3 or neuregulin 4. Preferably, the neuregulin 2 is neuregulin α2 or neuregulin β2. In still another example, the neuregulin used in the present combinations is a neuregulin β2 fragment comprising an amino acid sequence set forth in SEQ ID NO:4. Any specific neuregulin described in the above sections can also be used.

Any suitable prophylactic or therapeutic agent can be used in the present combinations. For example, the prophylactic or therapeutic agent used in the present combinations can be an angiotensin I-converting enzyme inhibitor (ACEI), a calcium antagonist, a β-receptor antagonist, aspirin, atropine, nitroglycerin, scopolamine or a thrombolytic agent.

Any suitable ACEI can be used. Exemplary ACEIs include Captopril, Rampril, Lisinopril, Zofenopril and Trandolapril. Any suitable calcium antagonist can be used. Exemplary calcium antagonists include diltiazem. Any suitable β-receptor antagonist can be used. Exemplary β-receptor antagonists include propranolol, metoprolol, atenolol and timolol. Any suitable thrombolytic agent can be used. Exemplary thrombolytic agents include streptokinase, t-PA and anistreplase.

In another aspect, the present invention is directed to a kit, which kit comprises an above-described combination in a container and an instruction for using said combination in preventing, treating or delaying myocardial infarction.

In still another aspect, the present invention is directed to a method for preventing, treating or delaying myocardial infarction in a mammal, which method comprises administering to a mammal, to which such prevention, treatment or delay is needed or desirable, an effective amount of a neuregulin protein, or a functional fragment thereof, or a nucleic acid encoding a neuregulin protein, or a functional fragment thereof, or an agent that enhances production and/or function of said neuregulin, whereby said myocardial infarction is prevented, treated or delayed.

Any suitable neuregulin can be used in the present methods. For example, the neuregulin used in the present methods can carry out its anti-myocardial infarction activity via binding with ErbB2-ErbB4 receptors. In another example, the neuregulin used in the present methods is neuregulin 1, neuregulin 2, neuregulin 3 or neuregulin 4. Preferably, the neuregulin 2 is neuregulin α2 or neuregulin β2. In still another example, the neuregulin used in the present methods is a neuregulin β2 fragment comprising an amino acid sequence set forth in SEQ ID NO:4. Any specific neuregulin described in the above sections can also be used.

In a specific embodiment, the neuregulin protein, or a functional fragment thereof, the nucleic acid encoding a neuregulin protein, or a functional fragment thereof, or the agent that enhances production and/or function of the neuregulin antagonizes the increase of left ventricular end-diastolic (LVEDD) and end-systolic diameters (LVESD) associated with the myocardial infarction. In another specific embodiment, the neuregulin protein, or a functional fragment thereof, the nucleic acid encoding a neuregulin protein, or a functional fragment thereof, or the agent that enhances production and/or function of the neuregulin antagonizes the decrease of left ventricular EF associated with the myocardial infarction.

The present methods can be used to prevent, treat or delay myocardial infarction in any suitable mammal. Exemplary mammals include mice, rats, rabbits, cats, dogs, pigs, cows, ox, sheep, goats, horses, monkeys and other non-human primates. Preferably, the present methods are used to prevent, treat or delay myocardial infarction in a human.

The present methods can be used to prevent, treat or delay any suitable myocardial infarction. For example, the present methods can be used to prevent, treat or delay myocardial infarction having a clinical feature selected from the group consisting of left ventricular dilation, reduced systolic function and increased filling pressure.

The neuregulin protein, or a functional fragment thereof, or a nucleic acid encoding a neuregulin protein, or a functional fragment thereof, or the agent that enhances production and/or function of the neuregulin, can be administered alone. Preferably, the neuregulin protein, or a functional fragment thereof, or a nucleic acid encoding a neuregulin protein, or a functional fragment thereof, or the agent that enhances production and/or function of the neuregulin, is administered with a pharmaceutically acceptable carrier or excipient. In a specific embodiment, a neuregulin protein, or a functional fragment thereof, is administered. In another embodiment, a nucleic acid encoding a neuregulin protein, or a functional fragment thereof, is administered. Any suitable route of administration can be used. Preferably, intravenous administration is used.

The present methods can further comprise administering a prophylactic or therapeutic agent for myocardial infarction. Any suitable prophylactic or therapeutic agent can be used in the present methods. For example, the prophylactic or therapeutic agent used in the present methods can be an angiotensin I-converting enzyme inhibitor (ACEI), a calcium antagonist, a β-receptor antagonist, aspirin, atropine, nitroglycerin, scopolamine or a thrombolytic agent.

Any suitable ACEI can be used. Exemplary ACEIs include Captopril, Rampril, Lisinopril, Zofenopril and Trandolapril. Any suitable calcium antagonist can be used. Exemplary calcium antagonists include diltiazem. Any suitable β-receptor antagonist can be used. Exemplary β-receptor antagonists include propranolol, metoprolol, atenolol and timolol. Any suitable thrombolytic agent can be used. Exemplary thrombolytic agents include streptokinase, t-PA and anistreplase.

In a preferred embodiment, the neuregulin protein, or a functional fragment thereof, the nucleic acid encoding a neuregulin protein, or a functional fragment thereof, or the agent that enhances production and/or function of the neuregulin is administered in vivo.

F. Pharmaceutical Compositions with Preferred Safety Dosage and/or Regimen

In one aspect, the present invention is directed to a pharmaceutical composition for preventing, treating or delaying a disease in a mammal, which composition comprises a neuregulin protein, or a functional fragment thereof: a) in a safety dosage equals to or less than about 170 U/kg; or b) in a total regimen equals to or less than about 3,600 U/kg.

The present pharmaceutical compositions can be used in any suitable regimen and/or administration plans. In one example, the present pharmaceutical compositions are administered for about 21 days or less than 21 days. In another example, the present pharmaceutical compositions are administered continuously or intermittently.

The present pharmaceutical compositions can be administered alone. Preferably, the present pharmaceutical compositions can further comprise a pharmaceutically acceptable carrier or excipient.

Any suitable neuregulin can be used in the present pharmaceutical compositions. For example, the neuregulin used in the present pharmaceutical compositions can carry out its anti-disease activity via binding with ErbB2-ErbB4 receptors. In another example, the neuregulin used in the present pharmaceutical compositions is neuregulin 1, neuregulin 2, neuregulin 3 or neuregulin 4. Preferably, the neuregulin 1 is neuregulin α2 or neuregulin β2. In still another example, the neuregulin used in the present pharmaceutical compositions is a neuregulin β2 fragment comprising an amino acid sequence set forth in SEQ ID NO:4. Any specific neuregulin described in the above sections can also be used.

The present pharmaceutical compositions can be used to prevent, treat or delay a disease in any suitable mammal. Exemplary mammals include mice, rats, rabbits, cats, dogs, pigs, cows, ox, sheep, goats, horses, monkeys and other non-human primates. Preferably, the present methods are used to prevent, treat or delay a disease in a human.

The present pharmaceutical compositions can be used to prevent, treat or delay any suitable disease. Preferably, the present pharmaceutical compositions are used to prevent, treat or delay a cardiovascular disease, e.g., viral myocarditis, DCM, cardiotoxic activity, myocardial infarction activity, etc.

In a preferred embodiment, the present pharmaceutical compositions are formulated for intravenous administration.

The following is an exemplary, rapid, sensitive, high flux and quantitative method for determination of biological activity of NRG-1 through combining Neuregulin with cell surface ErbB3/ErbB4 molecule and indirect mediation of ErbB2 protein phosphorylation (See e.g., Michael D.Sadick et al. Analytical Biochemistry, 1996, 235, 207-214). According to the practical example 3 of the in vitro NRG-1 activity determination as described in Michael D. Sadick et al., NGR-1 biological activity of various origins can be determined.

Briefly, the assay, termed a kinase receptor activation enzyme-linked immunosorbant assay (KIRA-ELISA), consists of two separate microtiter plates, one for cell culture, ligand stimulation, and cell lysis/receptor solubilization and the other plate for receptor capture and phosphotyrosine ELISA. The assay was developed for analysis of heregulin-induced ErbB2 activation and utilizes the stimulation of intact receptor on the adherent breast carcinoma cell line, MCF-7. Membrane proteins are solubilized via Triton X-100 lysis and the receptor is captured in ELISA wells coated with ErbB2-specific antibodies with no cross-reaction to ErbB3 or ErbB4. The degree of receptor phosphorylation is then quantified by antiphosphotyrosine ELISA. A reproducible standard curve is generated with a EC(50) of approximately 360 pM for heregulin beta 1(177-244) (HRG beta 1(177-244). When identical samples of HRG beta 1(177-244) are analyzed by both the KIRA-ELISA and quantitative antiphosphotyrosine Western blot analysis, the results correlate very closely with one another. The assay described in this report is able to specifically quantify tyrosine phosphorylation of ErbB2 that results from the interaction of HRG with ErbB3 and/or ErbB4.

Since most of the genetically engineered medicines are proteins and polypeptides, their activity can be determined by their amino acid sequences or the activity center formed by their spatial structure. Activity titer of protein and polypeptide is not consistent with their absolute quality, therefore cannot be determined with weight unit as that of chemical drugs. However, biological activity of genetically engineered medicines is generally consistent with their pharmacodynamics and titer determination system established through given biological activity can determine its titer unit. Therefore, biological activity determination can be part of a process of titering the substance with biological activity and is an important component of quality control of genetically engineered product. It is important to determine biological activity criteria for quality control of genetically engineered product and clinically used drugs.

Quantity of standard product that can induce 50% maximal reaction is defined as an activity unit (1 U). Accordingly, product from different pharmaceuticals and of different batch number can be quantitated with uniform criteria.

G. The Formulation, Dosage and Route of Administration of Neuregulin

The formulation, dosage and route of administration of a neuregulin protein, or a functional fragment thereof, or a nucleic acid encoding a neuregulin protein, or a functional fragment thereof, preferably in the form of pharmaceutical compositions, can be determined according to the methods known in the art (see e.g., *Remington: The Science and Practice of Pharmacy*, Alfonso R. Gennaro (Editor) Mack Publishing Company, April 1997; *Therapeutic Peptides and Proteins: Formulation, Processing, and Delivery Systems*, Banga, 1999; and *Pharmaceutical Formulation Development of Peptides and Proteins*, Hovgaard and Frkjr (Ed.), Taylor & Francis, Inc., 2000; *Medical Applications of Liposomes*, Lasic and Papahadjopoulos (Ed.), Elsevier Science, 1998; *Textbook of Gene Therapy*, Jain, Hogrefe & Huber Publishers, 1998; *Adenoviruses: Basic Biology to Gene Therapy*, Vol. 15, Seth, Landes Bioscience, 1999; *Biopharmaceutical Drug Design and Development*, Wu-Pong and Rojanasakul (Ed.), Humana Press, 1999; *Therapeutic Angiogenesis: From Basic Science to the Clinic*, Vol. 28, Dole et al. (Ed.), Springer-Verlag New York, 1999). The neuregulin protein, or a functional fragment thereof, or a nucleic acid encoding the neuregulin protein, or a functional fragment thereof, can be formulated for oral, rectal, topical, inhalational, buccal (e.g., sublingual), parenteral (e.g., subcutaneous, intramuscular, intradermal, or intravenous), transdermal administration or any other suitable route of administration. The most suitable route in any given case will depend on the nature and severity of the condition being treated and on the nature of the particular neuregulin protein, or a functional fragment thereof, or a nucleic acid encoding the neuregulin protein, or a functional fragment thereof, which is being used.

The neuregulin protein, or a functional fragment thereof, or a nucleic acid encoding the neuregulin protein, or a functional fragment thereof, can be administered alone. Alternatively and preferably, the neuregulin protein, or a functional fragment thereof, or a nucleic acid encoding the neuregulin protein, or a functional fragment thereof, is co-administered with a pharmaceutically acceptable carrier or excipient. Any suitable pharmaceutically acceptable carrier or excipient can be used in the present method (See e.g., *Remington: The Science and Practice of Pharmacy*, Alfonso R. Gennaro (Editor) Mack Publishing Company, April 1997).

The nucleic acid encoding a neuregulin protein, or a functional fragment thereof, can be used in the form of naked DNA, complexed DNA, cDNA, plasmid DNA, RNA or other mixtures thereof as components of the gene delivery system. In another embodiment, the nucleic acid encoding a neuregulin protein, or a functional fragment thereof, is included in a viral vector. Any viral vectors that are suitable for gene therapy can be used. For example, an adenovirus vector (U.S. Pat. No. 5,869,305), a simian virus vector (U.S. Pat. No. 5,962,274), a conditionally replicating human immunodeficiency viral vector (U.S. Pat. No. 5,888,767), retrovirus, SV40, Herpes simplex viral amplicon vectors and Vaccinia virus vectors can be used. In addition, the genes can be delivered in a non-viral vector system such as a liposome wherein the lipid protects the DNA or other biomaterials from oxidation during the coagulation.

According to the present invention, the neuregulin protein, or a functional fragment thereof, or a nucleic acid encoding the neuregulin protein, or a functional fragment thereof, alone or in combination with other agents, carriers or excipients, may be formulated for any suitable administration route, such as intracavemous injection, subcutaneous injection, intravenous injection, intramuscular injection, intradermal injection, oral or topical administration. The method may employ formulations for injectable administration in unit dosage form, in ampoules or in multidose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, sterile pyrogen-free water or other solvents, before use. Topical administration in the present invention may employ the use of a foam, gel, cream, ointment, transdermal patch, or paste.

Pharmaceutically acceptable compositions and methods for their administration that may be employed for use in this invention include, but are not limited to those described in U.S. Pat. Nos. 5,736,154; 6,197,801 B1; 5,741,511; 5,886,039; 5,941,868; 6,258,374 B1; and 5,686,102.

The magnitude of a therapeutic dose in the treatment or prevention will vary with the severity of the condition to be treated and the route of administration. The dose, and perhaps dose frequency, will also vary according to age, body weight, condition and response of the individual patient.

It should be noted that the attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

Any suitable route of administration may be used. Dosage forms include tablets, troches, cachet, dispersions, suspensions, solutions, capsules, patches, and the like. See, Remington's Pharmaceutical Sciences.

In practical use, the neuregulin protein, or a functional fragment thereof, or a nucleic acid encoding the neuregulin protein, or a functional fragment thereof, alone or in combination with other agents, may be combined as the active in intimate admixture with a pharmaceutical carrier or excipient, such as beta-cyclodextrin and 2-hydroxy-propyl-beta-cyclodextrin, according to conventional pharmaceutical compounding techniques. The carrier may take a wide form of preparation desired for administration, topical or parenteral. In preparing compositions for parenteral dosage form, such as intravenous injection or infusion, similar pharmaceutical media may be employed, water, glycols, oils, buffers, sugar, preservatives, liposomes, and the like known to those of skill in the art. Examples of such parenteral compositions include, but are not limited to dextrose 5% w/v, normal saline or other solutions. The total dose of the neuregulin protein, or a functional fragment thereof, or a nucleic acid encoding the neuregulin protein, or a functional fragment thereof, alone or in combination with other agents to be administered may be administered in a vial of intravenous fluid, ranging from about 1 ml to 2000 ml. The volume of dilution fluid will vary according to the total dose administered.

The invention also provides for kits for carrying out the therapeutic regimens of the invention. Such kits comprise in one or more containers therapeutically effective amounts of the neuregulin protein, or a functional fragment thereof, or a nucleic acid encoding the neuregulin protein, or a functional fragment thereof, alone or in combination with other agents, in pharmaceutically acceptable form. Preferred pharmaceutical forms would be in combination with sterile saline, dextrose solution, or buffered solution, or other pharmaceutically acceptable sterile fluid. Alternatively, the composition may be lyophilized or dessicated; in this instance, the kit optionally further comprises in a container a pharmaceutically acceptable solution, preferably sterile, to reconstitute the complex to form a solution for injection purposes. Exemplary pharmaceutically acceptable solutions are saline and dextrose solution.

In another embodiment, a kit of the invention further comprises a needle or syringe, preferably packaged in sterile form, for injecting the composition, and/or a packaged alcohol pad. Instructions are optionally included for administration of composition by a physician or by the patient.

H. EXAMPLES

Recombinant Human Neuregulin-1 $\beta_{S177-Q237}$ (rhNRG-1 $\beta_{S177-Q237}$ of Neuregulin-1) developed by the present inventor can repair damaged myocardial cell structure, strengthen connection between these cells, improve myocardial function and strengthen myocardial biological effect. The experiments described herein demonstrate that certain Neuregulin fragments, e.g., rhNRG-1 $\beta_{S177-Q237}$, can effectively treat various forms of cardiovascular disease such as viral myocarditis or dilated (congestive) cardiomyopathy (DCM), cardiotoxic caused by certain therapeutic agents, or myocardial infarction in vivo and do not affect hemodynamics of normal animals.

Example 1

Recombinant Production of rhNRG-1 $\beta_{S177-Q237}$

FIG. 1. Technical Outline of Construction of an Engineered Strain

Human neuregulin gene is located in chromosome 8P12 with about 13 exons. Recombinant neuregulin fragment is composed of 61 amino acid. Theoretical molecular weight is 7,055 D. Apparent molecular weight in SDS-PAGE electrophoresis is 6,500-7,000 D. Its isoelectric point is about 6.5. There is no glycosylated locus. The peptide structure contains 3 disulfide bonds. This gene is suitable for expression in *E. coli*.

PET22b was selected as expression plasmid. Human neuregulin gene was introduced into the plasmid and then *E. coli* BL21 was transformed by this plasmid. High level expression recombinant was screened out as engineered strain for producing recombinant human neuregulin fragment.

Figure 2:
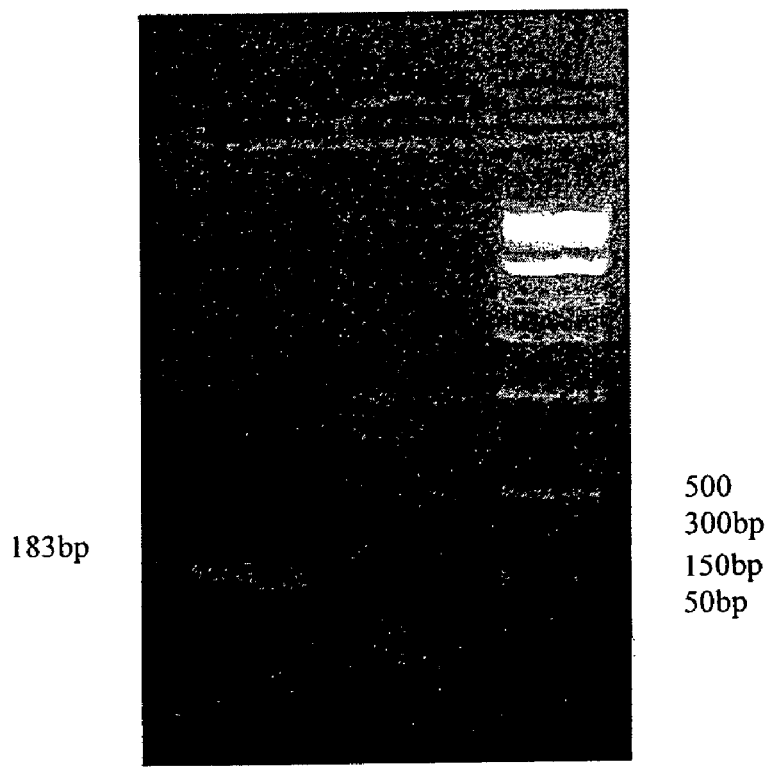
FIG. 2 depicts PCR amplification of human neuregulin gene. Lane 1: 183 bp neuregulin gene obtained by RT-PCR; and Lanes 2 and 3: DNA markers.

FIG. 2. Amplification of Human Neuregulin Gene

Total RNA and mRNA were extracted from brain tissue of 5-month human fetus and reversibly transcribed to cDNA. RT-PCR was performed with the transcribed cDNA as template, and a pair of primers P1, TCG AAC ATA TGA GCC ATC TTG TAA AAT GTG CGG (SEQ ID NO:1) and P2, TCG AAG GGC CCT CAC TGG TAC AGC TCC TCC (SEQ ID NO:2) to amplify target gene. The PCR product was examined in electrophoresis on 1.5% agarose. Specific 183 bp DNA fragment was found in agarose, the length of which was the same as anticipated.

Figure 3:
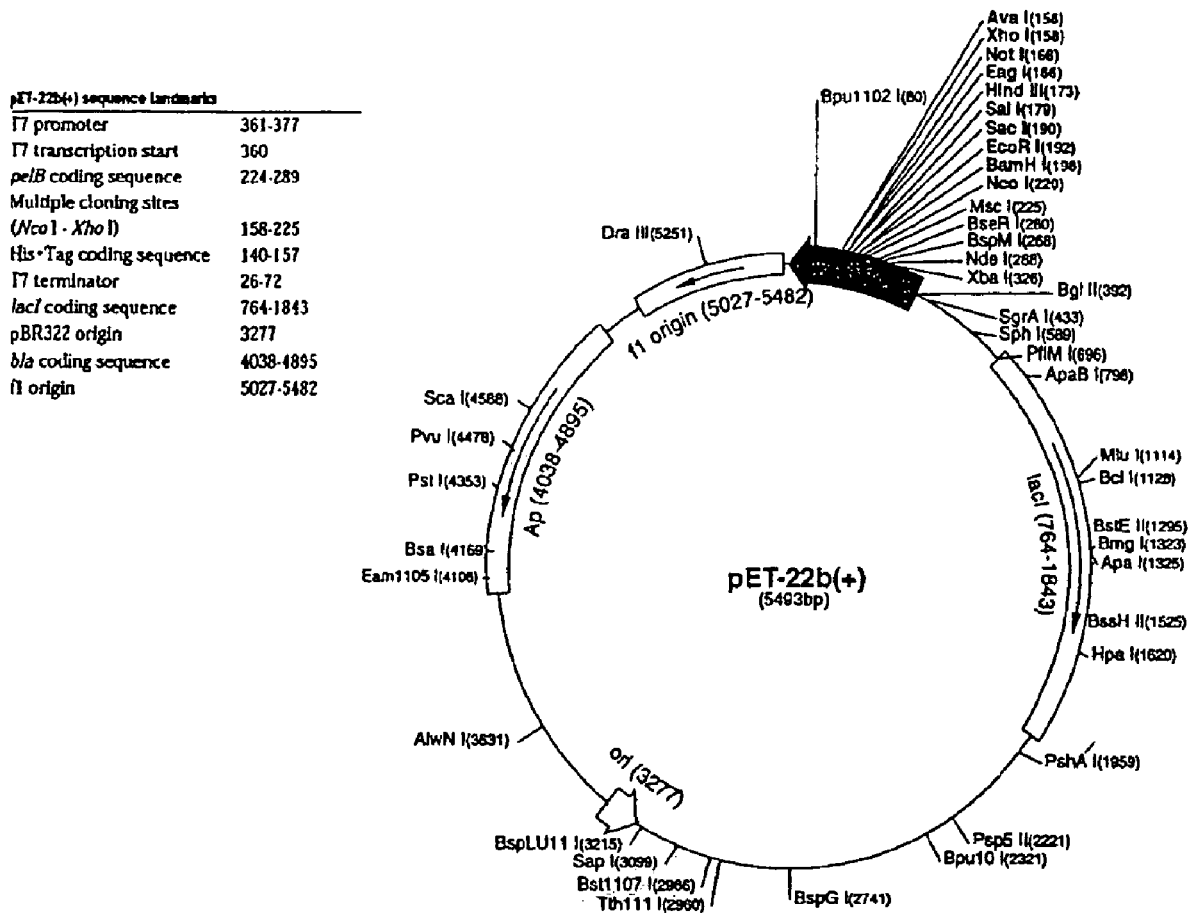
FIG. 3 depicts physical map of plasmid PET22b.

FIG. 3. Physical Map of Plasmid PET22b

FIG. 3 is an illustration of Physical map of plasmid PET22b.

Figure 4:
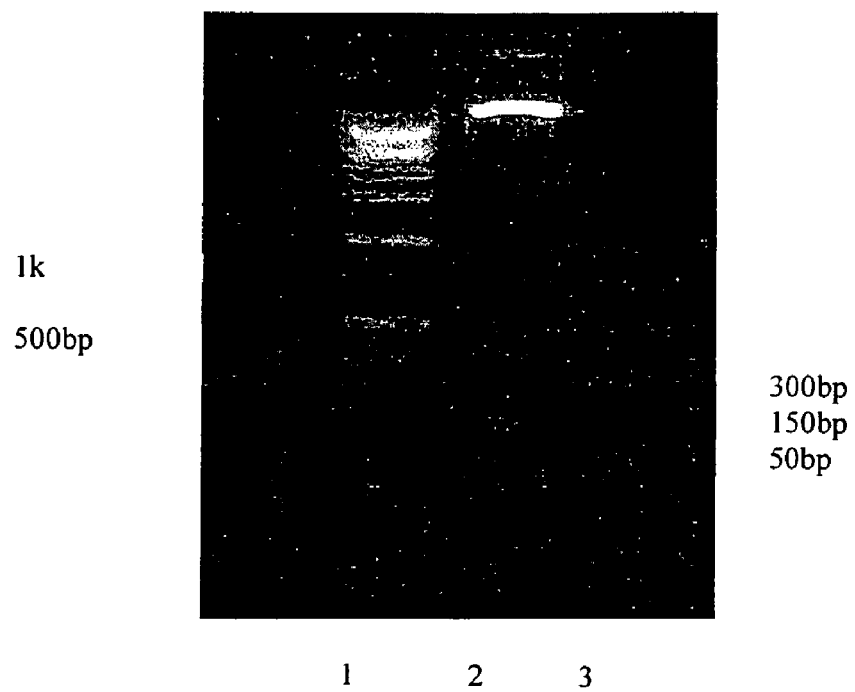
FIG. 4 depicts identification of recombinant plasmid by endonuclease digestion. Lanes 1 and 3: DNA marker; and lane 2: fragments after enzyme digestion.

FIG. 4. Identification of Recombinant Plasmid by Endonuclease Digestion

Calcium chloride sedimentation method was applied to clone human neuregulin gene into the expression plasmid PET22b to construct recombinant human neuregulin expression plasmid (PET22b-human neuregulin). This gene was expressed efficiently under the drive of T7 promoter. N-terminal of expressed gene was inserted at NdeI locus. C-terminal terminator is next to the last amino acid. The expressed protein did not form fusion protein with any amino acid. An accurate 183 bp fragment was obtained after endonuclease digestion analysis. Transformant was characterized by endonuclease digestion. Double-stranded DNA was extracted for sequence analysis. The sequencing results confirmed that the sequence of human neuregulin carried in expression vector was completely correct. The determined cDNA sequence is listed here: AGC CAT CTT GTA AAA TGT GCG GAG AAG GAG AAA ACT TTC TGT GTG AAT GGA GGG GAG TGC TTC ATG GTG AAA GAC CTT TCA AAC CCC TCG AGA TAC TTG TGC AAG TGC CCA AAT GAG TTT ACT GGT GAT CGC TGC CAA AAC TAC GTA ATG GCC AGC TTC TAC AAG GCG GAG GAG CTG TAC CAG (SEQ ID NO:3). The deduced amino acid sequence based on the above cDNA sequence is: SHLVKCAEKEKTFCVNGGECFMVKDLSNPSRYLCKCPNEFTGDRCQNYVMASF YKAEELYQ (SEQ ID NO:4).

Figure 5:
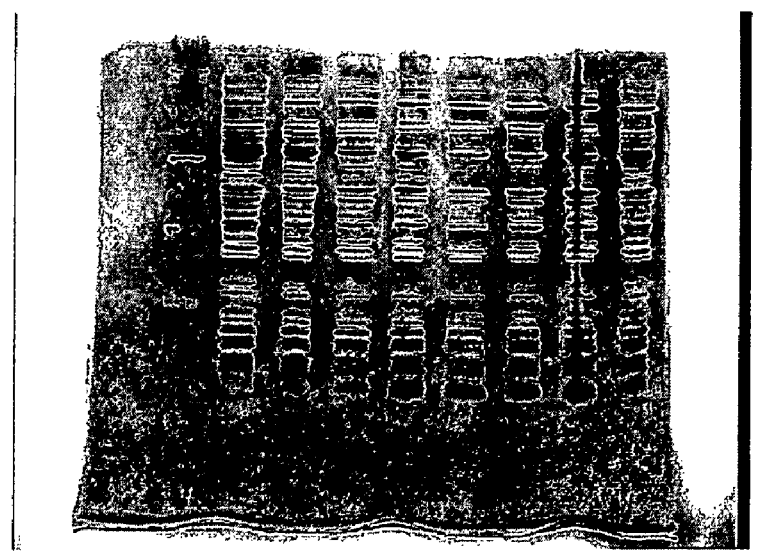
FIG. 5 depicts screening for expression of an engineered strain. Lane 1: Marker; lane 2: engineered strain without induction; lane 3: 1 hour after induction; lane 4: 2 hours after induction; lane 5: 3 hours after induction; lane 6: 4 hours after induction; and lanes 7-9: different strains with induction.
Figure 6:
FIG. 6 depicts pathologic section of myocardial tissue in pseudo-operation group rat (1)(10×10), showing that there was no specific pathological change.
Figure 7:
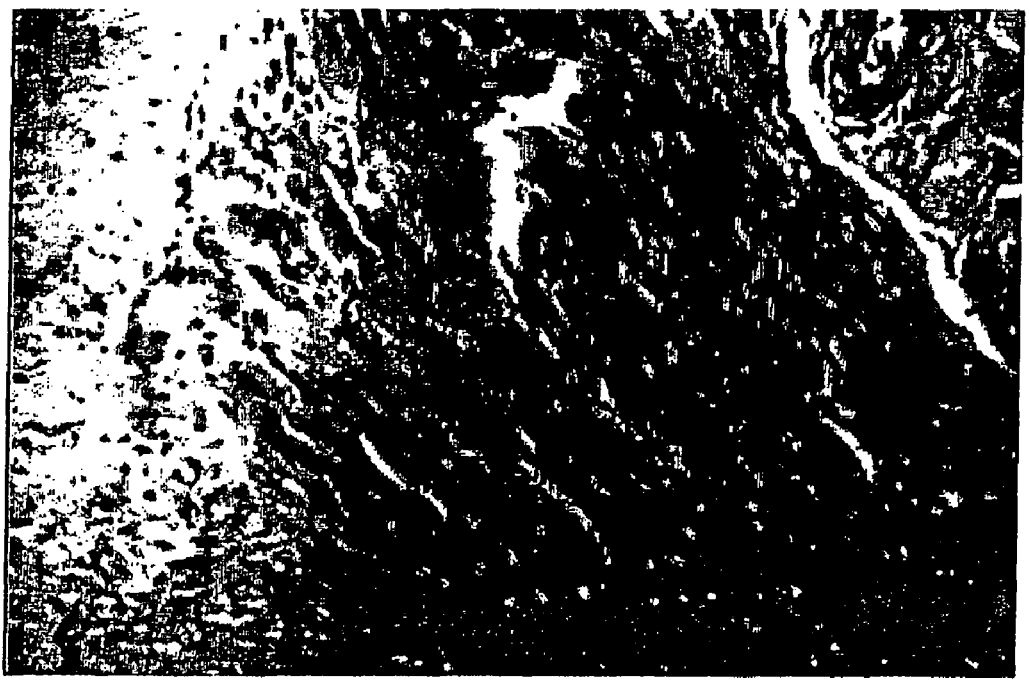
FIG. 7 depicts large area of red stained region in the model group (10×10).
Figure 8:
FIG. 8 illustrates sporadic distribution of red stained myocardial cells of the rhNRG-1 β group (20 μg/kg) (I) (10×10).
Figure 9:
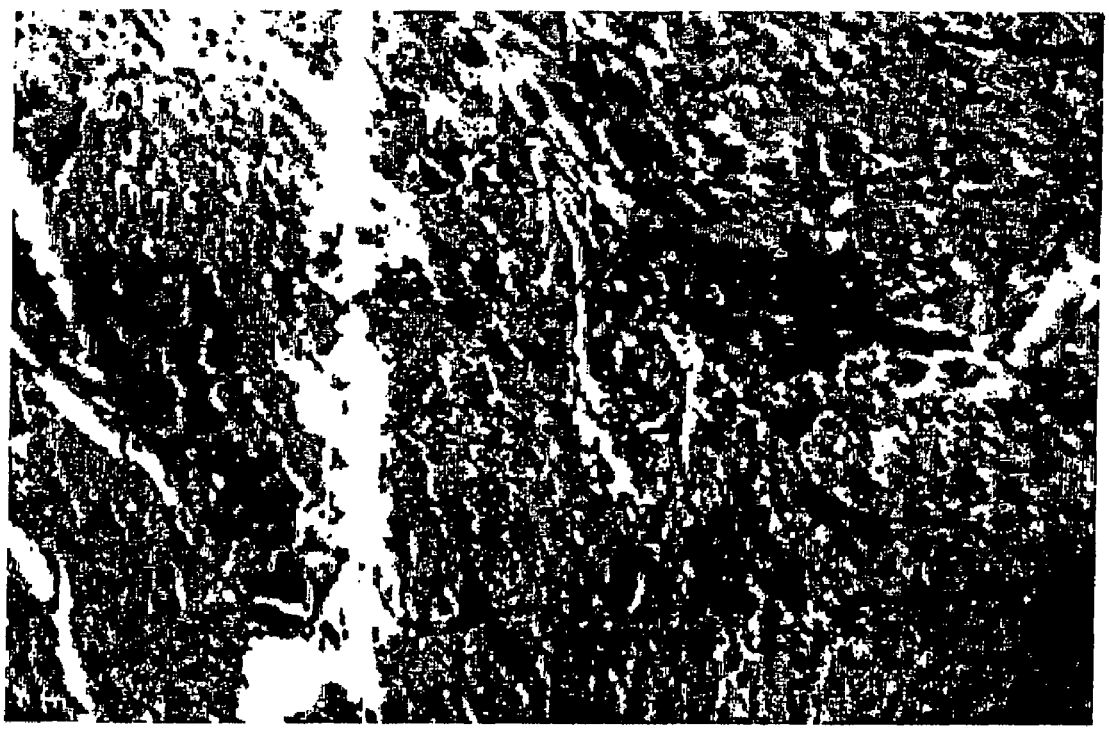
FIG. 9 illustrates patchy distribution of red stained myocardial cells and connective tissue of the medium dosage (10 μg/kg) of rhNRG-1 β group (I) (10×10).
Figure 10:
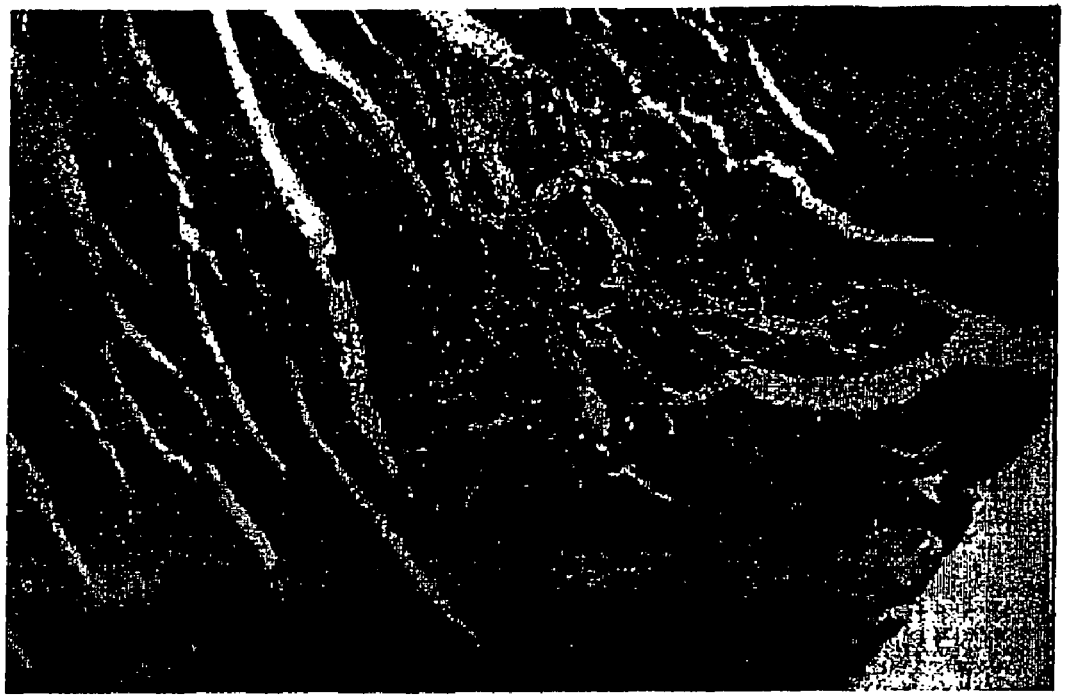
FIG. 10 illustrates patchy distribution of red stained myocardial cells and connective tissue of the low dosage (5 μg/kg) of rhNRG-1 β group (I) (10×10).
Figure 11:
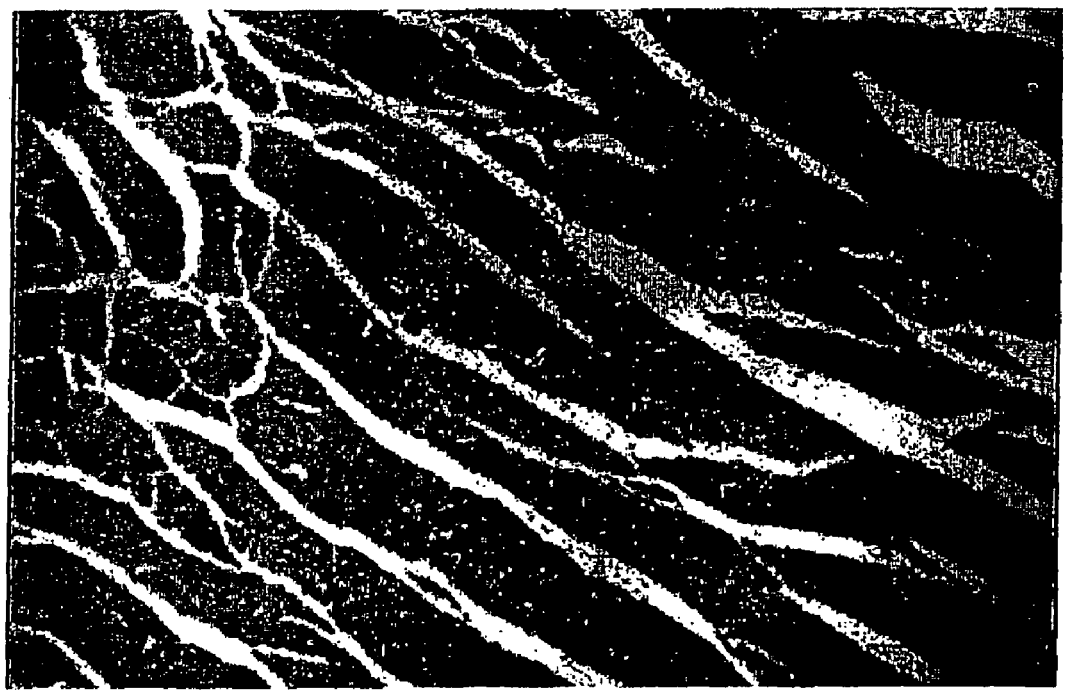
FIG. 11 depicts pathohistologic section of myocardial tissue in pseudo-operation group (II) (10×10), showing that there was no specific pathologic changes of the myocardial tissue.
Figure 12:
FIG. 12 depicts large area of red stained region was seen in the model group (II) (10×10).
Figure 13:
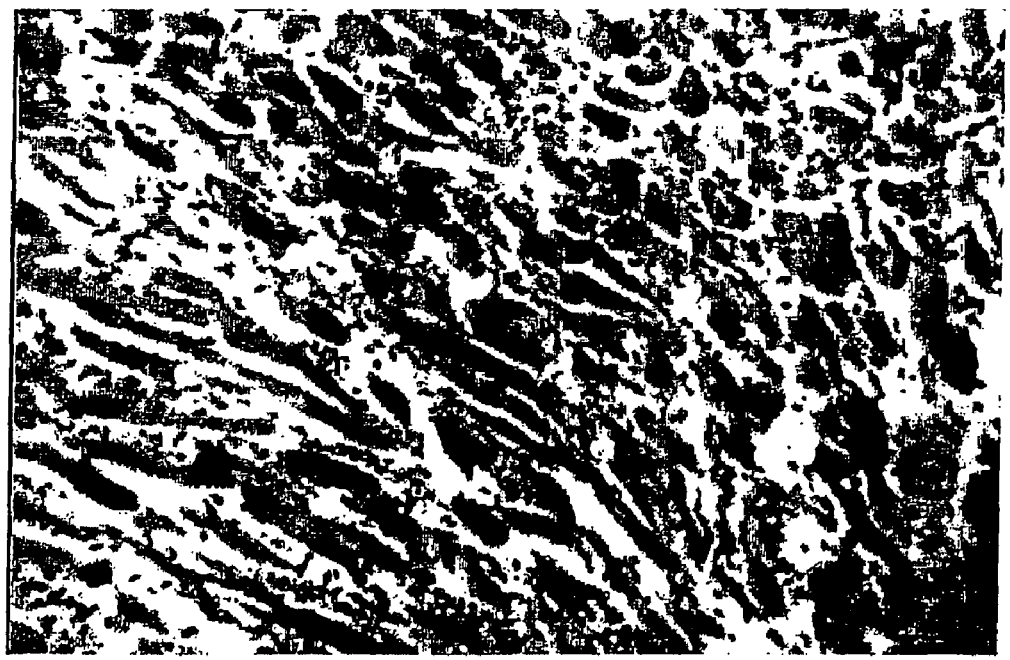
FIG. 13 depicts sporadic distribution of red stained myocardial cells seen in high dosage of rhNRG-1 β (20 μg/kg) group (II) (10×10).
Figure 14:
FIG. 14 depicts patchy distribution of red stained myocardial cells and fiber tissue seen in medium dosage level of rhNRG-1 β S177-Q237 (10 μg/kg) group (II) (10×10).
Figure 15:
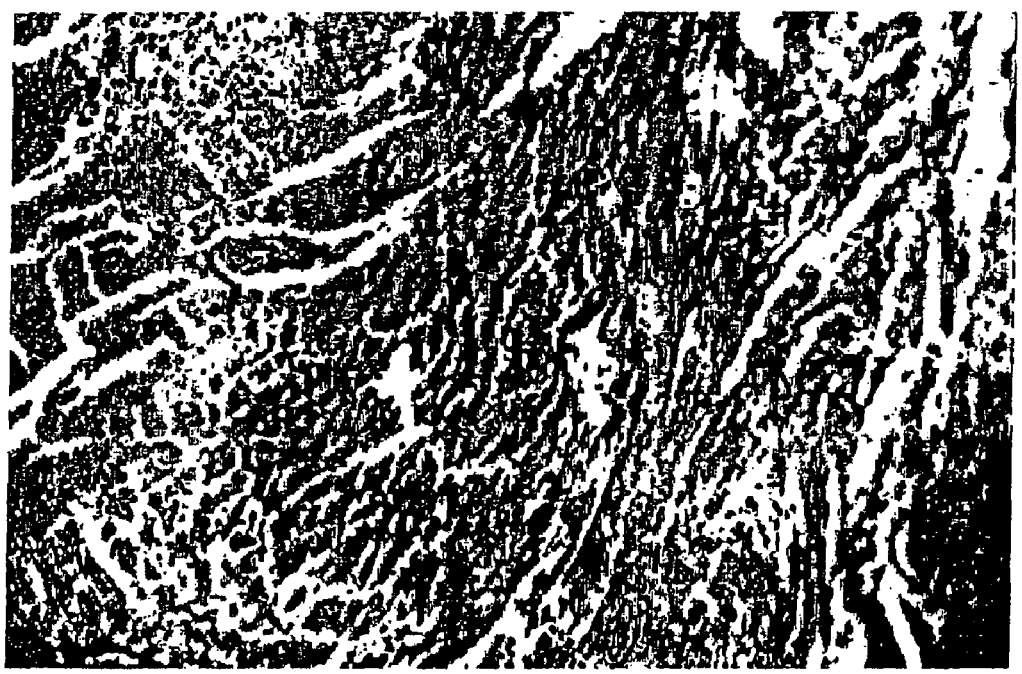
FIG. 15 depicts patchy distribution of red stained myocardial cells and fiber tissue seen in low dosage level of rhNRG-1 β S177-Q237 (5 μg/kg) group (II) (10×10).

FIG. 5. Screening for Expression of an Engineered Strain

After PCR amplification and endonuclease digestion analysis, single colony of the engineering clone (BL21-PET22b-human-neuregulin) was randomly picked to inoculate in 2 ml LB-Amp liquid medium. The culture was incubated overnight at 37° C. and shaking at 250 rpm. Then a proportion of pure culture was inoculated into 20 ml LB-Amp medium. The culture was collected after incubation at 37° C. till the turbidity increased to 1.0 at $OD_{600}$ and after IPTG was added for 4 h to induce the expression. Inclusion body was collected after the cells were destructed. After electrophoresis in 15% SDS-PAGE, thin-layer scanning analysis, Western-blotting, and repeated screening, an engineered strain (BL21-PET22b-human neuregulin) was characterized and established with stable high level expression of target protein neuregulin. The expressed target protein accounted for approximately 10% of the total protein in this strain. After high-pressure homogenate process, the target protein presented in the form of inclusion body.

The engineered strain was analyzed by SDS-PAGE electrophoresis after 4 h induction by IPTG. Inclusion body accounted for about 20% of the total proteins. Purified recombinant neuregulin specific activity was more than $5\times10^3$ EU/mg, indicating that the construction of neuregulin producing strain was successful. In addition to the SDS-PAGE, Western Blot, biological activity analysis at the stage of strain screening, further analysis was carried out, such as neuregulin amino acid composition analysis and N-terminal sequence analysis. These results indicate that the amino acid sequence of expressed recombinant human neuregulin is the same as designed.

Example 2

Therapeutic Effect of Recombinant Human Neuregulin-1 β on Heart Failure in Rat Caused by Ligation of Coronary Artery 1. Abstract Objectives To study the therapeutic effect of Recombinant Human Neuregulin-1 β (rhNRG-1 β) on heart failure in rat caused by ligation of coronary artery. Method Open the chest of rat, descending limb of the coronary was ligated with non-invasive sutures at the site between left auricle and pulmonary cone, set up a subacute heart failure rat model. In general, about 6 days after the ligation when ejection fraction of the left ventricle decreased by about 50%, The groups were randomly divided, i.e., model group, testing drug group and pseudo-operation group that only opened the chest but did not ligate the coronary artery. There were 10-13 animals in each group, 3 dosage level groups were set up for the testing drug group, they were 5, 10 and 20 μg/kg respectively, the drug was injected into the tail vein once every day for consecutive 10 days. Heart function determination (echocardiography) was performed 6 days prior to the drug administration and after the drug withdrawal, the testing animals autopsied, heart weight measured, ventricular wall thickness determined, pathologic examination and plasma renin-angiotensin-aldosterone level determined. Results After consecutive 5-day of drug administration in 3 dosage level groups of rhNRG-1 β, ejection fraction(71.1±12.0%, 64.4±12.9%, 62.9±8.4%) and shortening fraction (36.9±9.7%, 32.0±9.5%, 30.3±6.1%) of the model animals were all increased respectively and, there was significant difference between that of the 20 μg/kg, 10 μg/kg group compared with the model group (P<0.01); in addition, the changes of ejection fraction in the 20 μg/kg model group could maintain for about 35 days after the drug administration (P<0.05); 20 μg/kg of rhNRG-1 β could significantly reduce ischemic area of the myocardium, increase capillary number of the fibrotic lesion (P<0.05); 20 μg/kg and 10 μg/kg of rhNRG-1 β could reduce peripheral angiotensin I (AI), angiotensin II (AII), renin (PRA) and aldosterone (ALD) levels and with significant difference when comparing with that of the model group (P<0.01, P<0.05); There wasn't significant difference between group with consecutive 10 days of injection and group with consecutive 5 days of injection (P<0.05). Conclusion Certain dosage of rhNRG-1 β injected intravenously for consecutive 5 days could effectively treat heart failure in rat caused by ligation of coronary artery.

2. Objectives of the Experiment

To study the therapeutic effect of rhNRG-1 β on heart failure in rat caused by ligation of coronary artery.

3. Testing Drug rhNRG-1 β researched and produced by Zensun (Shanghai) Science & Technology Co Ltd, batch number: 200110006-2; concentration: 500 μg/ampule; titer determination: 5000 u/amplule; purity: >95% (HPLC-C8).

4. Experiment Animal 4.1 Species, sources and number of certificate of competency: SD rat, provided by Experimental Animal Center of Chinese Academy of Science, number of certificate of competency: Zhong Ke Yuan Dong Guan Hui 003;

4.2 Body weight, gender: 200-220 g, male.

5. Reagents and Equipments 5.1 Echocardiograph device, Hewlett Packard Sonos 5500, type of probe:S12;

5.2 Six leads electro-physiology recorder, SMUP-C-6, manufactured by Physiology Department of Shanghai Medical University;

5.3 Electro-balance, Mateler-Tolido Equipment (Shanghai) Co Ltd;

5.4 Arterial-venous indwelling needle, 20 G, produced by Sino-America Weng Zhou Hua Li Medical Equipment Company;

5.5 Micro-vernier calipers, Harbin Measure & Knife Factory;

5.6 Radio-immune γ counter, GC-1200, Zhong Jia Photoelectric Equipment Branch of General Science & Technology Industry Company of China Science & Technology University;

5.7 Renin, angiotensin kits, AI: Beijing North Bio-Tech Institute, batch number: 0210; AII: Beijing North Bio-Tech Institute, batch number: 2028;

5.8 Depilatory, 8% sodium sulfide, Xi Long Chemical Plant of GuangDong Province, batch number: 010622;

5.9 Ketamine hydrocloride, manufactured by Shanghai Zhong Xi Pharmaceuticals Co Ltd, batch number: 20020401.

6. Method of the Experiment 6.1 Experiment Grouping

Pseudo-operation group, model group and testing drug groups were set up.

Pseudo-operation group (n=10), i.e. thoracotomy but without ligating the coronary artery;

Model group (negative control group) (n=12): vehicle of the preparation was injected (10 mM PB, 0.2% human serum albumin, 5% mannitol);

Testing drug group (n=13): rhNRG-1 β with 3 dosage level, 2 subgroups were established for each dosage level group; in which, one group served as long-term monitoring after the drug administration.

6.2 Dosage Set Up of the Testing Drug and Drug Preparation, Route of Drug Administration, Times of Injection, Concentration and Volume of the Administered Drug High, medium and low dosage level group of 20 µg/kg, 10 µg/kg and 5 µg/kg respectively were set up according to the result of preliminary experiment. The drug was diluted with preparation buffer solution (10 mM PB, 0.2% human serum albumin, 5% mannitol) to the needed concentration.

Route of drug administration: in both testing drug group and model group the drug was injected into the tail vein once per day for consecutive 5 days. Echocardiography was performed at the $6^{th}$ day prior to drug administration, then continuously injected for 5 days. Volume of each drug injection was 0.4 ml/100 g body weight.

6.3 Method of the Experiment 6.3.1 Set Up Heart Failure Rat Model Through Ligation of Anterior Descending Limb of the Coronary Artery After anesthesia with intra-abdominal injection of 100 mg/kg ketamine, the rat was fixed on rat plate in supine position, disinfection of the neck region with bromo-geramine was carried out after depilating. Midline incision was made, trachea was found after separating the anterior cervical muscle, 18 G arterial indwelling trochar was inserted into the trachea at the level of 3-5 tracheal cartilage, took out the stylet, push the plastic cannula 1-2 cm further into the trachea, fixed it for later connection with ventilator for small animal (tidal volume was about 20 ml, frequency was 80/min). After cut open the left anterior chest wall skin, separated the muscle, exposed the $4^{th}$ and $5^{th}$ rib, penetrate the chest wall with curve forceps, separated tissue under the ribs, connected with ventilator, exposed the heart, monitoring the inflation of the lungs and the heart beat, tore open the pericardium, turned the upper fat pad up, full exposed the left auricle and pulmonary cone, ligated the left coronary artery between the two parts with 6/0 non-invasive suture for medical use, infarcted myocardial area (about 8mm×8mm) showed violet color, protruding and with significantly reduced activity after the ligation. Then closed the chest wall, block the opening of the ventilator to inflate the lungs, forcefully pressed the chest to drive out the air, then sutured the chest muscle and skin. Monitoring the respiration, after spontaneous respiration recovered, withdrawn the ventilator, took the animal back to its cage for breeding. In the pseudo-operation group, only the pericardium was tore open, but without the coronary artery ligation.

Echocardiograph was performed for the operated rat at about 6 days postoperatively, those animals with about 50% reduction of EF value were randomly divided into groups, the EF value of each group was all about 50%, then drug administration began.

6.3.2 Pharmacodynamic Experiment

Those animals with EF value of about 50% were randomly divided into model group (negative group) and 3-dosage level testing drug groups with 12-13 animals in each group. Route of drug administration in testing drug group and model group was injection into the tail vein, once every day for consecutive 5 days. After echocardiography at the $6^{th}$ day, another 5 days of consecutive drug administration was carried out. Drug volume of each injection was 0.4 ml/100 g body weight.

Echocardiography was again performed after the end of drug administration, the animals autopsied, heart weight measured, thickness of ventricular wall determined, pathologic examination of the heart performed, peripheral blood collected, plasma separated and renin-angiotensin-aldosterone determined.

Some testing animals of various groups were left out for long-term monitoring.

6.3.3 Observation Index 6.3.3.1 Heart Function Determination

Echocardiography was performed under anesthesia with ketamine after the legation and prior to drug administration and at the $6^{th}$ day, $11^{th}$ day of drug administration, the major index included:

EF: heart ejection fraction, reflecting ejection function of ventricle;

FS: ventricular short axis shortening rate, reflecting contraction function of ventricle;

LVDd: diastolic maximal inner diameter of left ventricle (cm);

LVDs: systolic minimal inner diameter of left ventricle (cm).

6.3.3.2 Determination of the Content of Plasma Renin-Angiotensin-Aldosterone

It was submitted to be performed by Radio-isotope Department of Zhong Shan Hospital affiliated to Fudan University.

Carotid artery phlebotomy was carried out and plasma extracted according to the mandate of the reagent kit, frozen and stored at −20° C. Renin activity (PRA), angiotensin I (AI), angiotensin II (AII) and aldosterone (ALD) content were determined with immunoassay.

6.3.3.3 Pathohistological Section of the Myocardium

It was performed by Professor Wand Bing Seng of Shanghai Difficult Pathologic Consulting Center.

After fixed with 10% formaldehyde, myocardium of the rat was longitudinally cut with equal distance into 3 slices, conventionally embedded with paraffin, section made, HE stained, image analysis for area of fibrotic region of the heart, counted the number of capillary in the fibrotic lesion (counting unit: piece/mm$^2$); Nagar-Oslen stained, studied the size of ischemic hypoxic region in the myocardium.

7. Data Processing t test was carried out for the experimental data collected.

8. Result of the Experiment 8.1 Effect of rhNRG-1 β on Function of the Ischemic Heart in Rat Results of echocardiography performed at 5-day of drug administration showed that EF value (50.2±8.4%) and FS value (22.4±4.6%) of the model group was significantly lower than EF (91.1±2.4%) and FS (57.3±3.9%) of the pseudo-operation group and with significant difference (P<0.01). Both EF value (71.1±12.0%, 64.3±12.8%, 62.9±8.4%) and FS value (36.9±9.7%, 32.0±9.5%, 30.3±6.1%) of testing drug groups (20, 10, and 5 μg/kg) increased significantly once again, and there was significant difference when comparing with those of the model group (P<0.01).

Results of repeated echocardiography performed at 10-day of drug administration showed that EF value (42.7±6.4%) and FS value (18.3±13.2%) were still significantly lower than EF (95.0±2.8%) and FS (65.3±6.8%) of the pseudo-operation group and with significant difference (P<0.01). While EF value (75.7±10.8%, 61.41±15.0%, 59.2±12.4%) and FS value (41.3±11.0%, 30.3±10.4%, 28.4±8.6%) of the testing drug groups (20, 10, 5 μg/kg) still maintained at relative high level, and there was significant difference when comparing with those of the model group (P<0.01), however, there was no significant difference when comparing with the results of 5-day of drug administration. Tables 1-6 showed the results of the two experiments.

Observation on EF value of rat heart in the model animal group and testing drug group at 5-day of drug administration and 35-day after drug withdrawal were carried out, the result showed that rat heart EF value of the 20 μg/kg rhNRG-1 β group maintained stable at relatively high level and there was significant difference when comparing with that of the model animal group (P<0.05) (Table 7).

TABLE 1

Measurement parameters of heart function prior to drug administration in ligation of anterior descending limb of the coronary artery produced heart failure model animals (1)

| Group | LVDd | LVDs | EF | FS |
| --- | --- | --- | --- | --- |
| Pseudo-operation group (n = 6) | 0.572 ± 0.033* | 0.258 ± 0.046** | 89.5 ± 4.4** | 55.2 ± 5.8** |
| Model group (n = 12) | 0.705 ± 0.117 | 0.558 ± 0.119 | 48.3 ± 10.3 | 21.3 ± 5.6 |
| rhNRG-1 β group 20 μg/kg (n = 13) | 0.730 ± 0.108 | 0.575 ± 0.119 | 49.3 ± 11.4 | 21.7 ± 6.4 |
| rhNRG-1 β group 10 μg/kg (n = 13) | 0.709 ± 0.099 | 0.555 ± 0.102 | 49.5 ± 11.0 | 22.1 ± 6.1 |
| rhNRG-1 β group 5 μg/kg (n = 13) | 0.761 ± 0.075 | 0.596 ± 0.092 | 49.3 ± 10.6 | 22.0 ± 5.9 |

*P < 0.05,
**<0.01, when comparing with that of the model animal group

TABLE 2

Measurement parameters of heart function 5 days after the drug administration in ligation of anterior descending limb of the coronary artery produced heart failure model animals (1)

| Group | Drug administration | LVDd | LVDs | EF | FS |
| --- | --- | --- | --- | --- | --- |
| Pseudo-operation group(n = 6) | iv qd × 5 | 0.549 ± 0.046** | 0.234 ± 0.027** | 91.1 ± 2.4** | 57.3 ± 3.9** |
| Model group (n = 12) | iv qd × 5 | 0.79 ± 0.08 | 0.61 ± 0.09 | 50.24 ± 8.41 | 22.43 ± 4.62 |
| rhNRG-1 β 20 μg/kg (n = 13) | iv qd × 5 | 0.70 ± 0.07** | 0.46 ± 0.09** | 71.07 ± 11.99** | 36.88 ± 9.66** |
| rhNRG-1 β 10 μg/kg (n = 13) | iv qd × 5 | 0.71 ± 0.05* | 0.51 ± 0.09** | 64.35 ± 12.85** | 32.01 ± 9.54** |
| rhNRG-1 β 5 μg/kg (n = 11) | iv qd × 5 | 0.73 ± 0.05* | 0.54 ± 0.09* | 62.90 ± 8.39** | 30.32 ± 6.11** |

*p < 0.05,
**p < 0.01, when comparing with that of the model group

TABLE 3

Measurement parameters of heart function 10 days after the drug administration in ligation of anterior descending limb of the coronary artery produced heart failure model animals (1)

| Group | Drug administration | LVDd | LVDs | EF | FS |
|---|---|---|---|---|---|
| Pseudo-operation (n = 6) | iv qd × 10 | 0.466 ± 0.041** | 0.159 ± 0.036** | 95.0 ± 2.8** | 65.3 ± 6.8** |
| Model group 1 (n = 10) | iv qd × 10 | 0.8 ± 0.11 | 0.7 ± 0.11 | 42.7 ± 6.36 | 18.3 ± 3.19 |
| rhNRG-1 β 20 μg/kg (n = 10) | iv qd × 10 | 0.6 ± 0.12** | 0.5 ± 0.14** | 75.7 ± 10.78** | 41.3 ± 10.98** |
| rhNRG-1 β 10 μg/kg (n = 10) | iv qd × 10 | 0.7 ± 0.07** | 0.51 ± 0.14** | 61.4 ± 15** | 30.3 ± 10.36** |
| rhNRG-1 β 5 μg/kg (n = 10) | iv qd × 10 | 0.72 ± 0.10* | 0.55 ± 0.12* | 59.2 ± 12.37** | 28.4 ± 8.62** |

*p < 0.05,
**p < 0.01, when comparing with that of the model group

TABLE 4

Measurement parameters of heart function 10 days after the drug administration in ligation of anterior descending limb of the coronary artery produced heart failure model animals (II)

| Group | LVDd | LVDs | EF | FS |
|---|---|---|---|---|
| Pseudo-operation group (n = 6) | 0.544 ± 0.071* | 0.215 ± 0.053** | 93 ± 2.9** | 60.8 ± 5.2** |
| Model group (n = 12) | 0.66 ± 0.10 | 0.52 ± 0.11 | 46.98 ± 14.17 | 20.85 ± 7.38 |
| rhNRG-1 β 20 μg/kg (n = 12) | 0.74 ± 0.12 | 0.56 ± 0.11 | 52.29 ± 12.87 | 23.89 ± 7.28 |
| rhNRG-1 β 10 μg/kg (n = 12) | 0.64 ± 0.11 | 0.49 ± 0.11 | 51.67 ± 11.92 | 23.27 ± 6.73 |
| rhNRG-1 β 5 μg/kg (n = 12) | 0.66 ± 0.11 | 0.51 ± 0.12 | 50.81 ± 12.55 | 22.83 ± 6.92 |

*p < 0.05,
**p < 0.01, when comparing with that of the model group

TABLE 5

Measurement parameters of heart function 5 days after the drug administration in ligation of anterior descending limb of the coronary artery produced heart failure model animals (II)

| Group | Drug administration | LVDd | LVDs | EF | FS |
|---|---|---|---|---|---|
| Pseudo-operation group (n = 6) | iv qd × 5 | 0.553 ± 0.063** | 0.215 ± 0.052** | 93.1 ± 3.9** | 61.4 ± 6.2** |
| Model group (n = 10) | iv qd × 5 | 0.87 ± 0.11 | 0.74 ± 0.14 | 38.00 ± 12.36 | 16.35 ± 5.55 |
| rhNRG-1 β 20 μg/kg (n = 9) | i.v qd × 5 | 0.68 ± 0.11** | 0.46 ± 0.17** | 65.47 ± 20.48** | 34.23 ± 15.42** |
| rhNRG-1 β 10 μg/kg (n = 12) | iv qd × 5 | 0.72 ± 0.13** | 0.54 ± 0.14** | 56.51 ± 12.68** | 26.53 ± 8.48** |
| rhNRG-1 β 5 μg/kg (n = 10) | iv qd × 5 | 0.74 ± 0.11* | 0.58 ± 0.18* | 56.76 ± 16.10** | 28.35 ± 10.64** |

*p < 0.05,
**p < 0.01, when comparing with that of the model group

TABLE 6

Measurement parameters of heart function 10 days after the drug administration in ligation of anterior descending limb of the coronary artery produced heart failure model animals (II)

| Group | Drug administration | LVDd | LVDs | EF | FS |
|---|---|---|---|---|---|
| Psudo-operation group (n = 6) | iv 10qd | 0.539 ± 0.015** | 0.204 ± 0.017** | 93.8 ± 1.6** | 62.2 ± 3.6** |
| Model group (n = 10) | iv 10qd | 0.81 ± 0.13 | 0.69 ± 0.13 | 36.13 ± 10.10 | 15.18 ± 5.01 |
| rhNRG-1 β 20 µg/kg (n = 8) | iv 10qd | 0.65 ± 0.09** | 0.42 ± 0.13** | 70.22 ± 14.15** | 36.49 ± 11.27** |
| rhNRG-1 β 10 µg/kg (n = 12) | iv 10qd | 0.68 ± 0.08** | 0.49 ± 0.17** | 66.54 ± 15.81** | 34.28 ± 12.64** |
| rhNRG-1 β 5 µg/kg (n = 9) | iv 10qd | 0.70 ± 0.08* | 0.53 ± 0.16* | 57.90 ± 19.54** | 29.26 ± 14.19* |

*p < 0.05,
**p < 0.01, when comparing with that of the model group

TABLE 7

EF value of heart function measured at 5-day of drug administration and 35-day after drug withdrawal in model animals

| | After ligation prior to drug administration | 5-day after drug administration | 5-day after drug administration and 35-day after drug withdrawal |
|---|---|---|---|
| rhNRG-1 β 20 µg/kg | 52.4 ± 13.8 | 79.2 ± 4.7* | 73.0 ± 20.3* |
| rhNRG-1 β 10 µg/kg | 52.2 ± 12.8 | 77.3 ± 11.6 | 63.8 ± 23.8 |
| rhNRG-1 β 5 µg/kg | 53.1 ± 12.8 | 75.8 ± 15.3 | 69.9 ± 28.6 |
| Model group | 53.0 ± 12.6 | 62.6 ± 16.7 | 52.5 ± 29.9 |
| Pseudo-operation group | 94.4 ± 3.7** | 94.1 ± 2.5** | 95.1 ± 2.3** |

*p < 0.05;
**p < 0.01, when comparing with that of the model animal group 8.2 Effect of rhNRG-1 β on Pathohistology of Model Rat Myocardium 8.2.1 Effect of rhNRG-1 β on the Severity of Myocardial Ischemia and Hypoxia in Model Animals In Nagar-Oslen stained section, normal myocardium stained with light yellow color, while ischemic hypoxic area stained deeper with reddish color. Ischemic hypoxic changes could be analyzed with this method and comparison of qualitative and semi-quantitative test could be made.

FIGS. 6-15 showed the pathohistological changes of the various testing group. Myocardium of the model group stained deep color, large patch of myocardium was stained with red color, while that of the pseudo-operation group stained yellow, without red stained area; red stained myocardial cells of 20 µg/kg rhNRG-1 β showed punctuate distribution; red stained tissue of 10 µg/kg and 5 µg/kg groups showed patchy distribution, demonstrating that rhNRG-1 β could alleviate the severity of ischemic hypoxic damages.

Figure 16:
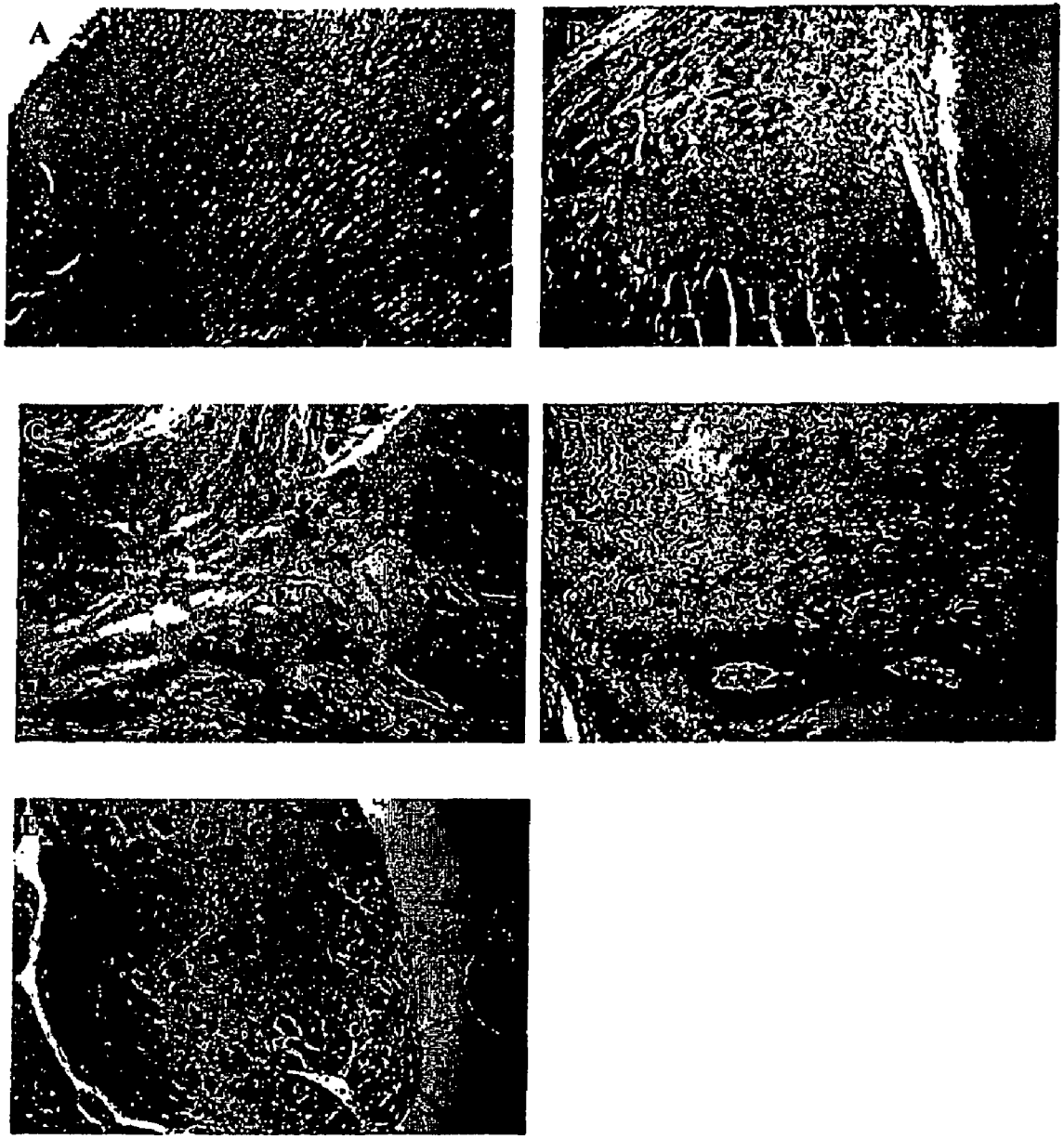
FIG. 16 illustrates effect of rhNRG-1 β on capillary regeneration in myocardial fibrotic area of model animal (I) (HE stained, 50×); A: Pseudo-operation group: normal myocardial structure, with fibrotic changes; B: Model animal group: marked myocardial fibrosis and small amount of capillary proliferation was seen; C: 20 μg/kg rhNRG-1 β group: patchy fibrotic changes in myocardium, significant capillary proliferation; D: 10 μg/kg rhNRG-1 β group: marked fibrotic changes with relatively large number of capillary proliferation; and E: 5 μg/kg rhNRG-1 β group: patchy fibrotic changes and capillary proliferation could be seen.
Figure 17:
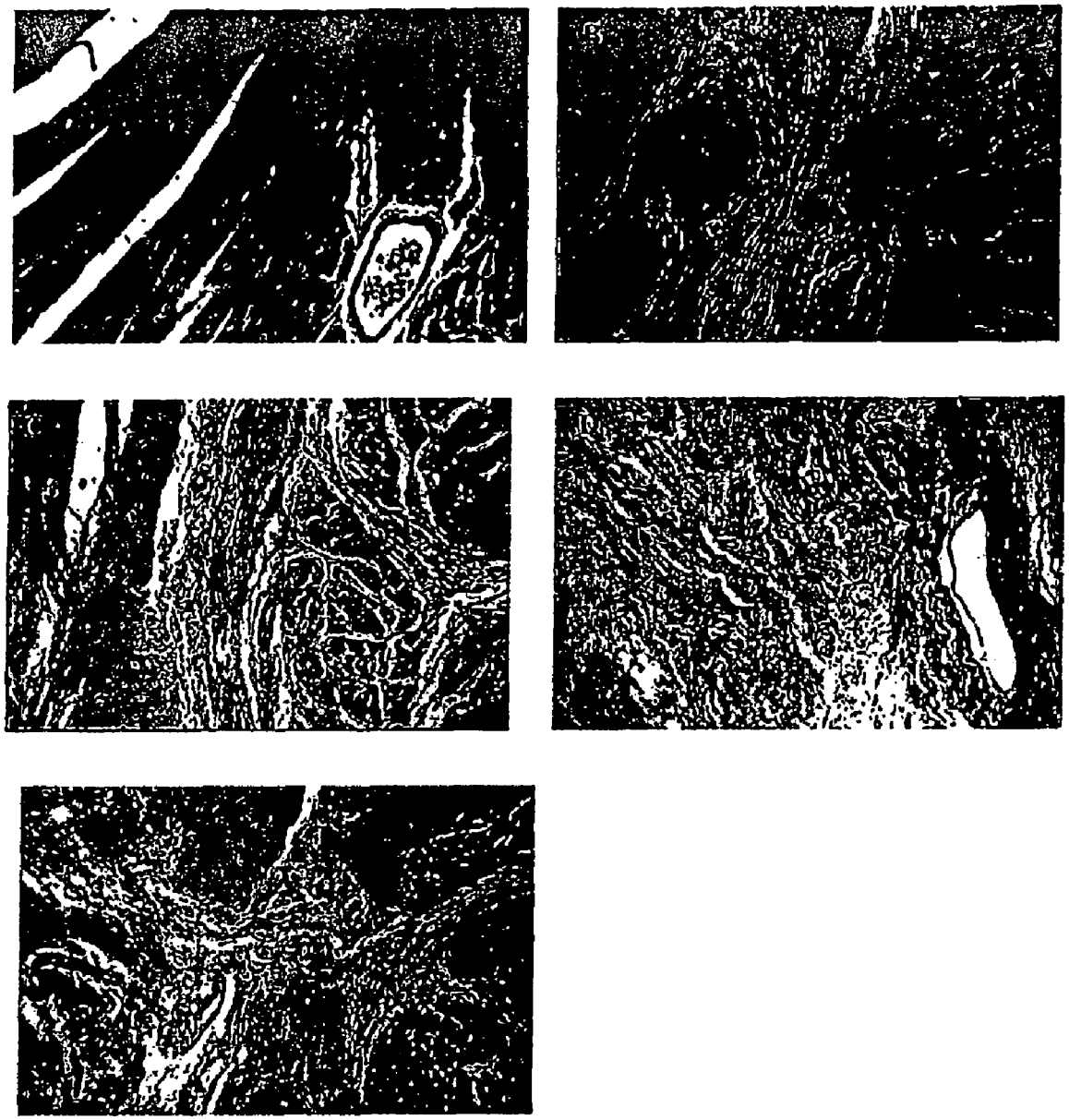
FIG. 17 illustrates effect of rhNRG-1 β on capillary proliferation in myocardial fibrotic area of model animal (II) (HE stained, 50×); A: Pseudo-operation group: normal myocardial structure, with fibrotic changes; B: Model animal group: marked myocardial fibrotic changes, small number of capillary proliferation could be seen; C: 20 μg/kg rhNRG-1 β group: patchy fibrotic changes in myocardium, significant capillary proliferation; D: 10 μg/kg rhNRG-1 β group: marked fibrotic changes, there were relatively large number of capillary proliferation; and E: 5 μg/kg rhNRG-1 β group: patchy fibrotic changes, capillary proliferation could be seen.

8.2.2 Effect of rhNRG-1 β on Capillary Regeneration in the Fibrotic Area of Ischemic Myocardium of Model Rat Changes of capillary number in myocardial tissue of various testing groups were studied with Leica image analysis system. The results revealed that there was increase of capillary number in the fibrotic lesion of myocardium of model animal in the testing drug group with rhNRG-1 β and there was significant difference between 20 µg/kg dosage level group and that of the model group (P<0.01), no statistic difference was seen between 10 µg/kg and 5 µg/kg dosage level groups and that of the model group, demonstrating that high dosage of rhNRG-1 β (20 µg/kg) could promote capillary proliferation in myocardial fibrotic lesion after ligation of the coronary artery in rat (Table 8, FIGS. 16 and 17).

TABLE 8

Effect of rhNRG-1 β on capillary regeneration in myocardial fibrotic area of model animal

| Group | Drug administration | Capillary counting (I) | Capillary counting (II) |
|---|---|---|---|
| Pseudo-operation group | iv qd × 10 | 0 ± 0 | 0 ± 0 |
| Model group | iv qd × 10 | 6.49 ± 2.17 | 13.7 ± 5.5 |
| rhNRG-1 β 20 µg/kg | iv qd × 10 | 10.12 ± 3.0** | 24.6 ± 9.5** |
| rhNRG-1 β 10 µg/kg | iv qd × 10 | 8.99 ± 3.3 | 19.6 ± 8.5 |
| rhNRG-1 β 5 µg/kg | iv qd × 10 | 9.35 ± 4.2 | 15.0 ± 6.9 |

**P < 0.01, when comparing with that of the model group 8.3 Effect of rhNRG1 β on Plasma Rennin-Angiotensin-Aldosterone Level in Model Animal Plasma rennin (PRA), angiotensin I (AI), angiotensin II (AII) and aldosterone (ALD) levels was determined in various testing drug groups with radioimmunoassay. In the model animal group, the results showed that PRA, AI, AII and ALD were 3.506±1.78 ng/ml.h, 10.655±1.18 ng/ml, 1366.38±577.33 µg/ml and 1.738±0.34 ng/ml respectively; Comparing with those of the pseudo-operation group (1.315±0.96 ng/ml, 8.125±1.57 ng/ml, 564.37±273.56 pg/ml and 1.113±0.45 ng/ml), the content increased significantly, the difference was significant statistically (P<0.05).

Plasma AI (7.40±12.15, 7.65±1.40 ng/ml), and AII (641.47±283.86, 468.58±165.10 pg/ml) level reduced significantly in 20, and 10 µg/kg rhNRG-1 β group with significant difference (P<0.01); PRA (1.337±1.09, 1.075±1.50 ng/ml.h) and ALD (1.02±0.27, 1.26±0.38 ng/ml) reduced significantly as well and there was significant difference when comparing with that of the model animal group (P<0.05). However, when comparing with that of the pseudo-operation group, the difference has no statistical implication (P>0.05), demonstrating that certain dosage level of rhNRG-1 β could reduced plasma PRA, AI, AII and ALD content in rat after ligation of its coronary artery (Table 9).

TABLE 9

Plasma rennin (PRA), angiotensin I (AI), angiotensin II (A II) and aldosterone (ALD) in various testing group model animals

| Group | Drug administration | AI(ng/ml) | AII(Pg/ml) | ALD(ng/ml) | PRA (ng/ml h) |
|---|---|---|---|---|---|
| Pseudo-operation n = 6 | iv qd × 10 | 8.125 ± 1.573* | 564.370 ± 273.56* | 1.113 ± 0.447* | 1.315 ± 0.96* |
| rhNRG-1 β (n = 6) | iv qd × 10 | 10.655 ± 1.178 | 1366.38 ± 577.33 | 1.738 ± 0.337 | 3.506 ± 1.78 |
| rhNRG-1 β 20 μg/kg (n = 6) | iv qd × 10 | 7.400 ± 2.15** | 641.47 ± 283.86* | 1.018 ± 0.266** | 1.337 ± 1.09* |
| rhNRG-1 β 10 μg/kg (n = 6) | iv qd × 10 | 7.654 ± 1.399** | 468.583 ± 165.1** | 1.264 ± 0.382* | 1.075 ± 1.5* |
| rhNRG-1 β 5 μg/kg (n = 6) | iv qd × 10 | 10.036 ± 2.283 | 807.304 ± 333.46 | 1.472 ± 0.413 | 4.032 ± 1.81 |

*p < 0.05,
**p < 0.01, when comparing with that of the model group

9. Conclusion

When comparing with the ejection fraction (50.2±8.4%) and shortening fraction (22.4±4.6%) of the model control group, three dosage level of rhNRG-1 β injected for consecutive 5 days could raise the ejection fraction (71.1±12.0%, 64.4±12.9%, 62.9±8.4%)and shortening fraction (36.9±9.7%, 32.0±9.5%, 30.3±6.1%) and there was significant difference between 20 μg/kg, 10 μg/kg group and the model animal group (P<0.01), in addition, changes of ejection fraction in testing drug group model animal could maintain for about 35 days after drug administration (P<0.05); 20 μg/kg of rhNRG-1 β could significantly reduce ischemic hypoxic area of the myocardium, increase capillary number in the fibrotic lesion (P<0.05); 20 μg/kg and 10 μg/kg of rhNRG-1 β could reduce angiotensin I (AI), angiotensin II (AII), rennin (PRA) and aldosterone (ALD) levels in the peripheral blood of model animals and with significant difference when comparing with that of the model animal group (P<0.01, P<0.05). There was no significant difference between those with consecutive 10 days of drug administration and those with consecutive 5 days of drug administration (P<0.05).

Results of the experiment showed that certain dosage of 20 μg/kg of rhNRG-1 β injected intravenously for consecutive 5 days could effectively treat rat heart failure caused by ligation of the coronary artery.

Example 3

Therapeutic Effect of 20 μg/kg of rhNRG-1 β on Heart Failure Caused by Adriamycin in SD Rat 1. Abstract Objectives To study therapeutic effect of 20 μg/kg of rhNRG-1 β on toxic myocarditis caused by Adriamycin in rat. Method 3.3 mg/kg of Adriamycin was injected in SD rat's tail vein, once every week for consecutive 4 injections, set up Adriamycin caused SD rat toxic myocarditis model. 3-dosage levels of rhNRG-1 β groups were set up, they were 10, 20 and 40 μg/kg once intravenous injection per day (qd) for consecutive 10 days. Survival of the animals was monitored; blood flow dynamic index, ratio of heart weight/body weight, pathologic examination of the myocardium were monitored at the end of the experiment, serum troponin T (cTnT) level was determined as well. Results The survival rate of 40, 20 and 10 μg/kg dosage level of rhNRG-1 β group raised significantly when comparing with that of the 15% survival rate of the model animals, reached 85%, 90% and 60% respectively, dp/dt, —dp/dt and LVPmax of high, medium and low testing drug dosage level groups raised significantly, dp/dt reached 5954±689, 6107±418 and 4875±636 respectively, –dp/dt was –4794±954, –4323±457 and –3672±884 respectively, LVPmax was 165.7±22.7, 156.1±17.7 and 145±15.2 respectively, there was significant difference when comparing with those of the model animal group (P<0.001), in addition, there was significant difference in dp/dt, –dp/dt, LVPmax between 40 and 20 μg/kg dosage groups and those of 10 μg/kg dosage group P<0.05) and was somewhat dosage dependent; 40, 20 and 10 μg/kg of rhNRG-1 β could effectively alleviate the severity of myocardial damage in model animals, reduced serum troponin T (cTnT) level, they were 0.025±0.011, 0.031±0.006 and 0.074±0.024 respectively, with significant difference when comparing with that of 0.205±0.072 of the model group (P<0.01). Conclusion 20 μg/kg of rhNRG-1 β could effectively treat toxic myocardial damage caused by Adriamycin in rat.

2. Objectives of the Experiment

To study the therapeutic effect of rbNRG-1 β on toxic myocarditis caused by Adriamycin in rat.

3. Testing Drug rhNRG-1 β, provided by Zensun (Shanghai) Science & Technology Development Co. Ltd. Batch number: 200110006-2 Specification: 500 μg/ampule. Titer determination: 5000 u/ampule; Purity:>95% (HPLC-C8).

4. Experiment Animal

SD rat: provided by Experimental Animal Center of Fudan University Medical College, Number of certificate of animal competency: Yi Dong Zi 02-22-11. body weight 250±30 g, male.

The animals were randomly divided in groups, 20 animals in each group, bred in separate cage.

Temperature of the animal room was 18-22° C., with relative humidity of 50%-70%.

5. Reagents and Equipment

Six leads electro-physiology recorder, SMUP-C-6, manufactured by Physiology Department of Shanghai Medical University;

Energy exchanger (Japan Photoelectricity Industry Company, NIHON KOHDEN, model: TP-400T);

Electrochemistry luminescence automatic immune analysis device (model 2010): Roche Diagnostics Co Ltd, batch number 158468;

Precisive electro-balance, (Mateler-Tolido Equipment Co Ltd; Max: 610 g d=0.01 g); Micro-vermier calipers, (Harbin Measure & Knife Factory, 0.05 mm);

Arterial-venous indwelling needle, 20 Gm produced by Sino-America Weng Zhou Hua Li Medical Equipment Company;

Reagent kit for serum troponin determination (Behring Dignostic Inc.).

6. Method of the Experiment 6.1 Experiment Grouping

Normal control group, model animal group and testing drug group were set up;

Model group (negative control group: Adriamycin, manufactured by MingZhi Pharmaceuticals; ShanTou Special Economy Prefecture (batch number: 000201, expired date: 2003.2);

Testing drug group: rhNRG-1 β group.

6.2 Dosage Set Up, Preparation of Testing Drug, Route of Drug Administration, Times of Drug Administration, Concentration and Volume of the Testing Drug 3-dosage levels of 10, 20 and 40 μg/kg of the testing drug group were established. Dissolved with 1 ml of water for injection and adjusted to needed concentration with excipient. Major component of the excipient was 5% mannitol for injection, 0.2% human serum albumin for injection, 10 mM phosphate buffer solution, provided by Zensun (Shanghai) Science & Technology Development Co Ltd. The testing drug was prepared prior to injection.

rhNRG-1 β was injected into the tail vein within 24 hours after the first injection of Adriamycin, the injection of rhNRG-1 β was carried out once daily for 10 days. Dosage was adjusted according to the body weight, volume of the drug administered was 0.2 ml/100 g.

6.3 Method of the Experiment 6.3.1 Method of Construction of Animal Heart Failure Model Based on the <<Guidance Principle of New Drug Preclinical Experiment>>, 3.3 mg/kg of Adriamycin was injected into the tail vein, once per week for consecutive 4 injections, establishing Adriamycin caused toxic myocarditis rat model.

6.3.2 Pharmacodynamic Experiment rhNRG-1 β was injected into the tail vein within 24 hours after the first injection of Adriamycin. During the experiment, animal survival was dynamically monitored, heart fraction indexes (maximal rate of pressure increase within left ventricle, dt/dpmax, maximal rate of pressure decrease within left ventricle, -dp/dt, systolic end pressure of left ventricle LVPmax, diastolic end pressure of left ventricle LVPmin) were monitored at the 5$^{th}$ week. Section was made from the heart tissue and pathological changes examined.

6.3.3 Observation Index 6.3.3.1 Survival Rate

Situation of survival was recorded weekly and the survival rate of the various experimental groups was calculated. Survival rate (%)=survival animal number/number of experimental animals×100.

6.3.3.2 Ratio of Heart Weight/Body Weight, Pathologic Section of Heart Tissue

Heart was extirpated after thoracotomy (auricle should be reserved), the heart weight was measured after dried with absorbent paper, ratio of heart weight/body weight calculated; outer diameter of the heart was measured at ½ site of the vertically standing heart; medium part of the left ventricle was crosswise cut open, maximal thickness of free wall of the left ventricle measured; the heart was fixed with 10% formaldehyde, paraffin embedded and HE stained, observation of the myocardial structure carried out under optic microscope, give out pathologic score.

Criteria of the Pathologic Scoring:

Grade 0: normal myocardial structure, without atrophy or hypertrophy of the myocardial cells, with vacuole, cross striation clear; regular arrangement of the myocardium; endocardium and pericardium without abnormality; no changes in blood vessel and interstitial tissue.

Grade 1: Focal dissolve of myocardial cytoplasm and vacuole formation were seen in sporadic individual myocardial cells, while the neighboring myocardial cells still looked normal.

Grade 2: Atrophy, dissolve of myocardial cytoplasm and vacuole formation was seen in small to medium extent of clustering myocardial cells, small focal necrosis of myocardial cells was also seen.

Grade 3: Large extent of diffuse atrophy of myocardial cells, dissolve of cytoplasm or vacuole formation with quite marked necrosis. Scoring could be performed between grade 1 and grade 2 or between grade 2 and grade 3, e.g. grade 1.5, grade 2.5 etc.

6.3.3.3 Determination of Hemodynamics Index

Hemodynamics index such as carotid artery pressure, intra-ventricular pressure. dp/dt was measured with six lead physiology recorder. Major procedure: separate the right carotid artery, ligate its distal end and block its proximal end with arterial clamps, 20 G arteriovenous indwelling needle was inserted into the carotid artery, took out the medal stylet, loosened the artery clamps, push the plastic trocar further into appropriate depth, indwelled for 10 minutes, observed the wave style recorded by the physiology recorder, after it was stable, then recorded the carotid artery pressure and push the trocar further into the left ventricle, kept in place for 15 minutes, after it was stable, then recorded the dp/dt, -dp/dt, $LVP_{max}$ and $LVP_{min}$.

6.3.3.4 Determination of Serum Troponin T (cTnT) Level 2 ml of arterial blood was withdrawn, serum extracted, frozen and stored at −20° C., determination of serum cTnT content was performed with electrochemistry irradiate method submitted to be carried out by Clinical Laboratory of Zhong Shan Hospital.

7. Data Processing

Data was expressed as X±SD. Inter-group difference was analyzed with monofactorial variance analysis.

8. Results of the Experiment 8.1 Adriamycin Could Induce Toxic Myocarditis Complicated with Heart Failure in Rat Refer to Table 10, and FIG. 18. 3.3 mg/kg of Adriamycin was intravenously injected once every week for 4 consecutive injections, 5 weeks later, animal survival rate was 15%, significant heart function damage was seen in the survived rat, their dp/dt, -dp/dt, LVPmax, LVPmin was 43%, 47%, 58% and 37% of the normal value respectively, pathologic scoring of the myocardial tissue was 2.33±0.26, relative morbidity rate was 100%, serum cTnT raised significantly and reached 0.2 ng/ml, demonstrating that toxic myocarditis and the resulting heart failure caused by Adriamycin animal model was successfully established.

TABLE 10

Various determination index of toxic myocarditis
induced by Adriamycin rat model

|  | Control group | Model animal group |
|---|---|---|
| survival rate (%) | 100 | 15 |
| pathologic score of myocardial tissue | 0 | 2.33 ± 0.26* |
| dp/dt (mmHg/s) | 6235 ± 423 | 2674 ± 446** |
| −dp/dt | −4590 ± 1003 | −2141 ± 596** |
| LVPmax (mmHg) | 181.4 ± 15.4 | 106.1 ± 21.2* |
| LVPmin | −27.1 ± 10.2 | −10.0 ± 4.7** |
| cTnT (ng/ml) | 0.001 ± 0.000 | 0.205 ± 0.072** |
| heart weight/body weight | 0.0032 ± 0.0002 | 0.0031 ± 0.0001 |
| thickness of left ventricular wall (mm) | 1.88 ± 0.15 | 1.73 ± 0.16 |
| heart circumference (mm) | 31.0 ± 1.1 | 30.6 ± 0.1 | n = 20, X ± SD, when comparing with that of the normal group, variance analysis,
*P < 0.05
**P < 0.001.

Figure 18:
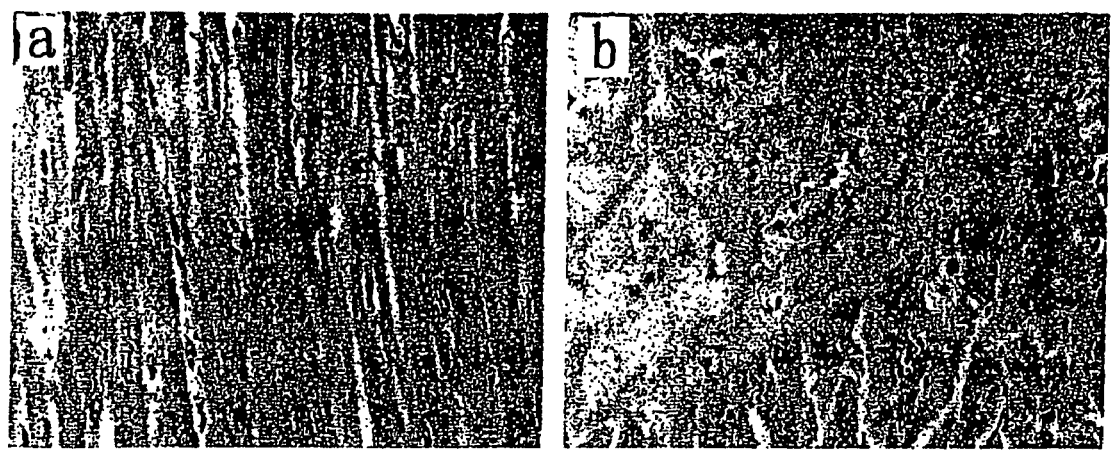
FIG. 18 illustrates myocardium pathologic section of SD rat toxic myocarditis induced by Adriamycin; a: normal control group: pathologic score of myocardium was 0, without myocardial cells atrophy and hypertrophy, with vacuole formation, cross striation can be clearly seen; myocardium arranged regularly; no abnormality of endocardium and pericardium; no changes of the vessels and interstitial tissue; b: model animal group: pathologic score of the myocardium was 3, large area of myocardial cell necrosis and dissolution.

FIG. 18 illustrates myocardium pathologic section of SD rat toxic myocarditis induced by Adriamycin; a: normal control group: pathologic score of myocardium was 0, without myocardial cells atrophy and hypertrophy, with vacuole formation, cross striation can be clearly seen; myocardium arranged regularly; no abnormality of endocardium and pericardium; no changes of the vessels and interstitial tissue; b: model animal group: pathologic score of the myocardium was 3, large area of myocardial cell necrosis and dissolution.

8.2 Effect of rhNRG-1 β on Survival Rate of the Model Animals

Figure 19:
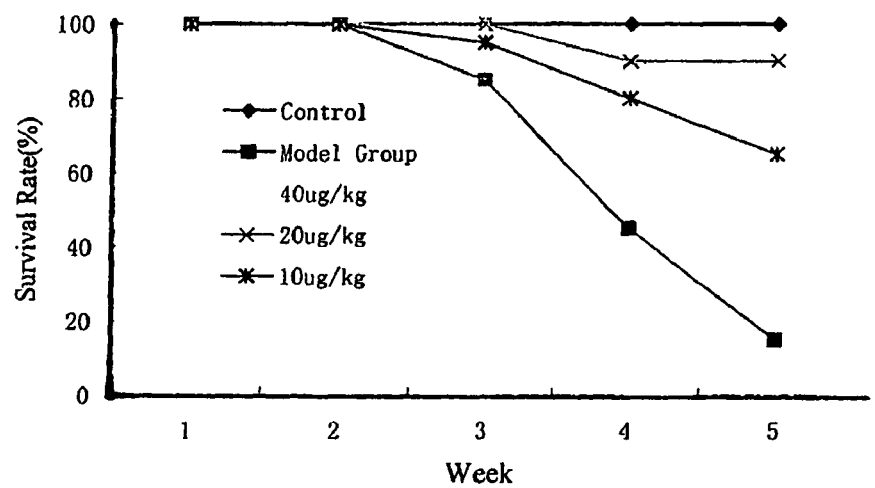
FIG. 19 illustrates effect of rhNRG-1 β on survival rate of the model animals.

The results showed that with time of the experiment extended, all of the three-dosage levels of rhNRG-1 β could significantly reduce mortality of the model animals, survival rate of the model animal of 20 μg/kg dosage group reached up to 90% (P<0.01) (FIG. 19).

8.3 Effect of rhNRG-1 β on Heart Function of Model Animals

After the drug administration, dp/dt and LVPmax in all the testing drug group animals raised somewhat. Through monofactorial variance analysis with SPSS software, inter-groups comparison showed that dp/dt and −dp/dt of testing drug group animals was significantly higher than those of the model animal group (P<0.001), the difference was not significant when comparing with those of the control group (P>0.05). Those of 40 and 20 μg/kg dosage group were significantly higher than those of 10 μg/kg group (P<0.01); LVPmax of the testing drug group (40, 20 and 10 μg/kg) was significantly higher than that of the model animal group (P<0.001) as well, in addition, the difference between various testing drug groups was significant statistically (P<0.05), demonstrating that rhNRG-1 β could effective improve heart function of the model animals and was dose-dependent. Results of the two experiments were coincident (Tables 11 and 12).

TABLE 11

Effect of rhNRG-1 β on heart function of model animals (I)

| Group | Drug administration | +dp/dt (mmHg/s) | −dp/dt (mmHg/s) | LVPmax (mmHg) | LVPmin (mmHg) |
|---|---|---|---|---|---|
| Normal control group (n = 8) |  | 6235 ± 423** | −4590 ± 1003** | 181.4 ± 15.4** | −27.1 ± 10.2** |
| Model group (n = 6) | iv qd × 10 d | 2674 ± 446 | −2141 ± 596 | 106.1 ± 21.2 | −10 ± 4.7 |
| rhNRG-1 β 40 μg/kg (n = 8) | iv qd × 10 d | 5954 ± 689** | −4794 ± 954** | 165.7 ± 22.7** | −27.4 ± 10** |
| rhNRG-1 β 20 μg/kg (n = 8) | iv qd × 10 d | 6107 ± 418** | −4323 ± 457** | 156.1 ± 17.7** | −26.9 ± 9.7** |
| rhNRG-1 β 10 μg/kg (n = 8) | iv qd × 10 d | 4875 ± 636** | −3672 ± 884** | 145 ± 15.2** | −24.5 ± 9.6** |

*p < 0.05;
**p < 0.001, when comparing with that of the model animal group

TABLE 12

Effect of rhNRG-1 β on heart function of model animals (II)

| Sample | Drug administration | +dp/dt(mmHg/s) | −dp/dt (mmHg/s) | LVPmax (mmHg) | LVPmin (mmHg) |
|---|---|---|---|---|---|
| Normal group(n = 8) |  | 5872 ± 342** | −4626 ± 896** | 159 ± 25** | −22.7 ± 12* |
| Model animal group (n = 8) | iv qd × 10d | 2675 ± 359 | −2137 ± 334 | 103.9 ± 11.5 | −11.3 ± 5.4 |
| rhNRG-1 β 40 μg/kg (n = 7) | iv qd × 10d | 6041 ± 461** | −4529 ± 274** | 166.3 ± 12.4** | −22.2 ± 11.4* |
| rhNRG-1 β 20 μg/kg (n = 7) | iv qd × 10d | 5833 ± 416** | −4345 ± 807** | 157.7 ± 12** | −26.6 ± 7.4* |
| rhNRG-1 β 10 μg/kg (n = 8) | iv qd × 10d | 4956 ± 352** | −3626 ± 1056** | 158.2 ± 22.9** | −22.4 ± 18 |

*p < 0.05;
**p < 0.001, when comparing with that of the model animals

8.4 Effect of rhNRG-1 β on Myocardial Structure of Model Animals rhNRG-1 β could significant reduce the severity of myocardial cells damage in model animals, significant reduce pathologic score and the difference was significant statistically when comparing with that of the model group (P<0.01, P<0.05). Tables 13 and 14 and FIG. 20 showed the results of the two experiments.

Figure 20:
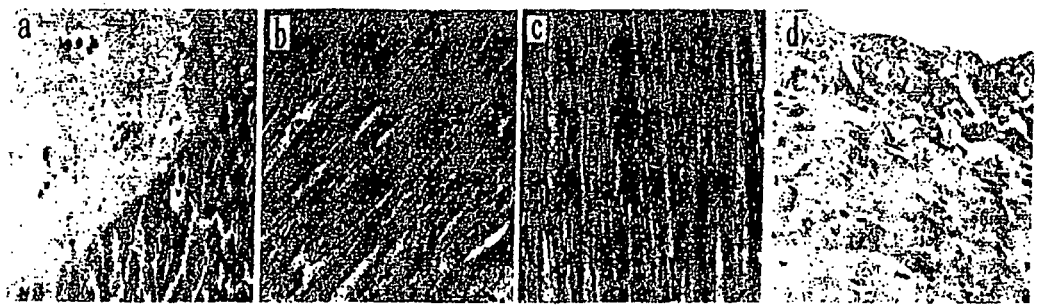
FIG. 20 illustrates effect of rhNRG-1 β on myocardial structure of model animals.

FIG. 20. Effect of rhNRG-1 β on Myocardial Structure of Model Animals a: model animal myocardium pathologic score was 3, large area of myocardial cells necrosis and dissolution; b: 40 μg/kg testing drug group, myocardial pathologic score was 1, most of the myocardial cells were normal, there was local myocardial cytoplasm dissolution in sporadic myocardial cells; c: 20 μg/kg testing drug group, myocardial pathologic score was 1, most of the myocardial cells were normal, there was local myocardial cytoplasm dissolution in sporadic myocardial cells; d: 130 μg/kg testing drug group, myocardial pathologic score was 1.5, vacuole degeneration was seen in small cluster of myocardial cells.

TABLE 13

Effect of rhNRG-1 β on myocardial pathologic changes of model animals (I)

| Group | Drug administration | Pathologic scoring |
|---|---|---|
| Normal group (n = 6) |  | 0.00 ± 0.00** |
| Model group (n = 6) | iv qd × 10 d | 2.33 ± 0.26 |
| rhNRG-1 β 40 μg/kg (n = 6) | iv qd × 10 d | 0.33 ± 0.41** |
| rhNRG-1 β 20 μg/kg (n = 6) | iv qd × 10 d | 1.17 ± 0.93* |
| rhNRG-1 β 10 μg/kg (n = 6) | iv qd × 10 d | 1.83 ± 0.41* |

*p < 0.05;
**p < 0.01 when comparing with that of the model animal group

TABLE 14

Effect of rhNRG-1 β on myocardial pathologic changes of model animals (II)

| Group | Drug administration | Pathologic scoring |
|---|---|---|
| Normal group (n = 6) |  | 0 ± 0** |
| Model animal group (n = 6) | iv qd × 10 d | 2.75 ± 0.274 |
| rhNRG-1 β 40 μg/kg (n = 6) | iv qd × 10 | 0.583 ± 0.204** |
| rhNRG-1 β 20 μg/kg (n = 6) | iv qd × 10 d | 1.667 ± 0.931* |
| rhNRG-1 β 10 μg/kg (n = 6) | iv qd × 10 d | 2.167 ± 0.516* | p < 0.05;
**p < 0.01, when comparing with that of the model animal group,

8.5 Effect of rhNRG-1 β on Serum cTnT of Model Animals

After the drug administration, serum cTnT content reduced significantly in every group animals, serum cTnT of high, medium and low dosage level groups was significant lower than that of the model group (P<0.001). Results of the two experiments were coincidence (Tables 15 and 16).

TABLE 15

Effect of rhNRG-1 β on serum cTnT of model animals (I)

| Group | Drug administration | cTnT (ng/ml) |
|---|---|---|
| Normal group (n = 5) |  | 0.001 ± 0.000** |
| Model group (n = 6) | iv qd × 10 d | 0.205 ± 0.072 |
| rhNRG-1 β 40 μg/kg (n = 6) | iv qd × 10 d | 0.025 ± 0.011** |
| rhNRG-1 β 20 μg/kg (n = 6) | iv qd × 10 d | 0.031 ± 0.006** |
| rhNRG-1 β 10 μg/kg (n = 6) | iv qd × 10 d | 0.074 ± 0.024** |

**p < 0.001 when comparing with that of the model group

TABLE 16

Effect of rhNRG-1 β on serum cTnT of model animals (II)

| Group | Drug administration | cTnI (ng/ml) |
|---|---|---|
| Normal group (n = 6) |  | 0.433 ± 0.079** |
| Model group (n = 6) | iv qd × 10 d | 20.525 ± 20.638 |
| rhNRG-1 β 40 μg/kg (n = 6) | iv qd × 10 | 0.874 ± 0.108** |
| rhNRG-1 β 20 μg/kg (n = 6) | iv qd × 10 d | 1.677 ± 0.589** |
| rhNRG-1 β 10 μg/kg (n = 6) | iv qd × 10 d | 8.342 ± 13.537** |

**p < 0.001 when comparing with that of the model animal group

8.6 Effect of rhNRG-1 β on Heart Size of Model Animals

Table and 18 showed results of the two experiments. There was no significant change in heart physical parameters of the testing drug groups and the difference was not significant statistically between the groups (P>0.05).

TABLE 17

Effect of rhNRG-1 β on heart size of model animals (I)

| Group | Drug administration | Heart weight/body weight | Left ventricle wall thickness(mm) |
|---|---|---|---|
| Normal group (n = 20) |  | 0.0032 ± 0.0002 | 2.01 ± 0.07** |
| Model animal group (n = 6) | iv qd × 10 d | 0.0031 ± 0.0001 | 1.717 ± 0.154 |
| rhNRG-1 β 40 μg/kg (n = 16) | iv qd × 10 d | 0.0031 ± 0.0002 | 1.813 ± 0.12 |
| rhNRG-1 β 20 μg/kg (n = 18) | iv qd × 10 d | 0.0032 ± 0.0001 | 1.789 ± 0.133 |
| rhNRG-1 β 10 μg/kg (n = 13) | iv qd × 10 d | 0.00301 ± 0.0002 | 1.773 ± 0.115 |

**p < 0.01, when comparing with that of the model animal group

TABLE 18

Effect of rhNRG-1 β on heart size of model animals (II)

| Group | Drug administration | Heart weight/body weight | Left ventricular wall thickness (mm) |
|---|---|---|---|
| Normal group (n = 20) |  | 0.00310 ± 0.000 | 2.19 ± 0.2** |
| Model group (n = 10) | iv qd × 10 d | 0.00298 ± 0.000 | 2.065 ± 0.17 |
| rhNRG-1 β 40 μg/kg (n = 18) | iv qd × 10 | 0.00297 ± 0.000 | 2.06 ± 0.2 |
| rhNRG-1 β 20 μg/kg (n = 19) | iv qd × 10 d | 0.00303 ± 0.000 | 2.15 ± 0.24 |
| rhNRG-1 β 10 μg/kg g (n = 16) | iv qd × 10 d | 0.00307 ± 0.000 | 2.18 ± 0.21 |

**p < 0.01, when comparing with that of the model animal group

9. Conclusion 40, 20 and 10 μg/kg of rhNRG-1 β could significantly improved the survival rate, reaching 85%, 90% and 60% respectively when comparing with that of 15% survival rate of the model group; dp/dt, −dp/dt and LVPmax of the high, medium and low dosage level group were significantly increased, dp/dt was 5954±689, 6107±418, 4875±636 respectively, −dp/dt was −4794±954, −4323±457, −3672±884 respectively, and LVPmax was 165.7±22.7, 156.1±17.7, 145±15.2 respectively, there was significant difference when comparing with that of the control group (P<0.001), in addition, dp/dt, −dp/dt and LVPmax of the 40 and 20 μg/kg dosage group differed significantly from those of the 10 μg/kg group (<0.05) and was somewhat dose dependent; all the three-dosage levels of 40, 20 and 10 μg/kg rhNRG-1 β could effectively alleviate the severity of myocardial damage in the model animal, reduce serum troponin T (cTnT) content, being 0.025±0.011, 0.031±0.006 and 0.074±0.024 respectively; when comparing with the 0.205±0.072 of the model animal group, there was significant difference. (P<0.01).

Results of the experiment showed that rhNRG-1 β could effectively treat toxic myocardial injury cause by Adriamycin in rat through reduced serum release of cTnT and myocardial fiber necrosis, improved contraction function of the heart and reduced animal mortality.

Example 4

Therapeutic Effect of rhNRG-1 β on Acute Myocardial Injury Caused by Viral Infection in Mice 1. Abstract Objectives To study therapeutic effect of rhNRG-1 β on acute myocardial injury caused by viral (Coxsackie B3) infection. Method Mmice acute viral myocarditis model was established through intra-abdominal injection of Coxsackie B3 virus ($CVB_3$). The model animals were randomly divided into groups, i.e., normal control group, model group, testing drug group with 20 animals in each group. Three dosage level of 30, 15 and 7.5 μg/kg of rhNRG-1 β was established and injection into the tail vein was carried out at the same day, for consecutive 5 days. During the experiment, animal survival rate was monitored. Heart function test (echocardiograph) was performed at the $7^{th}$ day and killed the animals at the $8^{th}$ day, serum was extracted for troponin I (cTnI) level determination and heart pathologic examination performed. Results EF value (90.2±2.5%, 86.0±2.9%) and FS value (55.7±2.1%, 50.7±4.3%) of both the 30 μg/kg and 15 μg/kg group increased significantly; there was significant difference when comparing with those of the model group (P<0.01), LVDd value (0.187±0.006, 0.189±0.008) and LVDs value (0.085±0.009, 0.099±0.027) were significantly lower than those of the model group (0.208±0.015, 0.142±0.020) (P<0.05); rhNRG-1 β could alleviate the severity of myocardial pathologic injury, effectively reduced serum troponin (cTnI) level, cTnI of 30 μg/kg dosage group (7.98±6.07 ng/ml) and 15 μg/kg group (19.43±10.76 ng/ml) were significantly lower than that of the model group (44.44±12.39 ng/ml), the difference between them was significant statistically (P<0.001, P<0.005); 30 μg/kg of rhNRG-1 β could significantly improved survival rate of the model animals, reaching 80%, P<0.05. Conclusion Certain dosage of rhNRG-1 β could effective threat acute myocardial injury caused by viral infection.

2. Objectives of the Experiment

To study therapeutic effect of rhNRG-1 β on acute myocardial injury caused by viral infection in mice and to find out optional effective dosage.

3. Testing Drug rhNRG-1 β, provided by Zensun (Shanghai) Science & Technology Development. Batch number: 200110006-2 Titer: 5000 u; purity:>95% (HPLC-C8).

4. Experiment Animal 4.1 Species, source and certificate of competency: 4-week old purebred BALB/C mice, provided by Experiment Animal Department of Fudan University, Number of certificate of animal competency: Yi Dong Zi 22-9.

4.2 Body weight and gender: 10-12 g, male.

4.3 Animal number in each group: 20 animals in each experimental group, 10 in the normal control group.

5. Virus

Coxsackie Virus B3, $CVB_3$, Nancy strain, provided by Ministerial Viral Heart Disease Laboratory (Shanghai Municipal Cardiovascular Diseases Institute).

6. Reagents and Equipment 6.1 Echocardiography device, Hewlett Packard sonos 5500; type of the probe: S12';
6.2 Immuno-Assay System OpusS Plus, produced by Behring Diagnostic Inc. for determining serum troponin I(cTnI), batch number: CTE8;
6.3 Precise electronic balance, KERN 822;
6.4 Water for injection, Zang Jiang Andus Bioproduct Co Ltd, 10×5 ml, batch number: 0112180;
6.5 Epilating agent, 8% sodium sulfide, GuangDong XiLong Chemical Plant, batch number: 010622.

7. Method of the Experiment 7.1 Experiment Grouping

Normal control group, model group, testing drug group and placebo control group were set up;
Model group was negative control group (n=20): Prepared buffer solution was administered (10 mN PB, 0.2% human serum albumin, 5% mannitol);
Testing drug group (n=20): high, medium and low dosage level of rhNRG-1 β group were divided;
Placebo control group (n=20): Intra-abdominal injection of non-CVB3 freeze-thaw cellular supernatant, 0.2 ml/animal.

7.2 Dosage Set Up, Preparation of Testing Drug, Route of Drug Administration, Times of Drug Administration, Concentration and Volume of the Testing Drug Three-dosage levels of 30, 15 and 7.5 μg/kg of the testing drug group were established based on the results of preliminary experiment. Diluted with preparation buffer solution (10 mM PB, 0.2% human serum albumin, 5% mannitol) to needed concentration. Drug administration of both the testing drug group and the model group was intravenous injection into the tail vein of mice, once every day (qd), for consecutive 5 days, volume of each of the drug administered was 0.2 ml/animal.

7.3 Method of the Experiment 7.3.1 Set Up of Acute Viral Myocariditis Animal Model in Mice 0.2 ml of 100×$TCID_{50}$ $CVB_3$ provided by Zhong Shan Hospital affiliated to Fudan University was injected intra-abdominally and established myocarditis model. Within the following week, the mouse manifested pilo-erection, depilation, emaciation, dullness and death, about half of the tested animals died at the $8^{th}$ day.

7.3.2 Pharmacodynamic Experiment

Intravenous injection of the testing drug into the tail vein was carried out the same day of intra-abdominal viral infection in mice, the injection was performed for consecutive 5 days, animal survival rate was monitored, after completion of the experiment, echocardiograph, myocardial pathologic examination, serum troponin determination were carried out.

7.3.3 Observation Index 7.3.3.1 Heart Function Measurement on Mice

Chest depilating was performed at the $7^{th}$ day of viral injection, then the mouse was fixed on special made fixed mount and echocardiograph was carried out with S12 high-frequency probe, the main index included:
EF: ejection fraction of left ventricle, being major index reflecting ejection function of left ventricle;
FS: shortening fraction of left ventricle, index reflecting contraction function of left ventricle;
LVDd: diastolic maximal inner diameter (cm);
LVDs: systolic minimal inner diameter (cm).

7.3.3.2 Determination of Serum Troponin I (cTnI) in Mice

Severity of myocardial injury was evaluated through determination of the amount of serum cTnI release, with advantage of high specificity and high sensitivity when comparing with other traditional index such as CK, LDH and AST. Therefore, serum cTnI content determination was used as an objective index reflecting the severity of myocardial injury.

At the $8^{th}$ day of viral injection, body weight of the mice was measured and blood withdrawn from the orbit, serum separated, stored in −20° C. refrigerator and serum cTnI determination with luminous reaction carried out.

7.3.3.3 Pathologic Examination of the Myocardium in Mice

The examination was submitted to be carried out by Pathology Department of Shanghai Medical College affiliated to Fudan University.

The survived mice were killed through dislocating the cervical spine, aseptic thoracotomy was performed and the heart extirpated, heart weight measured and put the myocardium into formaldehyde for fixation, embedded in paraffin, consecutive section made and pathologic examination performed, observed inflammatory cells infiltration of the myocardium, degeneration and necrosis. Based on the Principle of New Drug Evaluation Guideline, pathologic scoring criteria was defined as follow:
Score 0: lesion area accounting for 0%;
Score 1: lesion area accounting for 25%;
Score 2: lesion area accounting for 50%;
Score 3: lesion area accounting for 75%;
Score 4: lesion area accounting for 100%;
Scoring could be performed between score 1 and score 2 or between score 2 and score 3, e.g. when lesion area was 80% was scored as score 3.2, 7.3.3.4 Observation on Survival of Mice The death status of model animals in various testing drug group was monitored.

8. Data Processing

Pairing t test of the relevant data was used for data processing.

9. Results 9.1 Effect of rhNRG-1 β on Heart Function of Mice Infected with Virus The results showed that both EF value (67.1±9.9%) and Fs value (32.0±7.2%) were significantly lower than the normal value (EF, 92.5±2.3%/FS, 59.2±3.1%), p<0.05; EF value (90.2±2.5%, 86.0±2.9%) and FS value (55.7±2.1%, 50.7±4.3%) of 30 μg/kg and 15 μg/kg of rhNRG-1 β group increased significantly, there was significant difference when comparing with those of the model group (P<0.01). EF/FS of 7.5 μg/kg group did not have significantly difference from that of the model group (P>0.05).

LVDd value (0.208±0.015 cm) and LVDs value (0.142±0.020 cm) of the model group were significantly higher than that of the normal control group (LVDd, 0.179±0.007 cm/LVDs, 0.073±0.006 cm) and there were significant difference between them (P<0.01). LVDd and LVDs of 30 μg/kg and 15 μg/kg of rhNRG-1 β group were significantly lower than that of the model group (P<0.05), while that of 7.5 μg/kg differed insignificantly from that of the model group (P>0.05). Tables 19 and 20 showed results of the 2 repeated experiments.

TABLE 19

Determination parameters of heart function after 5-day drug administration in mice infected with virus (I)

| Group | Drug administration regime | LVDd (cm) | LVDs (cm) | EF (%) | FS (%) |
| --- | --- | --- | --- | --- | --- |
| Normal control group | | 0.179 ± 0.007** | 0.073 ± 0.006** | 92.5 ± 2.3** | 59.2 ± 3.1** |
| Model group | iv qd × 5 | 0.208 ± 0.015 | 0.142 ± 0.020 | 67.1 ± 9.9 | 32.0 ± 7.2 |
| hNRG-1 β 30 μg/kg | iv qd × 5 | 0.187 ± 0.006** | 0.085 ± 0.009** | 90.2 ± 2.5** | 55.7 ± 2.1** |
| rhNRG-1 β 15 μg/kg | iv qd × 5 | 0.189 ± 0.008* | 0.099 ± 0.027* | 81.3 ± 6.28* | 44.5 ± 8.27* |
| rhNRG-1 β 7.5 μg/kg | iv qd × 5 | 0.191 ± 0.012 | 0.114 ± 0.028 | 78.1 ± 9.3 | 41.7 ± 9.6 |

In each of the above-described data, each group n = 6, through SPSS one-way anova analysis and compare with that of the model group
*P < 0.05
**P < 0.01

TABLE 20

Determination parameters of heart function after 5-day's drug administration in mice infected with virus (II)

| Group | Drug administration regime | LVDd (cm) | LVDs (cm) | EF (%) | FS (%) |
| --- | --- | --- | --- | --- | --- |
| Normal control group | | 0.189 ± 0.008** | 0.069 ± 0.006** | 94.5 ± 0.56** | 63.7 ± 3.01** |
| Model group | iv qd × 5 | 0.232 ± 0.023 | 0.159 ± 0.031 | 63.1 ± 18.47 | 30.3 ± 10.75 |
| rhNRG-1 β 30 μg/kg | iv qd × 5 | 0.196 ± 0.011** | 0.094 ± 0.011** | 87.7 ± 3.76** | 51.8 ± 5.24** |

TABLE 20-continued

Determination parameters of heart function after 5-day's drug administration in mice infected with virus (II)

| Group | Drug administration regime | LVDd (cm) | LVDs (cm) | EF (%) | FS (%) |
|---|---|---|---|---|---|
| rhNRG-1 β 15 µg/kg | iv qd × 5 | 0.201 ± 0.011* | 0.114 ± 0.018* | 81.6 ± 4.59* | 44.9 ± 5.68* |
| hNRG-1 β 7.5 µg/kg | iv qd × 5 | 0.213 ± 0.009 | 0.133 ± 0.015 | 71.9 ± 6.69 | 35.7 ± 5.60 |

In each of the above-described data, each group n = 6, through SPSS one-way anova analysis and compare with that of the model group
*P < 0.05
**P < 0.01

9.2 Effect of rhNRG-1 β on Serum cTnI of Mice Infected by Virus

Results showed that cTnI of the model group (44.44±12.39 ng/ml) was significant higher than that of the control group (3.28±4.55 ng/ml), that of 30 µg/kg of rhNRG-1 β Group (7.98±6.07 ng/ml) was significantly lower than that of the model group (P<0.01); cTnI of 15 µg/kg of rhNRG-1 β group (19.43±10.76 ng/ml) differed significantly from that of the model group (P<0.05), whereas there was no significant difference statistically between cTnI of the 7.5 µg/kg of rhNRG-1 $β_{group}$ (29.05±17.06 ng/ml) and that of the model group. Tables 21 and 22 showed the results of the two experiments.

TABLE 21

Effect of rhNRG-1 β on serum cTnI (ng/ml) content in mice infected by virus (I)

| Group | Drug administration regime | cTnI (ng/ml) Mean ± SD |
|---|---|---|
| Normal control group | | 3.28 ± 4.55** |
| Model group | iv qd × 5 | 44.44 ± 12.39 |
| rhNRG-1 β 30 µg/kg | iv qd × 5 | 7.98 ± 6.07** |
| rhNRG-1 β 15 µg/kg | iv qd × 5 | 19.43 ± 10.76* |
| rhNRG-1 β 7.5 µg/kg | iv qd × 5 | 29.05 ± 17.06 |
| Placebo control group | | 3.75 ± 2.36** |

In each of the above-described data, each group n = 6, through SPSS Nonparametric tests (Independent samples tests) analysis and compare with that of the model group
*P < 0.05
**P < 0.01

TABLE 22

Effect of rhNRG-1 β on serum cTnI (ng/ml) content in mice infected by virus (II)

| Group | Drug administration regime | cTnI (ng/ml) Mean ± SD |
|---|---|---|
| Normal group | | 0.19 ± 0.06** |
| Model group | iv qd × 5 | 34.05 ± 16.50 |
| rhNRG-1 β 30 µg/kg | iv qd × 5 | 0.54 ± 0.53** |
| rhNRG-1 β 15 µg/kg | iv qd × 5 | 15.59 ± 14.94* |
| rhNRG-1 β 37.5 µg/kg | iv qd × 5 | 26.85 ± 15.20 |
| Placebo control group | | 14 ± 0.03** |

In each of the above-described data, each group n = 6, through SPSS Nonparametric tests (Independent samples tests) analysis and compare with that of the model group
*P < 0.05
**P < 0.01

9.3 Effect of rhNRG-1 β on Myocardial Injury of Mice Infected with Virus

Figure 21:
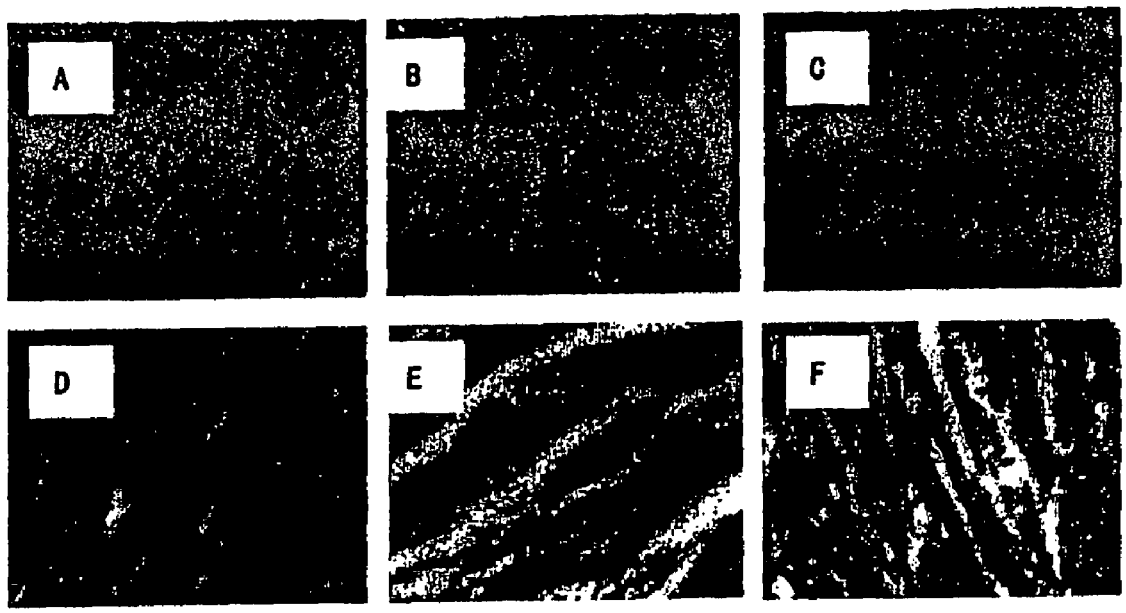
FIG. 21 illustrates effect of rhNRG-1 β S177-Q237 on myocardial pathologic damage in mice infected by virus (I); A: Normal group; B: Model group; C: Placebo control group; D: High dosage level group; E: Medium dosage level group; and F: Low dosage level group.
Figure 22:
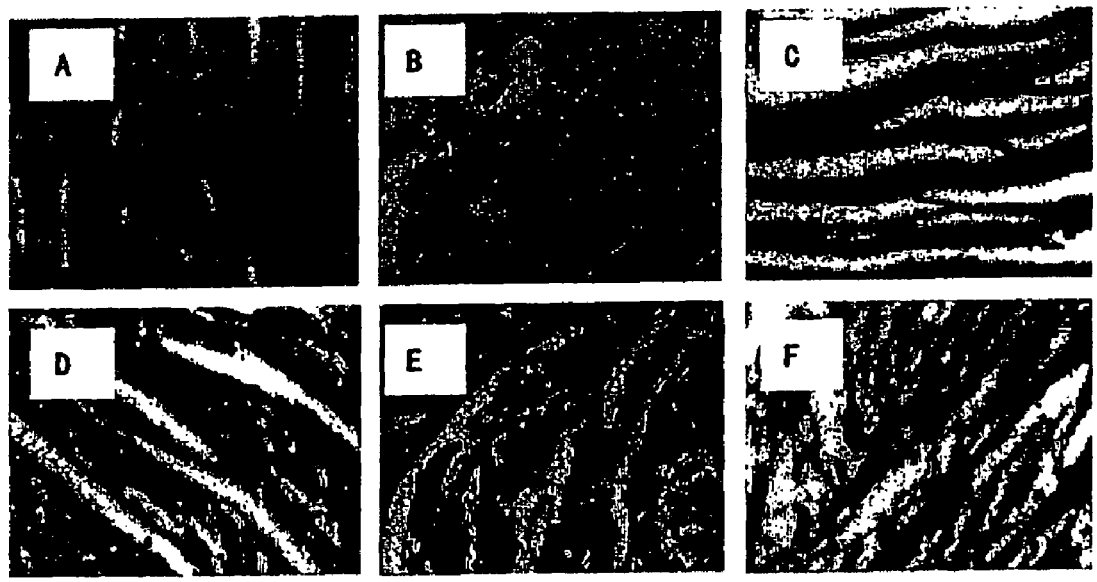
FIG. 22 illustrates effect of rhNRG-1 β S177-Q237 on myocardial pathologic damage in mice infected by virus; A: Normal group; B: Model group; C: Placebo control group; D: High dosage level group; E: Medium dosage level group; and F Low dosage level group.
Figure 23:
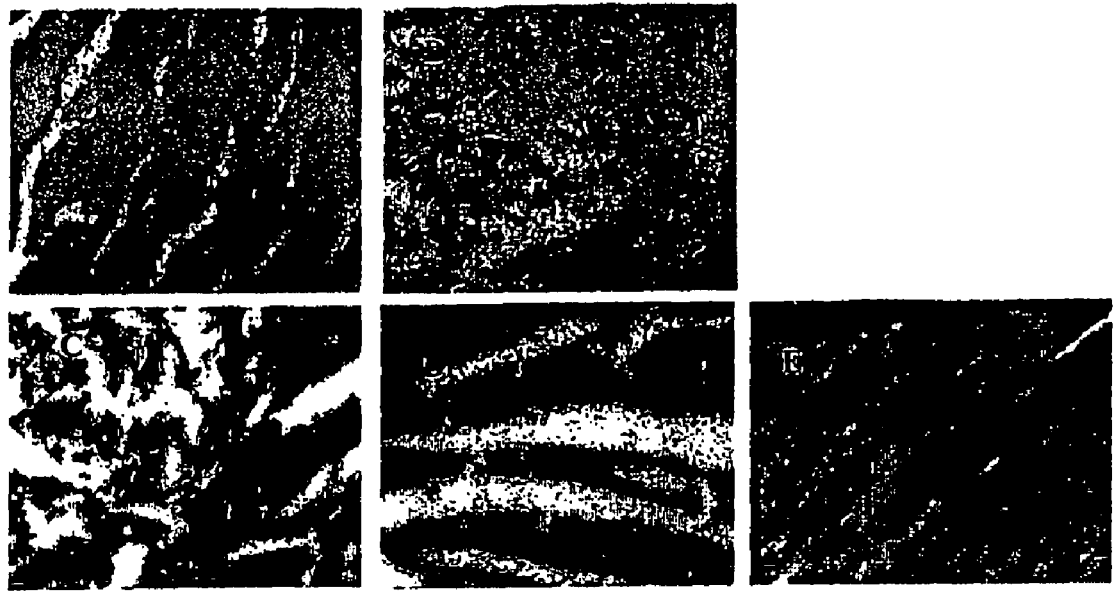
FIG. 23 illustrates effect of rhNRG-1 β S177-Q237 administered for different number of days on myocardial pathologic changes in mice infected by virus (I) (HE stained, 40×); A: Normal control group; B: model group; C: rhNRG-1 β S177-Q237 for 3-day group; D: rhNRG-1 β S177-Q237 for 5-day group; and E: rhNRG-1 β S177-Q237 for 7-day group.

Results of the experiment showed that myocardial pathologic score of the normal group was 0.0±0.00, myocardial pathologic score of the model group was (2.22±0.97), there was significant difference between them (P<0.01). Pathologic score of both the high dosage and medium dosage level of rhNRG-1 β decreased significantly (0.56±0.47 and 0.73±0.58 respectively), and were significantly different from that of the model group (P<0.001), there was no significant difference between that of the low dosage level group and that of the model group (P>0.05). Tables 23 and 24 and FIGS. 21 and 22 showed results of the two experiments.

TABLE 23

Effect of rhNRG-1 β on myocardial pathologic changes in mice infected by virus (I)

| Group | Drug administration regime | Pathologic score Mean ± SD |
|---|---|---|
| Normal control group (n = 10) | | 0.00 ± 0.00** |
| Model group (n = 10) | iv qd × 5 | 2.22 ± 0.97 |
| rhNRG-1 β 30 µg/kg (n = 17) | iv qd × 5 | 0.56 ± 0.47** |
| rhNRG-1 β 15 µg/kg (n = 13) | iv qd × 5 | 0.73 ± 0.58** |
| rhNRG-1 β 7.5 µg/kg (n = 10) | iv qd × 5 | 1.52 ± 0.74 |
| Placebo control group (n = 10) | | 0.00 ± 0.00** |

In each of the above-described data, each group n = 6, through SPSS Nonparametric tests (Independent samples tests) analysis and compare with that of the model group
*P < 0.05
**P < 0.01

TABLE 24

Effect of rhNRG-1 β on myocardial pathologic changes in mice infected by virus (II)

| Group | Drug administration regime | Pathologic score Mean ± SD |
|---|---|---|
| Normal control group (n = 10) | | 0.00 ± 0.00** |
| Model group (n = 10) | iv qd × 5 | 2.03 ± 1.44 |
| rhNRG-1 β 30 µg/kg (n = 17) | iv qd × 5 | 0.23 ± 0.26** |
| rhNRG-1 β 15 µg/kg (n = 13) | iv qd × 5 | 0.57 ± 0.58** |
| rhNRG-1 β 7.5 µg/kg (n = 10) | iv qd × 5 | 1.34 ± 1.16 |
| Placebo control group (n = 10) | | 0.00 ± 0.00** |

In each of the above-described data, each group n = 6, through SPSS Nonparametric tests (Independent samples tests) analysis and compare with that of the model group
*P < 0.05
**P < 0.01

9.4 Effect of rhNRG-1 β on Survival Rate of Mice Infected by Virus

Tables 25 and 26 showed results of the two experiments. One week after injection of the virus, survival rate of mice in the model group was 50% and 55% respectively, while after injection of rhNRG-1 β they raised up to 85% and 80% (30ttg/kg) and 70% and 65% (15 μg/kg).

TABLE 25

Effect of rhNRG-1 β on survival rate of mice infected by virus (I)

| Group | Drug administration | Numbers of survival animals (relative survival rate %) | | | | | | | |
|---|---|---|---|---|---|---|---|---|---|
| | | $1^{st}$ day | $2^{nd}$ day | $3^{rd}$ day | $4^{th}$ day | $5^{th}$ day | $6^{th}$ day | $7^{th}$ day | killed |
| Normal control group (n = 10) | | 10 100% | 10 100% | 10 100% | 10 100% | 10 100% | 10 100% | 10 100% | 10** 100% |
| Model group (n = 20) | iv qd × 5 | 20 100% | 20 100% | 20 100% | 18 90% | 17 85% | 14 70% | 11 55% | 10 50% |
| rhNRG-1 β 30 μg/kg (n = 20) | iv qd × 5 | 20 100% | 20 100% | 20 100% | 20 100% | 20 100% | 18 90% | 17 85% | 16* 80% |
| rhNRG-1 β 15 μg/kg (n = 20) | iv qd × 5 | 20 100% | 20 100% | 20 100% | 20 100% | 19 95% | 17 85% | 14 70% | 13 65% |
| rhNRG-1 β 5 μg/kg (n = 20) | iv qd × 5 | 20 100% | 20 100% | 20 100% | 19 95% | 18 90% | 15 75% | 13 65% | 10 50% |
| Placebo control group (n = 20) | | 20 100% | 20 100% | 20 100% | 20 100% | 20 100% | 20 100% | 20 100% | 20** 100% |

The above described data were processed through SPSS software, Survival Life Tables analysis,
*P < 0.05
**P < 0.01, when comparing with that of the control group

TABLE 26

Effect of rhNRG-1 β on survival rate of mice infected by virus (II)

| Group | Drug administration | Numbers of survival animals (relative survival rate %) | | | | | | | |
|---|---|---|---|---|---|---|---|---|---|
| | | $1^{st}$ day | $2^{nd}$ day | $3^{rd}$ day | $4^{th}$ day | $5^{th}$ day | $6^{th}$ day | $7^{th}$ day | killed |
| Normal control group (n = 10) | | 10 100% | 10 100% | 10 100% | 10 100% | 10 100% | 10 100% | 10 100% | 10** 100% |
| Model group (n = 20) | iv qd × 5 | 20 100% | 20 100% | 20 100% | 18 90% | 15 75% | 13 65% | 10 50% | 10 50% |
| rhNRG-1 β 30 μg/kg (n = 20) | iv qd × 5 | 20 100% | 20 100% | 20 100% | 20 100% | 19 95% | 18 90% | 17 85% | 17* 85% |
| rhNRG-1 β 15 μg/kg (n = 20) | iv qd × 5 | 20 100% | 20 100% | 20 100% | 19 95% | 18 90% | 16 80% | 13 65% | 13 65% |
| rhNRG-1 β 7.5 μg/kg (n = 20) | iv qd × 5 | 20 100% | 20 100% | 20 100% | 18 90% | 17 85% | 14 70% | 11 55% | 10 50% |
| Placebo control group (n = 20) | | 20 100% | 20 100% | 20 100% | 20 100% | 20 100% | 20 100% | 20 100% | 20** 100% |

The above described data were processed through SPSS software, Survival Life Tables analysis,
*P < 0.05
**P < 0.01 when comparing with that of the control group 9. Conclusion EF value (90.2±2.5%, 86.0±2.9%) and FS value (55.7±2.1%, 50.7±4.3%) of 30 μg/kg and 15 μg/kg of rhNRG-1 β groups raised significantly and there was significant difference when comparing with that of the model group (P<0.02), both LVDd value (0.187±0.006, 0.189±0.008) and LVDs value (0.085±0.009, 0.099±0.027) were lower than that of the model group (0.208±0.015, 0.142±0.020), P<0.05; rhNRG-1 β could alleviate the severity of myocardial pathologic damage of model group animals, effectively reduced serum troponin I (cTnI) level, cTnI content of 30 μg/kg dosage level group (7.98±6.07 ng/ml) and 15 μg/kg dosage level group (19.43±10.76 ng/ml) were significantly lower than that of the model group (44.44±12.39 ng/ml) and there was significant difference between them (P<0.001, P<0.005); 30 μg/kg of rhNRG-1 β could significantly improve survival rate of model group animals and reached 80% when comparing with the 50% survival rate of the model group animals, P<0.05.

Results of the experiment showed that 30 μg/kg dosage level of rhNRG-1 β could effectively treat acute myocardial injury caused by viral infection in mice.

Example 5

Observation on Therapeutic Effect of rhNRG-1 β on Acute Myocardial Injury of Mice Caused by Viral Infection (II)

1. Abstract

Objectives To study the effective time of drug administration of rhNRG-1 β in the treatment of acute myocardial injury in mice caused by viral infection. Method Acute myocardial injury animal model was established through intra-abdominal injection of Coxsacki $B_3$ virus ($CVB_3$) in mice. The model animals were randomly divided into groups, i.e., normal control group, model group, testing drug group, 20 animals was assigned to each group. 30 μg/kg of rhNRG-1 β was injected into the tail vein for consecutive 3, 5 and 7 days respectively. During the experiment, animal survival rate was monitored, echocardiograph was performed at the $7^{th}$ day and the animals were killed at the $8^{th}$ day, serum separated for cTnI level determination, heart pathohistological examination carried out. Results Consecutive injection of 30 μg/kg of rhNRG-1 β for 3, 5 and 7 days could raise the EF/FS value and there was significant difference (P<0.001) in comparing the EF/FS value of 5-day and 7-day testing drug groups (86.8±4.4%/51.9±5.8%, 87.0±3.3%/51.8±5.1%) with the EF/FS value of the model group (66.5±5.6/31.8±3.7), the LVDs value of the 5 and 7-day testing drug group decreased significantly (being 0.090±0.011, 0.092±0.012 cm respectively) and there was significant difference (P<0.01) when comparing with that of the model group (0.133±0.012); rhNRG-1 β could alleviate the severity of myocardial pathological damage, effectively reduced serum troponin I (cTnI) level of the model animals, the cTnI of 5-day testing drug group (1.06±1.32 ng/ml) and of 7-day testing drug group (1.05±1.2 ng/ml) was significantly lower than that of the model group (23.54±16.96 ng/ml) P<0.01; consecutive 5 and 7-day injection of rhNRG-1 β could significantly improved the animal survival rate, reaching 85% when comparing with the 50% survival rate of the model animals, P<0.05. Conclusion 30 μg/kg of rhNRG-1 β injected for consecutive 5 days could effectively treat the acute myocardial injury in mice caused by viral infection.

2. Objectives

To make clear the effective time of drug administration of rhNRG-1 β in the treatment of mice acute myocardial injury caused by viral infection.

3. Testing Drug rhNRG-1 β, provided by Zensun (Shanghai) Science & Technology Development. Batch number: 200110006-2, Titer: 500 u; purity:>95% (HPLC-C8).

5. Experiment Animal 5.1 Species, source and certificate of competency: 4-week old purebred BALB/C mice, provided by Experiment Animal Department of Fudan University, Number of certificate of animal competency: Yi Dong Zi 22-9.

5.2 Body weight and gender: 13-15 g, male.

5.3 Animal number in each group: 20 animals in each experimental group, 10 in the normal control group.

5. Virus

The same as that described in the previous section.

6. Reagents and Equipment

The same as that described in the previous section.

10. Method of the Experiment 10.1 Experiment Grouping

Normal mice control group, model group and testing drug group were set up;

Normal mice control group (n=10);

Model group (n=20): Prepared buffer solution was injected;

Testing drug group (n=20): 30 μg/kg of rhNRG-1 β was administered for 3, 5 and 7 consecutive days as three difference therapeutic courses with 20 animals assigned for each group;

Placebo control group (n=20): Intra-abdominal injection of non-CVB3 freeze-thaw cellular supernatant, 0.2 ml/animal.

10.2 Dosage Set Up, Preparation of Testing Drug, Route of Drug Administration, Times of Drug Administration, Concentration and Volume of the Testing Drug rhNRG-1 β was diluted with preparation buffer solution (10 mM PB, 0.2% human serum albumin, 5% mannitol to needed concentration;

Three drug administration groups were set up, intravenous injection for consecutive 3-day, 5-day and 7-day, drug volume for each dose was 0.2 ml/animal;

Drug administration of the model group was intravenous injection into the tail vein of mice, once every day (qd), for consecutive 7 days, drug volume for each dose was 0.2 ml/animal.

7.3 Method of the Experiment 7.3.1 Set Up of Acute Viral Myocariditis Animal Model in Mice 0.2 ml of 100×$TCID_{50}$ $CVB_3$ provided by Zhong Shan Hospital affiliated to Fudan University was injected intra-abdominally and established myocarditis model. Within the following week the mouse manifested pilo-erection, depilation, emaciation, dullness and death, about half of the tested animals died at the $8^{th}$ day.

7.3.2 Pharmacodynamic Experiment

The same as that described in the previous section.

7.3.3 Observation Index

The same as that described in the previous section.

8. Data Processing

Pairing t test of the relevant data was used for the data processing.

9. Results 9.1 Effect of rhNRG-1 β Administered for 3, 5 and 7 Days on Heart Function of Mice Infected by Virus Results showed that EF/Fs value (66.5±5.6%/31.8±3.7%) was significantly lower than that of the normal group (93.5±0.9%/68.1±1.3%), the difference was significant statistically ($P<0.01$). EF/FS value of 5 and 7 consecutive-day of rhNRG-1 β injection (86.8±4.4%/51.9±5.8%, 87.0±3.3%/51.8±5.1%) differed significantly from that of the model group ($P<0.001$).

EF value of 3 consecutive days of rhNRG-1 β injection raised again (73.1±6.6%), however without significant difference when comparing with that of the model group ($P<0.05$).

LVDs value (0.133±0.012 cm) was higher than that of the normal group (0.059±0.006 cm) and there was significant difference between them ($P<0.01$). LVDs value of rhNRG-1 β administered for 5 days and for 7 days group was significantly reduced (0.090±0.011, 0.092±0.012 cm respectively), and differed significantly from that of the model group ($P<0.001$). LVDs value of rhNRG-1 β administered for 3-day group (0.123±0.012 cm) differed insignificantly from that of the model group ($P<0.05$). Table-27 and 17-28 showed results of the two experiments.

TABLE 27

Effect of rhNRG-1 β administered for different number of days on heart function of mice infected by virus (I)

| Group | Drug administration regime | LVDd(cm) | LVDs(cm) | EF(%) | FS(%) |
| --- | --- | --- | --- | --- | --- |
| Normal control group | | 0.179* ± 0.007 | 0.059** ± 0.006 | 93.5** ± 0.9 | 68.1** ± 1.3 |
| Model group | iv qd × 7 | 0.194 ± 0.012 | 0.133 ± 0.012 | 66.5 ± 5.6 | 31.8 ± 3.7 |
| rhNRG-1 β 30 μg/kg | iv qd × 3 | 0.194 ± 0.008 | 0.123 ± 0.012 | 73.1 ± 6.6 | 36.7 ± 4.7 |
| rhNRG-1 β 30 μg/kg | iv qd × 5 | 0.187 ± 0.006 | 0.090** ± 0.011 | 86.8** ± 4.4 | 51.9** ± 5.8 |
| rhNRG-1 β 30 μg/kg | iv qd × 7 | 0.192 ± 0.008 | 0.092** ± 0.012 | 87.0** ± 3.3 | 51.8** ± 5.1 |

In each of the above-described data, each group n = 6, through SPSS one-way anova analysis and compare with that of the model group

*$P < 0.05$

**$P < 0.01$

TABLE 28

Effect of rhNRG-1 β administered for different number of days on heart function of mice infected by virus (II)

| Group | Drug administration regime | LVDd(cm) | LVDs(cm) | EF(%) | FS(%) |
| --- | --- | --- | --- | --- | --- |
| Normal control group | | 0.189** ± 0.008 | 0.080** ± 0.007 | 90.9** ± 2.6 | 57.5** ± 3.5 |
| Model group | iv qd × 7 | 0.206 ± 0.008 | 0.126 ± 0.006 | 75.4 ± 5.2 | 39.0 ± 4.3 |
| rhNRG-1 β 30 μg/kg | iv qd × 3 | 0.211 ± 0.016 | 0.121 ± 0.016 | 81.0 ± 5.4 | 43.9 ± 5.1 |
| rhNRG-1 β 30 μg/kg | iv qd × 5 | 0.199 ± 0.000 | 0.100* ± 0.014 | 85.8** ± 4.205 | 50.0** ± 6.350 |
| rhNRG-1 β 30 μg/kg | iv qd × 7 | 0.194 ± 0.017 | 0.092** ± 0.008 | 87.283** ± 1.694 | 52.367** ± 1.847 |

In each of the above-described data, each group n = 6, through SPSS one-way anova analysis and compare with that of the model group

*$P < 0.05$

**$P < 0.01$ 9.2 Effect of rhNRG-1 β on Serum cTnI of Mice Infected by Virus

Results showed that mean of cTnI of the normal group (0.12±0.03 ng/ml)and mean of cTnI of the model group raised significantly (23.54±16.96 ng/ml) and there was significant difference between them (P<0.001). cTnI value of rhNRG-1 β administered for both 5-day and 7-day group reduced significantly (being 1.06±1.32 ng/ml, 1.05±1.20 ng/ml respectively), and differed significantly from that of the model group (P<0.001), the difference was insignificant between the 3-day drug administration group and the model group (P>0.05). Tables 29 and 30 showed the results of the two experiments.

TABLE 29

Effect of rhNRG-1 β on serum cTnI (ng/ml) in mice infected by virus (I)

| Group n = 9) | Drug administration regime | cTnI (ng/ml) Mean ± SD |
|---|---|---|
| Normal control group | | 0.12 ± 0.03** |
| Model group | iv qd × 7 | 23.54 ± 16.96 |
| rhNRG-1 β 30 µg/kg | iv qd × 3 | 13.37 ± 9.53 |
| rhNRG-1 β 30 µg/kg | iv qd × 5 | 1.06 ± 1.32** |
| rhNRG-1 β 30 µg/kg | iv qd × 7 | 1.05 ± 1.20** |

Each of the above group was analyzed by Nonparametric tests (Independent samples tests) of SPSS software, when comparing with that of the model group,
*P < 0.05
**P < 0.01

TABLE 30

Effect of rhNRG-1 β on serum cTnI (ng/ml) in mice infected by virus (II)

| Group n = 8) | Drug administration regime | cTnI (ng/ml) Mean ± SD |
|---|---|---|
| Normal control group | | 0.15 ± 0.03** |
| Model group | iv qd × 7 | 30.13 ± 21.75 |
| rhNRG-1 β 30 µg/kg | iv qd × 3 | 12.32 ± 18.36 |
| rhNRG-1 β 30 µg/kg | iv qd × 5 | 0.44 ± 0.24** |
| rhNRG-1 β 30 µg/kg | iv qd × 7 | 0.51 ± 0.28** |

Each of the above group was analyzed by Nonparametric tests (Independent samples tests) of SPSS software, when comparing with that of the model group,
*P < 0.05
**P < 0.01

9.3 Effect of rhNRG-1 β Administered for Different Number of Days on Myocardial Pathologic Injury of Mice Infected with Virus Results of the experiment showed that pathologic score of the normal group was 0.0±0.00, pathologic score of the model group was increased (1.44±1.19), there was significant difference between them (P<0.01), pathologic score of rhNRG-1 β administered for 5-day and 7-day groups reduced significantly (being 0.11±0.14 and 0.13±0.13 respectively) and differed significantly from that of the model group (P<0.01). There was improvement of myocardial injury of the 3-day drug administration group as well (0.33±0.155) and there was significant difference when comparing with that of the model group, however, improvement of the myocardial cells of the 5-day drug administration group was markedly better than that of the 3-day drug administration group and there was significant difference between them (P<0.01), while there was no significant difference in pathologic scoring between 5-day and 7-day drug administration group.

Figure 24:
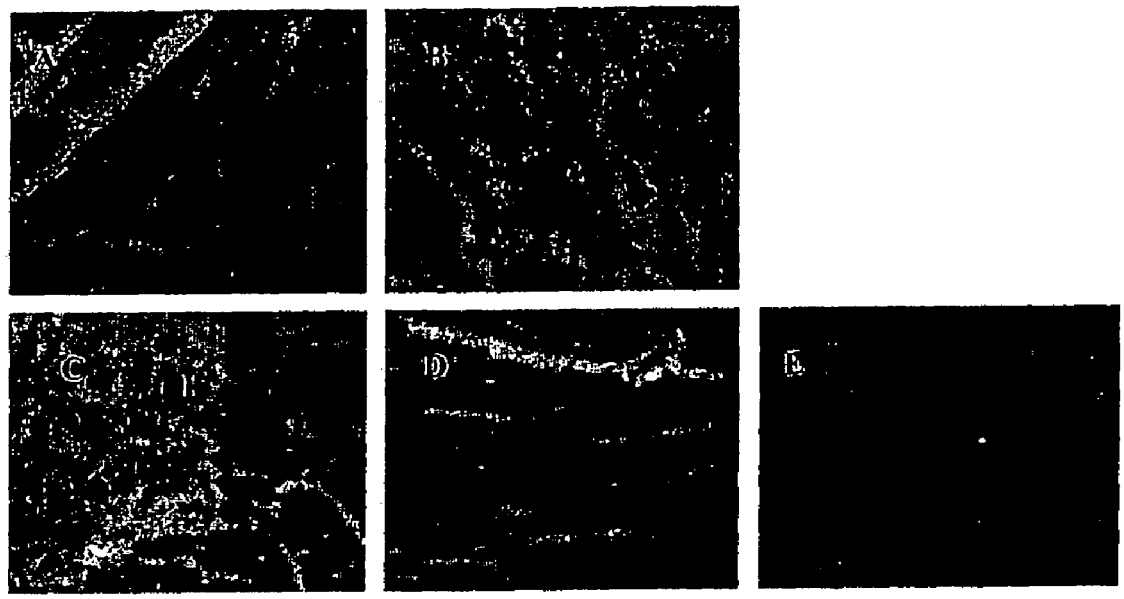
FIG. 24 illustrates effect of rhNRG-1 β administered for different number of days on myocardial pathologic changes in mice infected by virus (II) (HE stained, 40×); A: Normal control group; B: model group; C: rhNRG-1 β S177-Q237 for 3-day group; D: rhNRG-1 β for 5-day group; and E: rhNRG-1 β S177-Q237 for 7-day group.

Tables 31, 32 and FIGS. 21 and 24 showed results of the two experiments.

TABLE 31

Effect of rhNRG-1 β administered for different number of days on myocardial pathologic changes in mice infected by virus (I)

| Group | Drug administration regime | Pathologic score Mean ± SD |
|---|---|---|
| Normal control group | | 0.00 ± 0.00** |
| Model group | iv qd × 7 | 1.44 ± 1.19 |
| rhNRG-1 β 30 µg/kg | iv qd × 3 | 0.33 ± 0.155* |
| rhNRG-1 β 30 µg/kg | iv qd × 5 | 0.11 ± 0.140** |
| rhNRG-1 β 30 µg/kg | iv qd × 7 | 0.13 ± 0.132** |

Each of the above group was analyzed by Nonparametric tests (Independent samples tests) of SPSS software, when comparing with that of the model group,
*P < 0.05
**P < 0.01

TABLE 32

Effect of rhNRG-1 β administered for different number of days on myocardial pathologic changes in mice infected by virus (II)

| Group (n = 10) | Drug administration regime | Pathologic score Mean ± SD |
|---|---|---|
| Normal control group | | 0.00 ± 0.00** |
| Model group | iv qd × 7 | 1.86 ± 1.20 |
| rhNRG-1 β 30 µg/kg | iv qd × 3 | 0.55 ± 0.476* |
| rhNRG-1 β 30 µg/kg | iv qd × 5 | 0.17 ± 0.157** |
| rhNRG-1 β 30 µg/kg | iv qd × 7 | 0.19 ± 0.168** |

Each of the above group was analyzed by Nonparametric tests (Independent samples tests) of SPSS software, when comparing with that of the model group,
*P < 0.05
**P < 0.01

9.4 Effect of rhNRG1 β on Survival Rate of Mice Infected by Virus

Tables 33 and 34 showed results of the two experiments, survival rate of mice in the model group was 50% and 55% respectively, while that of rhNRG-1 β administered for both 5-day and 7-day group raised up to 85% and 80% and there was significant difference when comparing with that of the model group, P<0.05. Survival rate of the 3-day group raised to 65% and 75%, however, there was no significant difference when comparing with that of the model group (P<0.05).

TABLE 33

Effect of rhNRG-1 β administered for different number of days on survival rate in mice infected by virus (I)

| Group | Drug administration | Number of survival animal (relative survival rate %) | | | | | | | |
|---|---|---|---|---|---|---|---|---|---|
| | | 1st day | 2nd day | 3rd day | 4th day | 5th day | 6th day | 7th day | killed |
| Normal control group n = 10 | | 10 100% | 10 100% | 10 100% | 10 100% | 10 100% | 10 100% | 10 100% | 10** 100% |
| Model group n = 20 | iv qd × 7 | 20 100% | 20 100% | 20 100% | 18 90% | 16 80% | 13 65% | 10 50% | 10 50% |
| rhNRG-1 β 30 µg/kg n = 20 | Iv qd × 3 | 20 100% | 20 100% | 20 100% | 19 95% | 18 90% | 16 80% | 14 70% | 13 65% |
| rhNRG-1 β 30 µg/kg n = 20 | iv qd × 5 | 20 100% | 20 100% | 20 100% | 20 100% | 19 95% | 19 95% | 18 90% | 17* 85% |
| rhNRG-1 β 30 µg/kg n = 20 | iv qd × 7 | 20 100% | 20 100% | 20 100% | 20 100% | 20 100% | 19 90% | 19 90% | 17* 85% |

Each of the above group was analyzed by Survival Life Tables of SPSS software, when comparing with that of the model group,
*P < 0.05
**P < 0.01

TABLE 34

Effect of rhNRG-1 β administered for different number of days on survival rate in mice infected by virus (II)

| Group | Drug administration | Number of survival animals (relative survival rate %) | | | | | | | |
|---|---|---|---|---|---|---|---|---|---|
| | | 1st day | 2nd day | 3rd day | 4th day | 5th day | 6th day | 7th day | killed |
| Normal group n = 10 | | 10 100% | 10 100% | 10 100% | 10 100% | 10 100% | 10 100% | 10 100% | 10** 100% |
| Model group n = 20 | iv qd × 7 | 20 100% | 20 100% | 20 100% | 18 90% | 17 85% | 14 70% | 12 60% | 12 60% |
| rhNRG-1 β 30 µg/kg n = 20 | iv qd × 3 | 20 100% | 20 100% | 20 100% | 20 100% | 19 95% | 16 80% | 15 75% | 15 75% |
| rhNRG-1 β 30 µg/kg n = 20 | iv qd × 5 | 20 100% | 20 100% | 20 100% | 20 100% | 19 95% | 19 95% | 18 90% | 18* 90% |
| rhNRG-1 β 30 µg/kg n = 20 | iv qd × 7 | 20 100% | 20 100% | 20 100% | 20 100% | 20 100% | 19 95% | 18 90% | 18* 90% |

Each of the above group was analyzed by Survival Life Tables of SPSS software, when comparing with that of the model group,
*P < 0.05
**P < 0.01

10 Conclusion

30 µg/kg of rhNRG-1 β intravenously injected for consecutive 3, 5 and 7 days could all raise the EF/FS value, EF/FS value of drug administration for 5 and 7 days groups (86.8±4.4%/51.9±5.8%, 87.0±3.3%/51.8±5.1%) differed significantly from EF/FS value of the model group (66.5±5.6/31.8±3.7) (P<0.01), LVDs of both the 5 and 7 days groups reduced significantly (being 0.090±0.011 and 0.092±0.012 cm respectively) and differed significantly from that of the model group (0.133±0.012) (P<0.01); rhNRG-1 β could alleviate the severity of myocardial pathologic damage in model animals, effectively reduced serum troponin I (cTnI) level, cTnI of drug administration for 5-day group (1.06±1.32 ng/ml) and for 7-day group (1.05±1.2 ng/ml) were significantly lower than that of the model group (23.54±16.96 ng/ml), (P<0.01); rhNRG-1 β intravenously injected for consecutive 5 days and 7 days could significant raised survival rate of the model animals, reaching 85%. P<0.05.

Results of the experiment demonstrated that 30 µg/kg of rhNRG-1 β administered for consecutive 5 days could effectively treat the acute myocardial injury in mice infected by virus.

Example 6

Therapeutic Effect of rhNRG-1 β on Congestive Heart Failure Caused by Inferior Vena Cava Constriction 1. Abstract Objectives To study therapeutic effect of rhNRG-1 β on congestive heart failure caused by inferior vena cava constriction in dog. Methods After about 1 week of constriction of inferior vena cava by 50%, EF value reduced by about 20% or cardiac output reduced by 20% determined by echocardiograph, demonstrating that stable low output, congestive heart failure animal model was established. Then randomly divided the animals into groups with 6 dogs for each group, three dosage level of rhNRG-1 β, i.e., 1, 3 and 10 µg/kg, was intravenously injected daily for consecutive 5 days. Heart function (echocardiography) determination was performed after the drug administration; various hemodynamic parameters in model animals were analyzed through cervical vein and carotid artery catheterization respectively. Results All of the three dosage level of rhNRG-1 β (1, 3 and 10 µg/kg) administrated for consecutive 5 days could raise EF/FS value and cardiac output (CO) of model animals, there were significant difference between those value prior to and after the drug administration and those of the model group ($P<0.05$, $P<0.01$); 1, 3 and 10 µg/kg of rhNRG-1 β could effectively raise dp/dt of left ventricle in model animals, there was significant difference when comparing with that of the model group ($P<0.01$), could effectively raised LVPmax of the model animals, reduced LVPmin value and $P<0.04$ when comparing with those of the model group, whereas effect on the right ventricle was not apparent. Conclusion rhNRG-1 β could effectively treat congestive heart failure caused by constriction of the inferior vena cava in dog.

2. Objectives

To demonstrate therapeutic effect of rhNRG-1 β on congestive heart failure caused by constriction of the inferior vena cava in dog.

3. Testing Sample rhNRG-1 β, provided by Zensun (Shanghai) Science & Technology Development. Batch number: 200110006-2; Concentration: 500 µg/ampule; Titer: 5000 u/ampule; Purity: >95% (HPLC-C8).

6. Experiment Animal 6.1 Species, source and certificate of competency: crossbred dog, provided by Zhong Shan Hospital of Fudan University, being eligible guarantied by Experiment Department of Fudan University.

6.2 Body weight and gender: 13-18 kg, male.

6.3 Animal number in each group: 6 animals in each experimental group.

5. Materials and Equipment 5.1 Echocardiography device, Hewlett Packard sonos 5500; type of the probe: S4

5.2 Water for injection, Zang Jiang Antus Bioproduct Co Ltd, 10×5 ml, batch number: 0112180;

5.3 High-frequency electric knife, Shanghai Hu Tong electronic equipment factory, GD350-D; 0

5.4 Electrocardiography recorder, Nihon Kohden ECG-6511;

5.5 Monitoring electrode, Ludlow Company of Canada, model: MT-200;

5.6 Physiology recorder, Equipment Research Center of Shanghai Medical University, SMUP-B;

5.7 Electric ventilator, Shanghai No. 4 Medical Equipment Factory;

5.8 Trifid balloon floating catheter, Edwards 114F7.

6 Method of the Experiment 6.1 Experiment Grouping

Pseudo-operation group, model group and testing drug group were set up.

Pseudo-operation group (n=6): only thoracotomy but without constriction of the inferior vena cava were carried out.

Model group (n=6): Prepared buffer solution was injected after the establishment of heart failure model.

Testing drug group: rhNRG-1 β was injected after the establishment of heart failure model.

6.2 Dosage Set Up, Preparation of Testing Drug, Drug Administration Regime

High, medium and low dosage level of 1, 3 and 10 µg/kg respectively of rhNRG-1 β was diluted with preparation buffer solution (vehicle) to needed concentration, intravenous injection once everyday for consecutive 5 days.

Preparation buffer solution was injected intravenously once daily for consecutive 5 days for the model group.

Volume of the drug administered was 0.8 ml/kg body weight.

6.3 Method of the Experiment 6.3.1 Set Up of Heart Failure Caused by Constriction of Inferior Vena Cava Animal Model in Dog 3% pentobarbital sodium (30 mg/kg) was injected into the peripheral vein to anesthetize the dog, then trachea intubated. Aseptic thoracotomized via right chest between the 4 and 5 rib, measured circumference of the inferior vena cava at 3 cm from the right auricle. Selected hard spool with circumference equal to ⅓-½ of that of the inferior vena cava, tighted the spool and the inferior vena cava together with #7 silk thread, drew out the spool, stopped all the bleeding, closed the chest. Bred for 1 week, echocardiography performed according to the amount of ascites, when EF reduced by about 20% or dilatation of the left heart by about 20%, stable low cardiac output congestive heart failure animal model was established. Then intravenous injection of the drug was carried out for consecutive 5 days. Thoracotomy without constricting the inferior vena cava was carried out for the pseudo-operation group.

6.3.2 Pharmacodynamic Experiment

After identifying the establishment of animal model, experiment was carried out according to the animal grouping and drug administration regime.

6.3.3 Observation Index

Heart function index determination was carried out under anesthesia of the dog prior to the operation, prior to and 5-day after the drug administration. Major index included:

EF (Ejection Fraction): heart ejection fraction, i.e., ratio of difference between end diastolic volume of the ventricle (EDV) and end systolic volume of ventricle (ESV) and end diastolic volume of ventricle, being general index used for reflecting pumping function of ventricle; especially reflecting the systolic function;

FS: ventricular short axis shortening rate, being index reflecting contraction function of ventricle, CO: cardiac output, i.e. blood volume ejected by the heart per minute.

6.3.3.2 Hemodynamic Index Determination 7F trifid balloon floating catheter was inserted into the right jugular vein, right auricular pressure, right ventricular pressure, pulmonary pressure and pulmonary wedge pressure were recorded.

6F trifid balloon floating catheter was again inserted into left carotid artery, aorta pressure and left ventricle pressure were recorded with physiology recorder with the following major index: LVPmax, LVPmin, +dp/dt, and −dp/dt.

7. Data Processing

Paring t test or nonparameter test of the collected data with SPSS software was carried out.

8. Results 8.1 Effect of rhNRG-1 β on Heart Function of TIVCC Dog 8.1.1 Effect of rhNRG-1 β on Left Ventricle EF/FS Value of TIVCC Dog EF and FS value prior to the constriction in model animals were 82.3±1.6% and 49.2±2.6% respectively through echocardiography examination and reduced to 59.1±7.3% and 29.3±3.9% respectively after the operation, there was significant difference between that prior to and that after the constriction (P<0.01, P<0.05), EF and FS value continuously maintained at 55.5±10.9% and 28.5±6.6% level 5 days later, demonstrating that through constriction of the inferior vena cava, the congestive heart failure dog model was established and was relatively stable.

EF and FS value of all the three dosage level groups after rhNRG-1 β injection raised significantly, EF and FS of the low dosage level group (1 μg/kg) increased from 57.7±10.9 and 30.6±8.0 to 70.4±8.4 and 39.7±5.7, there was significant difference between prior to and after the drug administration (P<0.05), meanwhile, there was significant difference when comparing with that of the model group (P<0.05). In addition, EF/FS value of the medium and high dosage level group model animals increased significantly as well and there was significant difference when compared that prior to and after the drug administration with that of the model group (P<0.01), Table 35 showed the results.

changes of 3 and 10 μg/kg dosage level group was even significant (P<0.01). Results of heart rate changes determination showed that rhNRG-1 β has less effect on heart rate. (no details were revealed).

TABLE 36

Effect of rhNRG-1 β on cardiac output of TIVCC dog (L/min)

| Group | preoperation | CO (L/min) Prior to drug administration | After drug administration |
|---|---|---|---|
| Pseudo-operation group | 4.3 ± 0.7 | 3.9 ± 0.6 | 4.0 ± 0.6** |
| Model group | 4.7 ± 1.3 | 2.5 ± 0.8 | 2.7 ± 0.5 |
| rhNRG-1 β 10 μg/kg | 4.3 ± 0.6 | 1.9 ± 0.3 | 3.6 ± 0.7**▲▲ |
| rhNRG-1 β 3 μg/kg | 4.3 ± 0.8 | 2.1 ± 0.7 | 4.0 ± 0.9*▲▲ |
| rhNRG-1 β 1 μg/kg | 4.2 ± 0.6 | 2.4 ± 0.5 | 3.7 ± 0.8*▲ |

All of the above described groups, n = 6
*P < 0.05, when comparing with that of the model group;
**P < 0.01, when comparing with that of the model group; ;
▲P < 0.05, when comparing that prior to and that after the drug administration
▲▲P < 0.01, when comparing that prior to with that after the drug administration 8.2 Effect of rhNRG-1 β on Blood Flow Dynamics of TIVCC Dog Changes of left and right ventricular dp/dt and end systolic pressure/end diastolic pressure were determined with floating

TABLE 35

Effect of rhNRG-1 β on EF/FS of the left ventricle in TIVCC dog

| Group | preoperation | FS (%) Prior to drug administration | FS (%) After drug administration | Preoperation | EF (%) Prior to drug administration | EF (%) After drug administration |
|---|---|---|---|---|---|---|
| Pseudo-operation group | 51.7 ± 2.2 | 47.4 ± 1.3** | 50.3 ± 2.2** | 84.1 ± 1.4 | 81.4 ± 1.1** | 83.1 ± 1.6** |
| Model group | 49.2 ± 2.6 | 29.3 ± 3.9 | 28.5 ± 6.6 | 82.3 ± 1.6 | 59.1 ± 7.3 | 55.5 ± 10.9 |
| rhNRG-1 β 10 μg/kg | 50.5 ± 3.3 | 27.7 ± 5.6 | 41.5 ± 3.1**▲▲ | 82.9 ± 2.6 | 55.8 ± 10.0 | 74.7 ± 3.2**▲▲ |
| rhNRG-1 β 3 μg/kg | 51.7 ± 2.9 | 29.9 ± 6.4 | 42.4 ± 4.4**▲▲ | 84.7 ± 2.8 | 58.0 ± 8.3 | 74.7 ± 4.6**▲▲ |
| rhNRG-1 β 1 μg/kg | 50.8 ± 4.0 | 30.6 ± 8.0 | 39.7 ± 5.7*▲ | 82.8 ± 3.0 | 57.7 ± 10.9 | 70.4 ± 8.4*▲ |

All of the above described groups, n = 6
*P < 0.05, when comparing with that of the model group;
**P < 0.01, when comparing with that of the model group;
▲P < 0.05, when comparing that prior to and that after the drug administration
▲▲P < 0.01, when comparing that prior to and that after the drug administration 8.1.2 Effect of rhNRG-1 β on Cardiac Putput (CO) of TIVCC Dog Table 36 showed that rhNRG-1 β could significantly increase cardiac output of the model animals, cardiac output of the 1 μg/kg of rhNRG-1 β group increased from 2.4±0.5 to 3.7±0.8 and there was significant difference when compared that prior to and that after the drug administration (P<0.05), meanwhile, there was significant difference as well when comparing with that of the model animals (P<0.05). CO catheterization technique. The results showed that 1, 3 and 10 μg/kg of rhNRG-1 β could effectively increased the left ventricular dp/dt of animals, there was significant difference when comparing with that of the model group (P<0.05); effectively raised the LVPmax, reduced LVPmin value, when comparing with that of the model group, P<0.05; rhNRG-1 β has less effect on left heart dp/dt, right ventricular +dp/dt and ventricular end pressure, Tables 37 and 38 showed the results in details.

TABLE 37

Effect of rhNRG-1 β on left ventricular dp/dt of TIVCC dog

| Group | L(+dp/dt) (mmHg/s) | L(−dp/dt) (mmHg/s) |
|---|---|---|
| Pseudo-operation group | 5088.99 ± 982.87** | −3233.39 ± 923.82 |
| Model group | 2017.75 ± 295.25 | −2384.94 ± 1062.31 |
| rhNRG-1 β 10 µg/kg | 5104.88 ± 1332.05** | −3658.34 ± 1390.97 |
| rhNRG-1 β 3 µg/kg | 5000.45 ± 1535.88** | −3249.52 ± 973.32 |
| rhNRG-1 β 1 µg/kg | 4024 ± 1006 635.63** | −2933 ± 613.44 |

All the above described groups n = 6
*P < 0.05, when comparing with that of the model group;
**P < 0.01, when comparing with that of the model group;

TABLE 38

Effect of rhNRG-1 β on left ventricular LVPmax/LVPmin of TIVCC dog

| Group | LVPmax (mmHg) | LVPmin (mmHg) |
|---|---|---|
| Pseudo-operation group | 145.04 ± 15.17** | −0.03 ± 6.48 |
| Model group | 95.07 ± 11.62 | 2.42 ± 2.86 |
| rbNRG-1 β 10 µg/kg | 122.87 ± 17.37* | −0.69 ± 1.05* |
| rhNRG-1 β 3 µg/kg | 114.68 ± 17.12* | −1.12 ± 1.34* |
| rhNRG-1 β 1 µg/kg | 102.12 ± 12.42 | 0.59 ± 3.05 |

All the above described groups n = 6
*P < 0.05, when comparing with that of the model group;
**P < 0.01, when comparing with that of the model group;

10 Conclusion

All the three dosage level (1, 3 and 10 µg/kg) of rhNRG-1 β administered for consecutive 5 days could raise the EF/FS value and cardiac output (CO) of the model animal, there was significant difference when comparing that prior to with that after the drug administration (P<0.005, P<0.01); 1, 3 and 10 µg/kg of rhNRG-1 β could effectively increase left ventricular dp/dt and there was significant difference when comparing with that of the model group (P<0.05), being able to effectively raise the LVPmax, reduce LVPmin of the model animals and there was significant difference when comparing with that of the model group, P<0.05, while was less effect on the right ventricle. Results of the experiment showed that rhNRG-1 β could effectively treat the congestive heart failure caused by constriction of inferior vena cava.

Example 7

*Rhesus* Long-term Toxicity Study of Recombinant Human Neuregulin-1 β S177-Q237 for Injection Abstract Long-term toxicity experiment on intravenous injection of 7.5, 15, 75 µg/d of Recombinant Human Neuregulin-1 $β_{S177-Q237}$ for Injection to *rhesus* (the dosage used was based on the effective dosage in mice pharmacodynamic model and conversed to dosage equivalent to 2, 4, 20 times that of the dosage for monkey; and based on dog pharmacodynamic model and conversed to dosage equivalent to 4, 5, 9, and 45 times that of dosage for monkey), excipient was used as control; monitoring was continuously carried out for 3 weeks after drug withdrawal. Toxic reactions of Recombinant Human Neuregulin-1 β S177-Q237 for Injection and their severity to organism was studied, to look for target organs of the toxic reactions and reversibility of the damage and to determine dosage that does not cause toxic reaction and to serve the dosage as a reference for safe dosage to be used in human.

The experiment animals were randomly divided into 4 groups based on their body weight with 6 animals, 3 male and 3 female, in each group. Volume of the drug administered was 1 ml/kg body weight. Body weight was measured weekly and dosage was regulated according to the body weight measured. The drug was administered every day in the morning for consecutive 3 weeks. Electrocardiogram, hematological, biochemistry, urine and fecal testing and determination of antibody were carried out prior to the drug administration and 10 days and 21 days after the beginning of drug administration respectively. Fundus examination was performed under anesthesia at 22 days and 42 days (counted from the first day of drug administration) respectively, then ⅔ and ⅓ animals were killed, autopsied and studied pathohistologically, bone marrow smear was prepared at the same time. Echocardiography was performed under anesthesia one day prior to the autopsy.

No animal death associated with the testing drug happened during the experiment. Vomiting, nausea and salivation occurred in part of the animals in each drug taken group 1 week after the beginning of drug administration; pilo-erection, fur without luster, reduction of activity, anorexia were seen 2 weeks after the drug administration; mild paleness, hardening of regional skin and vessels was discovered at the site of drug injection; the above-mentioned symptoms and sign disappeared or reduced 3 weeks after drug withdrawal. No abnormal manifestations were seen in animals of the control group during period of drug administration and convalescent period after drug withdrawal.

Food ingestion reduced significantly and body weight lowered markedly in the high dosage group (self-comparison prior to and after the drug administration showed that the difference was significant; whereas there was no significant difference when comparing with that of the control group). There were no significant changes of body temperature in all the animals prior to and after the drug administration.

Hematological, biochemistry examination, urine and fecal testing showed no significant toxicological changes.

Electrocardiography: no significant deceleration of heart rate was seen in conscious animals at 10-day of drug administration, while significant reduction of heart rate happened at 3-week of drug administration in conscious animals of every drug taken group, probably due to pharmacological effect of the testing drug; in addition, relatively high voltage of R and S wave in V1 and V3 leads of electrocardiogram, probably associated with variation of chest leads of the animals; no significant abnormality in echocardiogram, heart rate and other index and no hypertrophic changes of the myocardium were seen pathologically.

No abnormal changes in fundus examination were seen.

No significant toxic pathologic changes were seen in the bone marrow smear.

Autopsy performed at 3-week of drug administration showed pericardial effusion in 3 animals each in both medium and high dosage groups and 2-3 ml of transudate could be drawn out in each of them; hydrocephalus in the subarachnoid space was discovered in 2 animals of the high dosage group and 0.5 and 3 ml of transudate was drawn out from each of them respectively.

Various degree of vacuole appeared in the cytoplasma of myocardium, vascular congestion and mild edema under the pia mater were seen in those with hydrocephalus. All of them had something to do with the testing drug.

Antibody testing showed negative results.

The gastrointestinal symptoms such as vomiting, nausea and anorexia of those animals and the resulting reduction of body weight in the high dosage group due probably to distribution and elimination of the testing drug in the gastrointestinal tract. Symptoms such as paleness, hardening of skin at the injection site, pericardial effusion and hydrocephalus, and without entirely recovery of hydrocephalus of high dosage group animals 3 weeks after drug withdrawal demonstrated that capillary exudate and transudate syndrome in rheusus can be caused by medium and high dosage of Recombinant Human Neuregulin-1 $\beta_{S177\text{-}Q237}$ for Injection. In addition, deceleration of heart rate in conscious animals and vacuole in the cytoplasma of myocardium of high dosage group animals were all associated with the testing drug.

Conclusion: Daily intravenous injection of 7.5, 15, 75 µg/d of Recombinant Human Neuregulin-1 $\beta_{S177\text{-}Q237}$ for Injection to *rhesus* for a total of 3 weeks and continuously monitoring for 3 weeks were carried out. The results showed that more than 10 days of consecutive injection of Recombinant Human Neuregulin-1 $\beta_{S177\text{-}Q237}$ for Injection could cause deceleration of heart rate in conscious animals; it may lead to gastrointestinal reaction; caused pericardial effusion, hydrocephalus and mild congestion and edema under the pia mater in *rhesus* of medium and high dosage group, the hydrocephalus did not recover entirely 3 weeks after drug withdrawal in the high dosage group animals; paleness and hardening of skin and vessels in the injection site recovered gradually after drug withdrawal. Those manifestations demonstrated that the possible cause was capillary transudate-exudation syndrome. High dosage of Recombinant Human Neuregulin-1 $\beta_{S177\text{-}Q237}$ for Injection could cause vacuole in the cytoplasma of myocardium; antibody testing showed negative results. The dosage level that did not cause pericardial effusion and hydrocephalus during 3-week's drug administration and 3-week's convalescent period was 7.5 µg/kg/d.

1. Objectives of the Experiment

To study the toxic reactions of Recombinant Human Neuregulin-1βS177-Q237 for Injection and their severity to organism, to look for target organs of the toxic reaction and reversibility of the damage, to determine dosage that does not cause toxic reactions and to serve the dosage as a reference for safe dosage to be used in human.

2. Testing Drug:
2.1 Name of the drug: Recombinant Human Neuregulin-1 $\beta_{S177\text{-}Q237}$ for Injection.
2.2 Batch number: 200210024.
2.3 Institute that provided the drug: Zensun (Shanghai) Science & Technology Development Company Ltd, Address: 2$^{nd}$ floor of C building, 328 Bi Bo Road, Zhang Jiang High Tech Zoon.
2.4 Content: 3.75 mg/ml.
2.5 Specific activity: $1.12 \times 10^4$ U/mg.
2.6 Character: transparent colorless solution.
2.7 Storage: Store at 4° C.
2.8 Excipient: 0.15M NaCl, 10 nM sodium phosphate, pH 6.0.
2.9 Preparing: Dilute with normal saline to the needed concentration.

3. Animals:
3.1 Species of the animals: *Rhesus*.
3.2 Source of animals: Da Li Ji *Rhesus* Breeding Farm, Li Xing County, Anhui Province, certificate of competency: Wan Fa Xun Fan No.2002-6.
3.3 Reception Date of the animals: 13 Oct. 2002.
3.4 Body weight: 2.6-5.9 kg at the beginning of drug administration.
3.5 Gender: Half male and half female.
3.6 Number of animals: a total of 24 animals.
3.7 Marks on the animals: Chest card was used to identify individual animal.
3.8 Feeding condition: One animal for each cage, fed with granule feedstuff (provided by Shanghai Shi Ling Science & Technology Company Ltd). The animals were fed with 100 gram feedstuff two times daily in addition to about 100 gram of fruit. The room temperature was kept at 20-25° C., relative humidity of 50%-70%, illumination for 12 hours every day.
3.9 Environmental adaptation time: Breeding for 25 days for environmental adaptation.

4. Dosage:
4.1 Dosage set up:
Control group: 0 µg/kg/d (injected with equal volume of excipient);
Low dosage group: 7.5 µg/kg/d (comparable to 2 times that of monkey equivalent dosage);
Medium dosage group: 15 µg/kg/d (comparable to 4 times that of monkey equivalent dosage);
High dosage group: 75 µg/kg/d ((comparable to 20 times that of monkey equivalent dosage).
4.2 Rationale of the dosage set up:
The scheduled indication for Recombinant Human Neuregulin-1 $\beta_{S177\text{-}Q237}$ for Injection was for therapy of heart failure. The mice pharmacodynamic model was pro-cardiac Coxsacki B3 virus induced myocarditis model, dosage used were 7.5, 15 and 30 µg/kg/d (equivalent to 1.875, 3.75 and 7.5 µg/kg/d used for monkey), injected intravenously for consecutive 5 days, the pathologic score was 1.5, 0.7 and 0.56 respectively (the criteria for pathologic scoring is: score 0: area of lesions=0%, score 1: area of lesions=25%, score 2: area of lesions=50%, score 3: area of lesions=100%). Therefore, dosage of 15 and 30 µg/kg/d could significantly reduce damage to the heart. The scheduled route of drug administration was intravenous injection, once every day for consecutive 3-5 days. The MTD of acute toxicity experiment on intravenous injection of Recombinant Human Neuregulin-1 $\beta_{S177\text{-}Q237}$ for Injection was 35 mg/kg. Take equivalent dosage for monkey of 3.75 µg/kg/d as significantly effective dosage, the long-term toxic dosage for animals will be tentatively set at 2, 4, and 20 times that of the animals effective dosage.

5. Course of Drug Administration:
Once every day for consecutive 3 weeks.

6. Convalescence Period:
3 weeks.

7. Administrated Drug Volume:
1.0 ml/kg body weight.

8. Route of Drug Administration:
Slow intravenous injection, the same as that used clinically.

9. Method of the Experiment:
Albendazole was used to kill intestinal parasites and tuberculin test was performed prior to buy in the experiment animal, then environmental adaptation; hematological, biochemistry, urine testing and electrocardiography were performed two times to ensure that the experiment animals were in healthy condition. 4 groups were divided based on body weight and gender of the animals, with 6 animals in each group, half male and half female. The volume of drug administered was 1.0 ml/kg body weight, body weight was measured weekly prior to each drug administration and the volume of drug to be administered will be adjusted according to the body weight measured, ⅔ and ⅓ of the animals (2 female and 1 male monkeys each) in each group were killed at 24 hours after 3-week of drug administration and at the end of 3-week after the convalescence period, autopsy performed, organs weighed, organ coefficient calculated and pathohistological examination carried out. Blood was withdrawn for hematological and biochemistry examination and bone marrow smear was performed at 10-day of drug administration and prior to autopsy.

9.1 Reagent:
    9.1.1 Reagent for hematological testing.
    9.1.2 Reagent for serum biochemistry testing: Trace imported biochemistry reagent.
    9.1.3 Main reagent for antibody detection.
        ① Coating liquid: $NaHCO_3$ 0.293 g, $Na_2CO_3$ 0.159 g, dissolve in 100 ml water.
        ② Substrate buffer solution: pH 5.0, citric acid 1.02 g, $Na_2HPO_4.12H_2O$ 3.68g dissolve in water.
        ③ Cleaning solution: 0.01M PBS adds 1:2000 Tween-20
        ④ Sealing solution: evaporated skimmed milk 5 g, dissolve in 100 ml, pH 7.4 0.01M PBS.
        ⑤ HRP labeled rat anti-monkey second antibody: Product of Sigma Company of the U.S. batch number: A-2054.
        ⑥ Tween-20: Separated package of imported raw material, provided by Zensun (Shanghai) Science & Technology Company Ltd.
        ⑦ Tetramethylo-aminobenzene (TMB: Separated package of imported raw material, provided by Shanghai Huamei Bioengineering Company.
        ⑧ $H_2SO_4$: analytical reagent, Shanghai Ling Feng Chemical Reagent Co Ltd.

9.2 Equipment:
    Roche Hematology Vet Blood Cell Counter.
    Hitachi-7060 Automatic Biochemistry Analytic Machine.
    550 Enzyme labeling machine: product of BIO-RAD of the U.S.
    Heraeus Low temperature centrifuge, Heraeus Company of Germany.
    Hewlett Packard sonos 5500 echocardiography machine, with S4 probe.

9.3 Hematological and serum biochemistry testing methods: refer to the following table Method of Hematological Testing

| Topic of testing | Method of testing |
| --- | --- |
| WBC white blood cell | Instrumental Analysis |
| RBC red blood cell | Instrumental Analysis |
| PLT platelet | Instrumental Analysis |
| Ht hematocrit | Instrumental Analysis |
| Hb hemoglobin | Instrumental Analysis |
| MCV mean corpusclular volume | Instrumental Analysis |
| MCH mean corpusclular hemoglobin | Instrumental Analysis |
| MCHC mean corpusclular hemoglobin concentration | Instrumental Analysis |
| Ret reticulocyte count | BrilliantCresyl blue method |
| DC differentiation count | Wright stain |
| CT clotting time | Slide method |

Serum Biochemistry Testing Method

| Testing | Method |
| --- | --- |
| ALT/GPT alanine aminotransferase | IFCC w/o P-5-P |
| AST/GOT aspartate aminotransferase | IFCC w/o P-5-P |
| ALP alkaline phosphatase | Tris/Carb |
| LDH lactic acid dehydrogenase | LP→enzyme method |
| CPK creatine phosphokinase | NAC enzyme method |
| BUN blood urea nitrogen | Urease-GLDH-Kinetic |
| CRE creatinine | Jaffe-Kinetic |
| GLU glucose | Oxidase |
| T-Bil total bilirubin | Dimethyl sulfoxide method |
| T-CHO total cholesterol | Enzymatic |
| TP total protein | Biuret |
| ALB albumin | Bromcresol green method |
| $K^+$ kalium | Electrode method |
| $Na^+$ natrium | Electrode method |
| $Cl^-$ chloride | Electrode method |
| $P^{+++}$/PHOS inorganic phosphorus | Phosphomolybdate-UV |
| $Ca^{++}$ calcium | Orthocresol phthalein complexon method |
| $Mg^{++}$ magnesium | Calmagite complexometric indicator |

9.4 Method of antibody detection

Coating antigen: Recombinant Human Neuregulin-1 $β_{S177-237}$ for Injection was diluted to 6 μg/ml with coating buffer solution, add into 96 hole enzyme labeled plate with 100 μl/hole, 37° C. for 1 hour.

Sealing: Wash the plate 5 times, prepare 5% evaporated skimmed milk with cleaning solution.

Dilute the scheduled for testing serum; dilute the sample with sample dilution solution, dilute gradient is 1:100.

Add sample: Wash the sealed enzyme labeled plate for 3 times, add scheduled for testing serum, 100 μl/hole, 37° C. for 1 hour.

Add enzyme labeled antibody: Wash the plate 5 times, add 1:1000 diluted HRP labeled rat anti- monkey immunoglobulin, 100 μl/hole, 37° C. for 1 hour.

Substrate Wash the plate 5 times, add newly prepared substrate operating fluid, 100 μl/hole, 37° C. for 10 minutes.

Ending: add 2N $H_2SO_4$, 50 μl/hole to end the reaction.

Odd value detection: Positive result was defined as OD value of testing sample was 2.1 time greater than that of the negative control (serum was 1:100 diluted).

10. Observation and Research Period 10.1 Death status:
    Monitoring was carried out once or twice daily and the time of animal death will be recorded if there is any animal death.

10.2 General symptoms:
    Including general appearance, sign, behavior activity, blood or exudation attached on the cage surface, luster of the fur. The observation was carried out once or twice daily.

10.3 Body weight:
    Body weight was measured once daily prior to drug administration.

10.4 Body temperature:
    Body temperature was taken prior to and 1 hour after the drug administration at 1, 3 and 5-day of drug administration.

10.5 Feedstuff ingestion:
    Granule feedstuff 200 g was given to each monkey daily, with 100 g of fruits, calculate the consumption of food per animal per day.

10.6 Electrocardiograph:
  2 electrocardiograph examinations was performed prior to the drug administration and also at 10 days after the beginning of drug administration, at the end of drug administration and during the convalescence period respectively, P-R, QRS, QT and ST value were calculated.
10.7 Echocardiograph:
  After ending the drug administration and 1 day prior to autopsy at the end of convalescence period, the animals scheduled to be autopsied will be anesthetized with intravenous injection of 3% pentobarbital (30 mg/kg), then echocardiography performed to determine the intraventricular thickness (IVS), postereior wall of left ventricule (PW), left ventriclular end diastolic volume (LVDd), left ventricular end systolic volume (LVDs), ejection fraction (EF), shortening fraction (Fs), mitral valve blood flow peak value (MV), aortic valve blood flow peak value (AV) and heart rate (HR).
10.8 Hematological index:
  Two times prior to the drug administration, 10-day after the beginning of the drug administration, at the end of drug administration and at the end of 3-week's convalescence period prior to autopsy, 0.5 ml blood was drawn from the saphenous veins, treated with 3.8% EDTA for anticoagulation, testing for the following index: red blood cell count (RBC), reticulocyte count (Ret), hemoglobin (Hb), white blood bell count (WBC) and differentiation count including: neutrophil(N), eosinophil (E), Lymphocyte (L) and monocyte (M), platelet count (PLT), clotting time (CT), hematocrit (Ht), mean corpuscular volume (MCV), mean concentration hemoglobin (MCH) and mean corpuscular hemoglobin concentration (MCHC).
10.9 Serum biochemistry index:
  Two times prior to the drug administration, 10-day after the beginning of drug administration, at the end of drug administration and 3-week after convalescence period prior to autopsy, 5 ml blood was drawn from the saphenous veins, serum was separated after centrifugation and the following items were tested: aspartate aminotransferase (AST), alanine aminotransferase(ALT), alkaline phosphatase(ALP), lactic acid dehydrogenase (LDH), creatine phosphokinase(CPK), blood urea nitrogen (BUN), total protein(TP), albumin,(ALB) glucose (GLU), serum total bilirubin (T-Bil), creatinine (CRE), total cholesteral (T-CHO), natrium ($Na^+$), kalium (K+), chloride ($Cl^-$), calcium ($Ca^{++}$), magnesium ($Mg+^+$) and phosphorus ($P^{+++}$).
10.10 Urine testing
  Two times prior to drug administration, 10-day after the beginning of drug administration, at the end of drug administration, 3-week after convalescence period prior to autopsy, urine sample was collected for testing white blood cell, nitrite, pH value, urine protein, glucose, ketone body, urobilinogen, urine bilirubin and hemoglobin.
10.11 Fecal testing
  Fecal parasitic ovum and occult blood were tested prior to drug administration. Fecal occult blood test was also performed at 10-day after the beginning of drug administration, at the end of drug administration and 3-week after convalescence period.
10.12 Fundus examination:
  Fundus examination was carried out under anesthesia prior to autopsy.
10.13 Systemic Autopsy:
  ⅔ and ⅓ animals in each group (with 2 female and 1 male animal each) were killed 24 hours after 3-week of drug administration and at the end of convalescence period after the end of drug administration, and autopsy carried.
10.14 Organ coefficient:
  Heart, brain, liver, spleen, lungs, kidneys, adrenals, thymus, lymphnodes, thyroid, testis or uterus, ovary or prostate were taken out, their weight measured and the coefficient calculated.
10.15 Pathohistological examination:
  Pathohistological examination of the following organs were carried out: heart (anterior wall of left ventricle, right ventricle, interseptum, left atrium, right atrium), liver, spleen, lungs, brain, stomach, duodenum, ileum, colon, kidneys, urinary bladder, adrenals, pituitary, thyroid, thymus, pancreas, testis, prostate, ovary, uterus, lymph nodes (cervical, mesentery), vessels and subcutaneous tissue of the injected site.
10.16 Bone marrow examination:
  Bone marrow sample from the femoral bone was taken out prior to autopsy under anesthesia, smear, staining and optic microscopic examination carried out to study the magakaryocyte system, granulocyte and erythrocyte system, lymphocyte, plasmocyte and other type of cells. 5×100 nucleated cells in the four quadrants and central part will be counted, GE ratio calculated and photographs taken.
10.17 Serum Recombinant Human Neuregulin-1 $\beta_{S177-Q237}$ for Injection antibody detection:
  1, 2 and 3-week after the beginning of drug administration, and at the end of convalescence period serum Recombinant Human Neuregulin-1 $\beta_{S177-Q237}$ for Injection antibody was detected, and drug administration will be stopped whenever antibody was detected and the detected antibody being neutralizing antibody.
10.18 Data processing and statistic analysis:
  Variance analysis was carried as statistical testing for data collected from various dosage groups and control group.
11. Results of the Experiment:
11.1 Death status:
  No animal death associated with the testing drug happened during the experiment period.
  At the end of 3-week of drug administration, significant deceleration of heart rate (20-30 beat/min) of 1 animal each (5# and 6#) in the control group and low-dosage group were seen through echocardiography examination under anesthesia at the end of 3-week's convalescence period; being manifestation of over-anesthetization, thus, autopsy was carried out one day before scheduled. (Table 1).
11.2 General manifestation:
  Vomiting happened in 1 male monkey in high-dosage group 30 minutes after intravenous injection at 2-day of drug administration. During the 2-7 days of drug administration, 1 animal each in the medium and high-dosage group vomited in 20-30 minutes after intravenous injection. Salivation happened in part of the animals in every group after 1-week of drug administration, the rate of occurrence was significantly higher in high-dosage group than that in other drug taken groups; only 1 animal in low-dosage group showed salivation at 9-day of drug administration. Pilo-errection, lost of luster of fur, reduced activity, anorexia appeared in high-dosage group at 2-week of drug administration. Mild paleness, hardening of regional skin and vessels in the injection site began from the $3^{rd}$ day of drug administration, exaggerated progressively and was dosage dependent. The aforementioned symptoms and signs disappeared or improved at 3-week of convalescence period after drug withdrawal. Light yellow color stool diarrhea and without regularity happened in animal 21# of high-dosage group. No abnormal manifestation appeared in animals of the control group during period of drug administration and convalescence period after drug withdrawal.

11.3 Changes of body weight:

No significant difference in body weight ($P>0.05$, Table 2; FIG. 1) was seen between animals of the control group and various drug taken groups; self-comparison in animals prior to and after drug administration showed significant reduction of body weight in animals of high-dosage group ($P<0.01$).

11.4 Body temperature:

No significant difference in body temperature taken prior to drug administration and 1 hour after drug administration at 1, 3 and 5-day of drug administration was seen (Table 3).

11.5 Feedstuff ingestion:

Significant remnant of feedstuff and various amount of ingestion from 50 to 150 g of feedstuff was seen in animals of medium and high-dosage groups after 1-week of drug administration. No remnant of feedstuff was seen in animals of the control group and low-dosage group and no remnant of feedstuff happened in all animals during convalescent period.

11.6 Results of electrocardiograph examination:

No significant deceleration of heart rate was seen in all the conscious animals of every drug- taken group at 10-day of drug administration ($P>0.05$ when comparing with that of the control group), and significant deceleration of heart rate happened in conscious animals of every drug taken group, and $P<0.05$, $P<0.01$, when comparing with that of the control group; at the same time, P-R, QRS and QT interval were prolonged accordingly, being more marked in the low and medium dosage groups, they returned to normal 3-week after drug withdrawal; Voltage of Rv1 in animals of medium and high-dosage group was higher, while Sv1 in high, low and medium dosage group were deeper and voltage of Rv3 in every drug taken groups were higher. ($P<0.05$; $P<0.01$ and $P<0.001$, Table 4-7). There was mild fluctuation in other individual parameter collected in different time, however, all were within normal range.

11.7 Results of echocardiograph:

No significant difference in parameters of echocardiogram in control group and various drug taken group at 3-week of drug administration and at the end of 3-week of convalescent period were seen ($P<0.05$, Table 8-9).

11.8 Results of hematological examination:

No significant abnormal changes in addition to fluctuation within normal range of individual parameters during the entire experiment period were seen (Table 10-13).

11.9 Results of serum biochemistry testing:

No significant abnormal changes in addition to fluctuation within normal range of individual parameters during the entire experiment period were seen (Table 14-17).

11.10 Results of urine testing:

Increase of urine protein, positive ketone body, but without regularity, in urine testing of individual animals in every drug taken group and control group were seen prior to drug administration, at 10-day and 3-week after the beginning of drug administration, and at 3-week of convalescence period prior to autopsy. Transient increase of red blood cells in urine was seen in individual animals of control group and every drug taken group. No other significant abnormality was seen (Table 18-21).

11.11 Results of fecal testing:

Negative Fecal occult blood test and no fecal parasitic ovum were seen in all the animals prior to drug administration, at 10-day and 3-week after the beginning of drug administration, and at 3-week of convalescence period prior to autopsy (Table 22).

11.12 Results of fundus examination:

No abnormality was seen in fundus examination performed at 3-week of drug administration and at 3-week of convalescence period prior to autopsy (Table 23).

11.13 Systemic anatomy:

Small amount of effusion in the pericardial cavity of 2# male monkey and 23#, 24# female monkey in medium dosage group were discovered and 2-3 ml of clear slight yellow color fluid was drawn out in each animal at 3-week of drug administration; hydrorcephalus in the subarachnoid space was seen in 1# and 21# animal of the high-dosage group, and 1-2 ml of clear slight yellow color fluid was drawn out from each animal; there is effusion in peritoneal cavity, bleeding spot on the surface of colonic mucosa of 21# animal together with focus of ulcer in 21# animal. Congestion and hemorrhagic lesion in pulmonary lobe was seen in 22# male monkey of high-dosage group. 8# monkey of the control group dies prior to autopsy due to over-anesthetization, significant congestion and patchy bleeding in the lungs were seen during autopsy, no other significant abnormality was seen.

At the end of 3-week's convalescence period, hydrocephalus in the subarachnoid space was seen in one male and one female animals (10#, 14#) of high-dosage group, 0.5 ml and 3 ml fluid were drawn out from them respectively; there were no significant abnormality seen in animal that was over-anesthetized and autopsied in advance.

No abnormality was seen in other organs.

Results of testing for the afore-mentioned effusion demonstrated that they were all transudate.

11.14 Weight of the organs and their coefficient

Weight of major organs were measured and organ coefficient calculated during the autopsy of all animals. No abnormal changes in organ weight, which has something to do with the testing drug, were seen (Table 24-25).

11.15 Results of pathohistological examination:

Light stained vacuole appeared in cytoplasma of myocardium of the atrium and ventrircle of 1#, 11# male monkey and 21# female monkey of high-dosage group, with their severity of "+" or "+ to ++", striated structure was maintained; there was diffusive vacuole-like degeneration, without significant abnormality in endocardium and pericardium. On the other hand, vascular congestion and mild edema were seen in the subarchnoid space of 11# and 21# monkey; there were inflammatory cells infiltration in part of the colonic mucosa of 21# animal; thickening of avleola septum, congestion, patchy hemorrhage of the lung, full with edematous fluid in part of the alveola, partly tissue autocytolysis in kidneys, stomach, colon, intestine and pancreas were seen during autopsy of 8# animals that died before the autopsy. No other abnormality was seen.

Micro-vacuole in the myocardial cytoplasma, vascular congestion in the subarachnoid space was seen in 14# female monkey of the high-dosage group. No significant abnormality was discovered in animals autopsied in advance due to over-anesthetization. No significant reaction to stimulus in addition to hemorrhagic changes in vessels within the injection site in all the drug administration groups were seen. Sporadic, accidental lesions, such as inflammatory reaction in the lungs and gastrointestinal tract were seen in the remaining animals, most of them were spontaneous lesions (Table 26, 27 and Photos 1-22).

11.16 Results of Bone Marrow Examination:

Bone marrow was aspirated from the right hip bone prior to autopsy under anesthesia at 3-week of drug administration and 3rd week of convalescence period, smear made, stained and megakaryocyte systemi, granulocyte system, erythrocyte system, lymphocyte and plasmocyte and other type of cells were examination under optic microscope. 5×100 nucleated cells in the four quadrants and central part were counted and differentiation counting performed, GE ratio calculated and microphotography carried out.

Results: Normal proliferation in all the granulocyte, erythrocyte and megakaryocyte system were seen, with normal ratio of granulocyte to erythrocyte system; no abnormal pathologic cells and no bone marrow toxic pathologic damage was caused. (Table 28-29; photos 23-34).

11.17 Results of serum Recombinant Human Neuregulin-1 $\beta_{S177\text{-}Q237}$ for Injection antibody detection:

All the serum Recombinant Human Neuregulin-1 $\beta_{S177\text{-}Q237}$ for Injection antibody detection in all drug taken group at 1, 2, 3-week after the beginning of drug administration and at the end of 3-week of convalescent period showed negative results. (Table 30).

12. Discussion:

Intravenous injection of 7.5, 15, 75 μg/d of Recombinant Human Neuregulin-1 $\beta_{S177\text{-}Q237}$ for Injection to *rhesus* (the dosage used was equivalent to 2, 4, 20 times that of the dosage for monkey); excipient was used as control; monitoring was carried out for 3 weeks after drug withdrawal.

No animal death associated with the testing drug happened during the experiment.

Vomiting, nausea and salivation occurred in part of the animals in each drug-testing group 1 week after the beginning of drug administration; pilo-erection, fur without luster, reduction of activity, anorexia were seen in animals of the high-dosage group 2-week after the drug administration; mild paleness, hardening of regional skin and vessels at the site of drug injection; the afore-mentioned symptoms and signs disappeared or reduced 3 weeks after drug withdrawal. No abnormal manifestations were seen in animals of the control group during period of drug administration and convalescent period after drug withdrawal.

Food ingestion reduced significantly and body weight lowered markedly in the high dosage group in self-comparison prior to and after the drug administration. There were no significant changes of body temperature in all the animals prior to and after the drug administration.

Hematological, biochemistry examination, urine and fecal testing showed no significant toxicological changes.

Electrocardiography: no significant deceleration of heart rate was seen in conscious animals at 10 days of drug administration, while significant reduction of heart rate happened at 3-week of drug administration in conscious animals of every drug taken group, probably due to pharmacological effect of the testing drug; in addition, relatively high voltage of R and S wave in V1 and V3 leads of electrocardiogram, probably associated with variation of chest lead of the animals were seen; no significant abnormality in echocardiogram, heart rate and other indexwere discovered; no hypertrophic changes of myocardium was seen pathologically.

No abnormal changes in fundus examination were seen.

No significant toxic pathologic changes were seen in bone marrow smear.

Autopsy performed at 3-week of drug administration showed pericardial effusion in 3 animals, each in both medium and high dosage groups and 2-3 ml of transudate could be drawn out; hydrocephalus in the subarachnoid space was discovered in 2 animals of the high dosage group and 1-3 ml of transudate was drawn out.

Various degree of vacuole appeared in the cytoplasma of myocardium, vascular congestion and mild edema under the pia mater were seen in those with hydrocephalus. All of them had something to do with the testing drug.

Antibody testing showed negative results.

The gastrointestinal symptoms such as vomiting, nausea and anorexia of those animals could lead further to reduction of body weight in the high dosage group due probably to distribution and elimination of the testing drug in the gastrointestinal tract. Symptoms such as paleness, hardening of skin at the injection site, pericardial effusion and hydrocephalus were seen, and without entire recovery of hydrocephalus in high dosage group animals 3 weeks after drug withdrawal, demonstrating that capillary exudate and transudate syndrome in *rhesus* can happened in medium and high dosage of Recombinant Human Neuregulin-1 $\beta_{S177\text{-}Q237}$ for Injection groups. In addition, deceleration of heart rate in conscious animals and vacuole in the cytoplasma of myocardium of high dosage group animals were all associated with the testing drug.

Conclusion: Daily intravenous injection of 7.5, 15, 75 μg/d of Recombinant Human Neuregulin-1 $\beta_{S177\text{-}Q237}$ for Injection to *rhesus* for a total of 3 weeks and continuously monitoring for 3 weeks were carried out. The results showed that more than 10 days of consecutive injection of Recombinant Human Neuregulin-1 $\beta_{S177\text{-}Q237}$ for Injection could cause deceleration of heart rate in conscious animals; it may lead to gastrointestinal reaction, caused pericardial effusion, hydrocephalus and mild congestion and edema under the pia mater in *rhesus* in medium and high dosage group animals, the hydrocephalus did not recover entirely 3 weeks after drug withdrawal in the high dosage group animals; paleness and hardening of skin and vessels in the injection site and recovered gradually after the drug withdrawal. Those manifestations demonstrated that the possible cause was capillary transudate-exudation syndrome. High dosage of Recombinant Human Neuregulin-1 $\beta_{S177\text{-}Q237}$ for Injection could cause vacuole in the cytoplasma of myocardium; all the antibody testing showed negative results. The dosage level that did not cause pericardial effusion and hydrocephalus during the 3-week's drug administration and 3-week's convalescent period was 7.5 μg/kg/d.

Example 8

In vitro Determination of NGR-1 Activity (ELISA Test for Kinase Receptor Activation)

1. Principle of the Experiment

HER2/neu gene encods a trans-membrane protein p185, which is a tyrosine protein kinase. Binding of Neuregulin-1 with ErbB3 or ErbB4 induces heterodimer ErbB3-ErbB2 and ErbB4-ErbB2 formation and activates HER2 encoded tyrosine protein kinase, mediating the transmission of functioning signal of Neuregulin-1. Based on the fact that binding of Neuregulin-1 with its receptors triggers phosphorylation of ErbB2 protein, we establish a rapid, sensitive and high flux method for in vitro quantitatively determining biological activity of Recombinant Neuregulin-1.

2. Experiment Material 2.1 96 holes cell cultural plate (Corning company); Costar 96 holes ELISA detecting plate.

2.2 Human breast cancer cell strain, introduced from the U.S. ATCC, was cultivated in base cultural medium under 37° C. and 50% $CO_2$.

2.3 Weighing a given amount of DMEM, quantifying to corresponding volume, added 3.7 g/L of NaHCO$_2$, 0.1 g/L glutamine and 5.5 g/L of HEPES.

2.4 Base culture medium

DMEM culture medium with 10% fetal calf serum and insulin 9 mg/L, stored at 4° C.

2.5 Sterilized PBS (0.01M, pH 7.4).

2.6 0.5% Pancreatic enzyme

Preparing with Ca$^{2+}$ and Mg$^{2+}$ free PBS.

2.7 Anti-ErbB2 monoclonal antibody coating buffer solution, lotion.

Select mouse anti-human ErbB2 extra-cell functioning domain H4 monoclonal antibody with no cross reaction with ErbB3 and ErbB4.

Coating buffer solution; pH 9.6, 0.05M carbonate buffer solution.

Lotion:0.01M PBS+0.05% Tween-20.

2.8 Horse-radish peroxidase (HRP) labeled mouse anti-human phosphorylated protease monoclonal antibody (anti-P-tyr-HRP)

2.9 Substrate, substrate buffer solution

Substrate (TMB): 2 mg/ml TMB (prepare with absolute alcohol).

Substrate buffer: 0.2M citric acid+0.1M Na$_2$HPO$_4$ (pH 5.0).

Operating substrate: substrate buffer solution 9 ml+TMB 1 ml+3% H$_2$O$_2$ 10 ul (prepared as needed).

2.10 Termination agent

2N H$_2$SO$_4$.

2.11 Cell defragmentation solution 150 mM NaCl+50 mM Hepes+1% Triton-X 100+2 mM (sodium orthovanadate)+0.01% (thimerosol). One tablet of mixed protease inhibitor (Tabletten, Proteasen-Irhibitoren-Cocktail) is added into every 25 ml prior to the operation.

2.12 Standard material and sample expected for testing.

3 Experiment Procedure

Process 3.1 was carried out on the first day, that of 3.2~3.3 on the second day, that of 3.4~3.12 was performed on the third day; in which, process of 3.1 and 3.2 should be carried out under sterilization condition.

3.1 Inoculation of cells

MCF-7 cells were amplified to a given amount, washed with sterilized PBS solution, then digested with 0.25% trypsinase. After counting, the concentration of cells was regulated with base culture medium. The cells were added into 96 holes cell culture plate, 5×10$^4$/hole, 100 µl/hole, and cultured over night in the culture box under 37° C. and 5% CO$_2$.

3.2 Cell starvation

Suck up all the culture medium in the 96 holes plate, wash each hole with 37° C. warmed PBS, then add 100 µl DMEM culture medium (calf serum free and without insulin). Cells were cultured for 24 hours in the culture box under 37° C. and 5% CO$_2$.

3.3 Coating

Dilute the anit-ErbB2 extra-cell functioning domain H4 antibody with coating buffer solution to be 6 µg/ml, then add 50 µl per hole to the 96 holes ELISA plate, set over night (16-18 hours) under 4° C.

3.4 Dilute control solution and sample solution expected to be tested

Dilute control solution and sample expected to be tested with DMEM culture medium respectively (calf serum free and without insulin) to be 2 µg/ml, then again carry out 3 times gradient dilution with a total of 9 dilution.

3.5 Phosphorylation of the cells

Suck up the post-starvation 96 holes cell culture medium, add standard material and sample expected to be tested, 100 µl per hole, set up 2 double hole for each concentration. Set up negative control at the same time (i.e. DMEM culture medium placebo control). Reaction for 20 minutes under 37° C.

3.6 Decomposition of the cells

Rapidly suck out the sample and wash once with PBS, 100 µl of fragmentation solution was added into each hole, fragmenting for 30 minutes in 4° C. refrigerator. Horizontally agitate under ice-bath condition till all the anchorage-dependent cell drop down, 4° C., 15,000 rpm centrifuge for 15 minutes.

3.7 Sealing the ELISA detecting plate

Wash the plate 5 times. Prepare 5% skimmed milk with wash solution, add 200 µl to each hole of the plate, set under 37° C. for 2 hours.

3.8 Add sample

After wash 3 times the sealed ELISA plate, add standard cell fragmentation solution and testing sample fragmentation solution with 90 µl per hole, set up negative control at the same time, set for 1 hour under 37° C.

3.9 Add enzyme labeled antibody

Wash the plate 5 times, dilute HRP enzyme linked mouse anti-phosphorylated tyrosine protein antibody with 1:500 lotion (determined by the product using guide and the using time), add 100 µl into each hole of the plate. Set for 1 hour under 37° C.

3.10 Color development of the substrate

Wash the plate 5 times, prepared substrate working solution was added into with 100 µl per hole, set for 10 minutes under 37° C.

3.11 Termination

2N H$_2$SO$_4$ was added into with 50 µl per hole to terminate the reaction.

3.12 OD value reading

Colorimetric analysis on the ELISA reader, determine wave length of 450 nm, reference wave length of 655, record the results.

4 Calculation

Construction with concentration of Recombinant Human Neuregulin-1 versus OD value and analysis was carried out with linear regression method, calculate the half effective dosage of each sample expected for testing.

5 Needed Reagent Formula

| 1. DMEM base culture medium | |
|---|---|
| Fetal calf serum | 100 ml |
| Insulin | 9.2 mg |
| add into 1 L of DMEM culture medium, mixed well. | |
| 2. Cell fragmentation solution | |
| NaCl | 4.38 g |
| HEPES | 5.96 g |
| sodium orthovanadate | 0.368 g |
| thimerosol | 0.05 g |
| Triton-X 100 | 5 mL |
| Dissolve into 500 mL H$_2$O | |
| 3. Coating solution (pH 9.6) | |
| NaHCO$_3$ | 0.293 g |
| Na$_2$CO$_3$ | 0.159 g |
| Dissolve into 100 mL H$_2$O | |

| 4. 100 mL substrate buffer solution (pH 5.0) | |
|---|---|
| Citric acid | 1.02 g |
| Na$_2$HPO$_4$.12H$_2$O | 3.68 g |
| Dissolve into H$_2$O | |

| 5. Sealing solution (5% skimmed milk) | |
|---|---|
| Skimmed milk powder | 5 g |
| Dissolve into 100 mL pH 7.4 0.01M PBS | |

| 6. 0.01M PBS (pH 7.4) | |
|---|---|
| Na$_2$HPO$_4$.12H$_2$O | 2.9014 g |
| NaH$_2$PO$_4$.4H$_2$O | 0.2964 g |
| NaCl | 8.5 g |
| Dissolve into 1000 mL H$_2$O | |

| 7. 0.01M PBS-T (PH 7.4) | |
|---|---|
| Add 1 ml Tween 20 into 2000 ML 0.01 M PBS, mixed well. | |

| 8. 2 mg/ml TMB | |
|---|---|
| TMB | 20 mg |
| Dissolve into 10 mL absolute alcohol | |

| 9. 20 × PBS (1000 ML) | |
|---|---|
| Na$_2$HPO$_4$.12 H2O | 58 g |
| NaH$_2$PO$_4$.4 H2O | 5.9 g |
| NaCl | 170 g |
| Dissolve into 1000 mL H$_2$O. | |

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A method for treating viral myocarditis or dilated (congestive) cardiomyopathy (DCM), in a mammal in need thereof, which method comprises administering to the mammal a neuregulin 1 protein in an amount from about 10 U/kg to about 400 U/kg of body weight of the mammal once a day for a period of between 3 days and 21 days.

2. The method of claim 1, wherein the neuregulin 1 protein carries out its activity via binding with ErbB2-ErbB4 receptors.

3. The method of claim 1, wherein the neuregulin 1 protein is neuregulin α2 or neuregulin β2.

4. The method of claim 1, wherein the neuregulin 1 protein comprises the amino acid sequence of SEQ ID NO: 4.

5. The method of claim 1, wherein the mammal is a human.

6. The method of claim 1, wherein the viral myocarditis is caused by or associated with infection of a virus selected from the group consisting of Coxsackie Group A virus, Coxsackie Group B virus, ECHO virus and polio virus.

7. The method of claim 1, wherein the viral myocarditis is caused by or associated with infection of a Coxsackie Group B virus.

8. The method of claim 1, wherein the viral myocarditis is complicated by pericarditis or endocarditis.

9. The method of claim 1, wherein the viral myocarditis has a clinical feature selected from the group consisting of myocardial damage, heart dysfunction, arrhythmia, systemic symptom and cardiomyopathy.

10. The method of claim 1, wherein the viral myocarditis is an acute or a chronic viral myocarditis.

11. The method of claim 10, wherein the acute viral myocarditis has a clinical feature selected from the group consisting of arrhythmia, heart failure and cardiac shock.

12. The method of claim 1, wherein the viral myocarditis is prolonged with cardiac hypertrophy and/or permanent cardiac muscle injury.

13. The method of claim 1, wherein the DCM has a clinical feature selected from the group consisting of ventricular hypertrophy, myocardial pump function failure and congestive heart failure.

14. The method of claim 1, wherein the neuregulin 1 protein is administered with a pharmaceutically acceptable carrier or excipient.

15. The method of claim 1, further comprising administering a prophylactic or therapeutic agent for viral myocarditis or DCM.

16. The method of claim 15, wherein the neuregulin 1 protein is administered prior to, concurrently with, or subsequent to the administration of the prophylactic or therapeutic agent for viral myocarditis or DCM.

17. The method of claim 15, wherein the prophylactic or therapeutic agent for viral myocarditis is selected from the group consisting of an antibiotic, a heart protective agent, an antioxidant and a nutrient for myocardium.

18. The method of claim 17, wherein the antibiotic is penicillin.

19. The method of claim 17, wherein the heart protective agent is taurine.

20. The method of claim 17, wherein the antioxidant is selected from the group consisting of vitamin C, vitamin E and coenzyme Q 10.

21. The method of claim 17, wherein the nutrient for myocardium is an energy combination.

22. The method of claim 15, wherein the prophylactic or therapeutic agent for DCM is selected from the group consisting of a cardiac tonic, a diuretic, an angiotensin 1-converting enzyme inhibitor (ACEI), a calcium antagonist and a β-receptor antagonist.

23. The method of claim 22, wherein the cardiac tonic is digoxin or cedilanid.

24. The method of claim 22, wherein the diuretic is selected from the group consisting of an inhibitor of carbonic anhydrase, an osmotic diuretic, an inhibitor of $Na^+$—$K+$—$2Cl^-$ symport, an inhibitor of $Na^+$—$Cl^-$symport, an inhibitor of renal epithelial Na+channels and an antagonist of mineralocorticoid receptors.

25. The method of claim 22, wherein the calcium antagonist is amlodipine.

26. The method of claim 22, wherein the β-receptor antagonist is carvedilol.

* * * * *